(12) United States Patent
Awad et al.

(10) Patent No.: US 7,220,760 B2
(45) Date of Patent: May 22, 2007

(54) QUINOLINE DERIVATIVES AS CRTH2 ANTAGONISTS

(75) Inventors: Mohamed M. Ali Awad, Groton, CT (US); Marc J. Bazin, Fresnes (FR); Frederic Feru, Fresnes (FR); Steven W. Goldstein, Groton, CT (US); Cyrille F. Kuhn, Cambridge, MA (US)

(73) Assignee: Pfizer Inc., New York, NY (US)

( * ) Notice: Subject to any disclaimer, the term of this patent is extended or adjusted under 35 U.S.C. 154(b) by 486 days.

(21) Appl. No.: 10/688,566

(22) Filed: Oct. 17, 2003

(65) Prior Publication Data

US 2004/0132772 A1 Jul. 8, 2004

Related U.S. Application Data

(60) Provisional application No. 60/434,896, filed on Dec. 19, 2002.

(30) Foreign Application Priority Data

Oct. 21, 2002 (EP) .................................. 02292606

(51) Int. Cl.
*A61K 31/47* (2006.01)
*C07D 215/02* (2006.01)
(52) U.S. Cl. ...................... 514/313; 546/112; 546/152; 546/159; 514/311; 514/314
(58) Field of Classification Search ................ 546/112, 546/152, 159; 514/311, 313, 314
See application file for complete search history.

(56) References Cited

U.S. PATENT DOCUMENTS

| | | | | |
|---|---|---|---|---|
| 4,521,607 A | 6/1985 | Oka et al. | ....................... | 549/39 |
| 5,753,677 A * | 5/1998 | Ogawa et al. | ............... | 514/311 |
| 6,140,342 A | 10/2000 | Goldstein et al. | ........... | 514/313 |
| 6,140,343 A | 10/2000 | DeNinno et al. | ........... | 514/313 |
| 6,147,089 A | 11/2000 | DeNinno et al. | ........... | 514/313 |
| 6,147,090 A | 11/2000 | DeNinno et al. | ........... | 514/313 |
| 6,197,786 B1 | 3/2001 | DeNinno et al. | ........... | 514/313 |
| 6,310,075 B1 | 10/2001 | DeNinno et al. | ........... | 514/313 |
| 6,362,198 B1 | 3/2002 | Goldstein et al. | ........... | 514/313 |
| 6,395,751 B1 | 5/2002 | DeNinno et al. | ........... | 514/313 |
| 6,489,478 B1 | 12/2002 | DeNinno et al. | ........... | 546/159 |
| 6,586,448 B1 | 7/2003 | DeNinno et al. | ........... | 514/313 |
| 6,906,082 B2 | 6/2005 | DeNinno et al. | ........... | 514/313 |
| 2004/0082609 A1 | 4/2004 | Ghosh et al. | ................ | 514/312 |
| 2005/0038070 A1 | 2/2005 | Inman et al. | ................ | 514/313 |
| 2005/0228016 A1 | 10/2005 | Michelotti et al. | .......... | 514/313 |
| 2006/0063803 A1 | 3/2006 | Ruggeri et al. | ............. | 514/313 |

FOREIGN PATENT DOCUMENTS

| | | |
|---|---|---|
| EP | 0987251 | 3/2000 |
| EP | 1170594 | 1/2002 |
| JP | 200253557 | 2/2002 |
| WO | WO 9105549 | 5/1991 |
| WO | WO 0017165 | 3/2000 |
| WO | WO 02079165 | 10/2002 |
| WO | WO2004052863 | 6/2004 |

OTHER PUBLICATIONS

Hiroyuki Abe, et al, Gene, 227, 1999, pp. 71-77.
Kinya Nagata, et al, FEBS Letters, 459, 1999, pp. 195-199.
XP 002244840, Zhumal Obschchei Khimii, 1963, 33(6), p. 1956-1958.
XP 002244841, MCL Screening Compounds, May 24, 2001, Accession #2001:10000970 CHEMCATS.
XP 002244842, Scientific Exchange Product Line, Accession # 2003:294034 CHEMCATS, Jan. 2003.
XP 002244843, Enamine Product Listing, Accession #2000:1095101 CHEMCATS, Nov. 15, 2001.
XP 002244839, 1966, No. 4, p. 5-16, Trudy Problemnio Laboratoirii Khimii Vysokomolekulyamykh Soedinenii.
XP 002244845, Vitas-M Screening Collection, Accession #2002:304333 CHEMCATS, Mar. 22, 2001.
XP 002244844, MicroChemistry Screening Collection, Accession #2001:2763118 CHEMCATS, Oct. 3.
XP 002244846, ChemBridge Product List, Accession #2002:601263 CHEMCATS, Jan. 17, 2002.
XP 002244847, Interchim Intermediates, Accession # 2002:2633209 CHEMCATS, Jul. 9.
U.S. Appl. No. 10/807,838, filed Mar. 23, 2004 (our reference:PC25623A).
U.S. Appl. No. 60/612,863, filed Sep. 23, 2004 (our reference:PC32562).
U.S. Appl. No. 60/612,729, filed Sep. 23, 2004 (our reference:PC32416).
English Translation of WO 2004/052863.

* cited by examiner

*Primary Examiner*—Golam M. M. Shameem
(74) *Attorney, Agent, or Firm*—Gregg C. Benson; Lisa A. Samuels

(57) ABSTRACT

The invetion relates to compounds of formula (I)

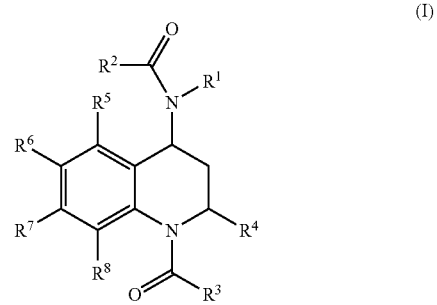

(I)

wherein $R^1$, $R^2$, $R^3$, $R^4$, $R^5$, $R^6$, $R^7$ and $R^8$ are as defined in the description, their use as medicament, pharmaceutical compositions containing them and processes for their preparation.

33 Claims, No Drawings

QUINOLINE DERIVATIVES AS CRTH2 ANTAGONISTS

FIELD OF THE INVENTION

The invention relates to quinoline derivatives, pharmaceutical compositions containing them, processes for their preparation and their use as medicament.

BACKGROUND OF THE INVENTION

In 1999, Nagata et al identified CRTH2 (chemoattractant receptor-homologous molecule expressed on Th2 cells), a novel G protein-coupled receptor (GPCR) belonging to the leucocyte chemoattractant receptor family.

The CRTH2 receptor is selectively expressed from a wide variety of tissues including the brain, lung and lymphoid organs in mouse (Abe et al., Gene (1999) 227 (1):71–7). With respect to expression from immune system cells, it is reported that CRTH2 receptor is selectively expressed on Th2 cells, eosinophils and basophils, but not Th1 cells, B cells and NK cells in human (Nagata et al., FEBS Letters (1999) 459 (2):195–9).

Bauer et al, (see EP1170594A2) identified Prostaglandine $D_2$ ($PGD_2$) as the endogenous ligand of CRTH2. $PGD_2$ is released from immunologically stimulated mast cells and Th2 cells.

Interaction of CRTH2 with $PGD_2$ plays a critical role in the allergen-induced recruitment of Th2 cells in the target tissues of allergic inflammation. In addition, CRTH2 mediates $PGD_2$ dependent cell migration of blood eosinophils and basophils.

Allergic asthma and allergic rhinitis are diseases that currently affect about 10% of the population, and that number appears to be increasing (Bush, R. K. a. G., John W., Handbook of asthma and rhinitis. 1st ed. (1997), Abingdon: Blackwell Science. 270). Currently numerous classes of pharmaceutical agents are widely used to treat these diseases, for example, antihistamines, decongestants, β2 agonists, anticholinergics, methylxanthines, cromolyns, corticosteroids, and leukotriene modulators. Generally however, the usefulness of these agents is limited by side effects and low efficacy. Accordingly, there is a critical medical need to identify pharmaceutically active compounds that interfere with key steps of the inflammatory and immunological processes that contribute to these disease states, and other inflammatory conditions.

EP 987251 discloses cholesteryl ester transfer protein of formula

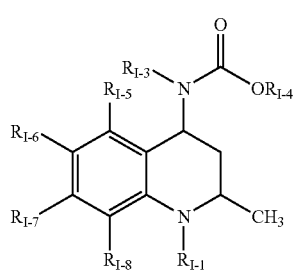

for use in the treatment of diseases affected by low levels of HDL cholesterol and/or high levels of LDL-cholesterol and triglycerides such as atherosclerosis and cardiovascular diseases.

WO91/05549 discloses compounds of formula

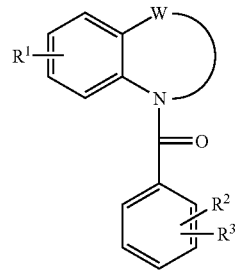

for use as vasodilator, hypotensive agent, water diuretics and platelet agglutination inhibitor.

U.S. Pat. No. 4,521,607 discloses compounds of formula

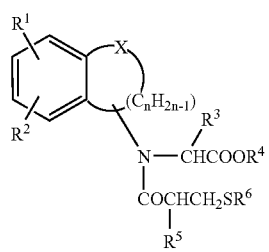

for use as antihypertensives.

WO 02/079165 discloses compounds of formula

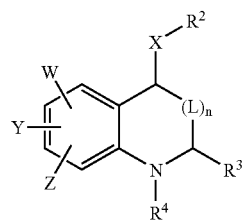

as STAT6 signaling pathway modulators.

SUMMARY OF THE INVENTION

The invention relates to quinoline derivatives of general formula (I)

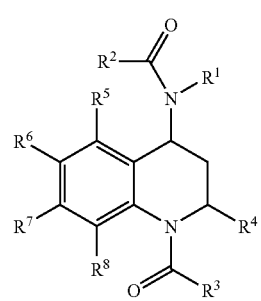

(I)

wherein,
R¹ represents H, (C₁–C₄)alkyl, (C₂–C₄)alkenyl, (C₂–C₄) alkynyl or (CH₂)ₘ—R'¹, in which
R'¹ is selected from aromatic heterocycle, phenyl and (C₃–C₆)cycloalkyl wherein the phenyl, the heterocycle and the cycloalkyl groups are unsubstituted or substituted by one or several groups, preferably 1 to 3, selected from
Q¹, and,
(C₁–C₄)alkyl optionally substituted with one or several, preferably 1 to 3, groups which are the same or different and which are selected from Q¹,
wherein Q¹ is selected from halogen, NO₂, CN, SO₂CH₃, SO₂NR⁹R¹⁰, OR⁹, COOR⁹, C(=O)NR⁹R¹⁰, NR⁹R¹⁰, NR⁹SO₂R¹⁰, NR⁹C(=O)R¹⁰ and C(=O)R⁹ wherein R⁹ and R¹⁰ are the same or different and are selected from H and (C₁–C₄)alkyl;
m is an integer selected from 0, 1 and 2;
R² represents (C₁–C₄)alkyl, wherein the alkyl group may be substituted with one or several, substituents, preferably 1 to 3, selected from halogen, OR⁹, NR⁹R¹⁰, COOR⁹, C(=O)NR⁹R¹⁰, NHSO₂R⁹ and C(=O) (C₁–C₄)alkyl wherein R⁹ and R¹⁰ are the same or different and are selected from H and (C₁–C₄)alkyl;
R³ represents (C₃–C₆)cycloalkyl or -A-R'³, wherein
A represents a bond, straight or branched (C₁–C₃) alkylene, or (C₂–C₃)alkenylene;
R'³ represents (C₆–C₁₂)aryl or an heterocycle, optionally aromatic, having from 5 to 10 atoms in the cycle, wherein the aryl and the heterocycle groups are unsubstituted or substituted by one or several substituents, preferably 1 to 3, selected from,
(C₆–C₁₂)aryl, an aromatic heterocycle,
Q², and,
(C₁–C₄)alkyl optionally substituted with one or several, preferably 1 to 3, groups which are the same or different and which are selected from Q²,
wherein Q² is selected from halogen, NO₂, CN, SO₂CH₃, SO₂NR⁹R¹⁰, OR⁹, SR⁹, OCH₂CF₃, COOR⁹, C(=O) NR⁹R¹⁰, NR⁹R¹⁰, NR⁹SO₂R¹⁰, NR⁹C(=O)R¹⁰ and C(=O) R⁹ wherein R⁹ and R¹⁰ are the same or different and are selected from H and (C₁–C₄)alkyl;
R⁴ represents H or (C₁–C₄)-alkyl;
R⁵, R⁶, R⁷ and R⁸ are the same or different and are selected from
H, Q³, and,
(C₁–C₄)alkyl optionally substituted with one or several groups, preferably 1 to 3, which are the same or different and which are selected from Q³,
wherein Q³ is selected from halogen, NO₂, CN, SO₂CH₃, SO₂NR⁹R¹⁰, OR⁹, SR⁹COOR⁹, C(=O)NR⁹R¹⁰, NR⁹R¹⁰, NR⁹SO₂R¹⁰, NR⁹C(=O)R¹⁰ and C(=O)R⁹ wherein R⁹ and R¹⁰ are the same or different and are selected from H and (C₁–C₄)alkyl;

their optical isomers, as well as their N-oxides and pharmaceutically acceptable salts and their use as medicament.

The invention further concerns the use of a compound of formula (I) for the preparation of a medicament for the prevention or the treatment of disorders for which therapy by a CRTH2 antagonist is relevant.

The invention also provides a method for the treatment of a disorder for which therapy by a CRTH2 antagonist is relevant, comprising administering to a mammal in need thereof an effective amount of a compound of formula (I).

The invention also concerns a pharmaceutical composition comprising a compound of formula (I) together with a pharmaceutically acceptable carrier, excipient, diluent or delivery system.

The invention further relates to processes for the preparation of compounds of formula (I).

DETAILED DESCRIPTION OF THE INVENTION

The invention relates to quinoline derivatives of formula (I)

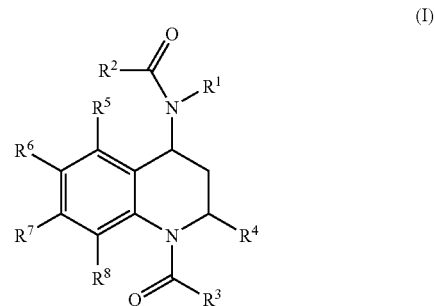

(I)

wherein R¹, R², R³, R⁴, R⁵, R⁶, R⁷ and R⁸ are as defined in the summary of the invention.

their optical isomers, as well as their N-oxides and pharmaceutically acceptable salts and their use as CRTH2 antagonist and as medicament.

These compounds are selective CRTH2 antagonists. In man, CRTH2 is selectively expressed on immune system cells, and in particular on Th2 cells, eosinophils and basophils. CRTH2 plays a critical role in the recruitment of these cells. The compounds of the invention are useful for the prevention or treatment of diseases states involving Th2 cells, eosinophils and/or basophils. In particular, the compounds of the invention are useful in the prevention and treatment of disease states involving inflammatory components, including, without limitation, inflammatory disorders such as rheumatoid arthritis, osteoarthritis, atherosclerosis, Crohn's disease, colitis ulcerosa, inflammatory bowel disease; disorders of the skin including psoriasis, eczema, erythema, pruritis, and acne; systemic lupus erythematous, chronic obstructive pulmonary disease, angioedema, stroke, any disease marked by reperfusion injury, graft rejection, and autoimmune diseases, allergic diseases, such as allergic asthma, atopic dermatitis, and allergic rhinitis.

The compounds of the invention are also useful as research tools that can be used to antagonize the CRTH2 receptor. For example, to determine the signaling pathway of a PGD₂ mediated effect, it is essential to find out which PGD₂ receptor is involved in said pathway. This can be achieved only if selective antagonists are available for each of the PGD₂ receptors. The compounds of the invention, which are selective CRTH2 antagonists can be used for that purpose.

Preferred compounds of the invention are compounds of formula (I) wherein R¹, R², R³, R⁴, R⁵, R⁶, R⁷ and R⁸ are as defined in the summary of the invention with the exclusion of:
N-(1-benzoyl-6-bromo-1,2,3,4-tetrahydro-2-methyl-4-quinolyl)-acetanilide, N-(1-benzoyl-6-chloro-1,2,3,4-tetrahydro-2-methyl-4-quinolyl)-acetanilide,
N-(1-benzoyl-1,2,3,4-tetrahydro-2-methyl-4-quinolinyl)-N-(4-methoxyphenyl)-2-methyl-propanamide,
N-[1-(4-fluorobenzoyl)-1,2,3,4-tetrahydro-2-methyl-4-quinolinyl]-N-phenyl-butanamide,
N-phenyl-N-[1,2,3,4-tetrahydro-1-(3-methoxybenzoyl)-2-methyl-4-quinolinyl]-pentanamide,
N-[1-[(4-fluorophenyl)acetyl]-1,2,3,4-tetrahydro-2-methyl-4-quinolinyl]-N-phenyl-propanamide,
N-(1-benzoyl-1,2,3,4-tetrahydro-2-methyl-4-quinolinyl)-2,2-dimethyl-N-phenyl-propanamide,
N-(1-benzoyl-6-bromo-1,2,3,4-tetrahydro-2-methyl-4-quinolinyl)-N-phenyl-pentanamide,
N-[1-(2-furanylcarbonyl)-1,2,3,4-tetrahydro-2-methyl-4-quinolinyl]-N-phenyl-acetamide,
2-methyl-N-phenyl-N-[1,2,3,4-tetrahydro-1-(3-methoxybenzoyl)-2-methyl-4-quinolinyl]-propanamide,
2,2,2-trifluoro-N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-(3-methoxyphenyl)-acetamide,
N-(1-benzoyl-1,2,3,4-tetrahydro-2-methyl-4-quinolinyl)-N-(4-methylphenyl)-acetamide,
N-[1-(4-chloro-3-nitrobenzoyl)-1,2,3,4-tetrahydro-2-methyl-4-quinolinyl]-N-phenyl-acetamide,
N-phenyl-N-[1,2,3,4-tetrahydro-2-methyl-1-(3-nitrobenzoyl)-4-quinolinyl]-acetamide,
N-phenyl-N-[1,2,3,4-tetrahydro-1-[3-(4-methoxyphenyl)-1-oxo-2-propenyl]-2-methyl-4-quinolinyl]-acetamide,
N-[1-(3-chlorobenzoyl)-1,2,3,4-tetrahydro-2-methyl-4-quinolinyl]-N-phenyl-acetamide,
N-[1-(3-fluorobenzoyl)-1,2,3,4-tetrahydro-2-methyl-4-quinolinyl]-N-phenyl-acetamide,
N-[1-[4-(1,1-dimethylethyl)benzoyl]-1,2,3,4-tetrahydro-2-methyl-4-quinolinyl]-N-phenyl-acetamide,
N-phenyl-N-[1,2,3,4-tetrahydro-2-methyl-1-(1-oxo-3-phenyl-2-propenyl)-4-quinolinyl]-acetamide,
N-phenyl-N-[1,2,3,4-tetrahydro-2-methyl-1-(2-thienylcarbonyl)-4-quinolinyl]-acetamide,
N-phenyl-N-[1,2,3,4-tetrahydro-1-(4-methoxybenzoyl)-2-methyl-4-quinolinyl]-acetamide,
N-[1-(3,5-dinitrobenzoyl)-1,2,3,4-tetrahydro-2-methyl-4-quinolinyl]-N-phenyl-acetamide,
N-phenyl-N-[1,2,3,4-tetrahydro-2-methyl-1-(4-nitrobenzoyl)-4-quinolinyl]-acetamide,
N-phenyl-N-[1,2,3,4-tetrahydro-1-(2-iodobenzoyl)-2-methyl-4-quinolinyl]-acetamide,
N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-phenyl-pentanamide,
N-(1-benzoyl-1,2,3,4-tetrahydro-2-methyl-4-quinolinyl)-N-phenyl-butanamide,
N-(1-benzoyl-1,2,3,4-tetrahydro-2-methyl-4-quinolinyl)-N-phenyl-propanamide,
1-benzoyl-1,2,3,4-tetrahydro-4-(N-phenylacetamido)-quinaldine,
N-[(1-benzoyl-1,2,3,4-tetrahydro-2-methyl-4-quinolinyl]-2-methyl-N-phenyl propanamide;
N-[1-(4-bromobenzoyl)-1,2,3,4-tetrahydro-2,6-dimethyl-4-quinolinyl]-acetamide;
N-(1-benzoyl-1,2,3,4-tetrahydro-2,6-dimethyl-4-quinolinyl)-acetamide; and,
N-(1-benzoyl-1,2,3,4-tetrahydro-2-methyl-4-quinolinyl)-acetamide.

A further preferred group of compounds are cis-isomers of formula (Ia) and (Ib),

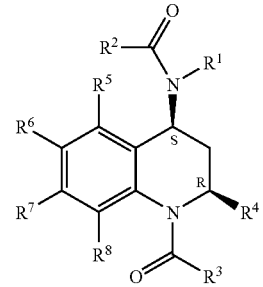

(Ia)

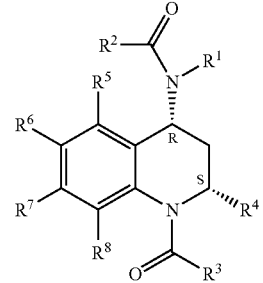

(Ib)

wherein $R^1$, $R^2$, $R^3$, $R^5$, $R^6$, $R^7$ and $R^8$ are as defined in compound of formula (I) the summary of the invention and $R^4$ is $(C_1-C_4)$alkyl, with the exclusion of the following compounds,
N-[(2R,4S)-1-benzoyl-1,2,3,4-tetrahydro-2-methyl-4-quinolinyl]-2-methyl-N-phenyl propanamide;
N-[(2R,4S)-1-benzoyl-1,2,3,4-tetrahydro-2-methyl-4-quinolinyl]-2,2-dimethyl-N-phenyl-propanamide;
N-[(2R,4S)-1-benzoyl-1,2,3,4-tetrahydro-2-methyl-4-quinolinyl]-N-phenyl butanamide;
N-[(2R,4S)-1-benzoyl-1,2,3,4-tetrahydro-2-methyl-4-quinolinyl]-N-phenyl acetamide,
N-[(2R,4S)-1-benzoyl-1,2,3,4-tetrahydro-2-methyl-4-quinolinyl]-N-phenyl-pentanamide and,
N-[(2R,4S)-1-benzoyl-1,2,3,4-tetrahydro-2-methyl-4-quinolinyl]-acetamide.

Another preferred group of compounds are cis-isomers of formula (Ia) and (Ib), wherein $R^1$, $R^2$, $R^3$, $R^5$ $R^6$ $R^7$ and $R^8$ are as defined in the summary of the invention and $R^4$ is $(C_1-C_4)$alkyl with the exclusion of the cis-isomers of the following compounds,
N-(1-benzoyl-6-bromo-1,2,3,4-tetrahydro-2-methyl-4-quinolyl)-acetanilide,
N-(1-benzoyl-6-chloro-1,2,3,4-tetrahydro-2-methyl-4-quinolyl)-acetanilide,
N-(1-benzoyl-1,2,3,4-tetrahydro-2-methyl-4-quinolinyl)-N-(4-methoxyphenyl)-2-methyl-propanamide,
N-[1-(4-fluorobenzoyl)-1,2,3,4-tetrahydro-2-methyl-4-quinolinyl]-N-phenyl-butanamide,
N-phenyl-N-[1,2,3,4-tetrahydro-1-(3-methoxybenzoyl)-2-methyl-4-quinolinyl]-pentanamide,
N-[1-[(4-fluorophenyl)acetyl]-1,2,3,4-tetrahydro-2-methyl-4-quinolinyl]-N-phenyl-propanamide,
N-(1-benzoyl-1,2,3,4-tetrahydro-2-methyl-4-quinolinyl)-2,2-dimethyl-N-phenyl-propanamide,
N-(1-benzoyl-6-bromo-1,2,3,4-tetrahydro-2-methyl-4-quinolinyl)-N-phenyl-pentanamide, N-[1-(2-furanylcarbonyl)-1,2,3,4-tetrahydro-2-methyl-4-quinolinyl]-N-phenyl-acetamide,
2-methyl-N-phenyl-N-[1,2,3,4-tetrahydro-1-(3-methoxybenzoyl)-2-methyl-4-quinolinyl]-propanamide,
2,2,2-trifluoro-N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-(3-methoxyphenyl)-acetamide,
N-(1-benzoyl-1,2,3,4-tetrahydro-2-methyl-4-quinolinyl)-N-(4-methylphenyl)-acetamide,
N-[1-(4-chloro-3-nitrobenzoyl)-1,2,3,4-tetrahydro-2-methyl-4-quinolinyl]-N-phenyl-acetamide,
N-phenyl-N-[1,2,3,4-tetrahydro-2-methyl-1-(3-nitrobenzoyl)-4-quinolinyl]-acetamide,
N-phenyl-N-[1,2,3,4-tetrahydro-1-[3-(4-methoxyphenyl)-1-oxo-2-propenyl]-2-methyl-4-quinolinyl]-acetamide,
N-[1-(3-chlorobenzoyl)-1,2,3,4-tetrahydro-2-methyl-4-quinolinyl]-N-phenyl-acetamide,
N-[1-(3-fluorobenzoyl)-1,2,3,4-tetrahydro-2-methyl-4-quinolinyl]-N-phenyl-acetamide,
N-[1-[4-(1,1-dimethylethyl)benzoyl]-1,2,3,4-tetrahydro-2-methyl-4-quinolinyl]-N-phenyl-acetamide,
N-phenyl-N-[1,2,3,4-tetrahydro-2-methyl-1-(1-oxo-3-phenyl-2-propenyl)-4-quinolinyl]-acetamide,
N-phenyl-N-[1,2,3,4-tetrahydro-2-methyl-1-(2-thienylcarbonyl)-4-quinolinyl]-acetamide,
N-phenyl-N-[1,2,3,4-tetrahydro-1-(4-methoxybenzoyl)-2-methyl-4-quinolinyl]-acetamide,
N-[1-(3,5-dinitrobenzoyl)-1,2,3,4-tetrahydro-2-methyl-4-quinolinyl]-N-phenyl-acetamide,
N-phenyl-N-[1,2,3,4-tetrahydro-2-methyl-1-(4-nitrobenzoyl)-4-quinolinyl]-acetamide,
N-phenyl-N-[1,2,3,4-tetrahydro-1-(2-iodobenzoyl)-2-methyl-4-quinolinyl]-acetamide,
N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-phenyl-pentanamide,
N-(1-benzoyl-1,2,3,4-tetrahydro-2-methyl-4-quinolinyl)-N-phenyl-butanamide,
N-(1-benzoyl-1,2,3,4-tetrahydro-2-methyl-4-quinolinyl)-N-phenyl-propanamide,
1-benzoyl-1,2,3,4-tetrahydro-4-(N-phenylacetamido)-quinaldine,
N-[1-benzoyl-1,2,3,4-tetrahydro-2-methyl-4-quinolinyl]-2-methyl-N-phenyl propanamide;
N-[1-(4-bromobenzoyl)-1,2,3,4-tetrahydro-2,6-dimethyl-4-quinolinyl]-acetamide;
N-(1-benzoyl-1,2,3,4-tetrahydro-2,6-dimethyl-4-quinolinyl)-acetamide; and,
N-(1-benzoyl-1,2,3,4-tetrahydro-2-methyl-4-quinolinyl)-acetamide.

Another preferred group of compound according to the invention are trans isomers of formula (Ic) or (Id):

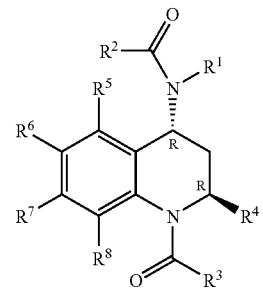

(Ic)

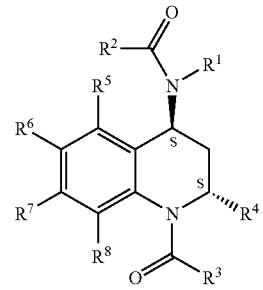

(Id)

wherein $R^1$, $R^2$, $R^3$, $R^5$, $R^6$, $R^7$ and $R^8$ are as defined in compound of formula (I) in the summary of the invention and $R^4$ is $(C_1-C_4)$alkyl.

A preferred group of trans-isomers are those of formula (Ic) or (Id) wherein $R^1$, $R^2$, $R^3$, $R^5$, $R^6$, $R^7$ and $R^8$ are as defined in compound of formula (I) in the summary of the invention and $R^4$ is $(C_1-C_4)$alkyl with the exclusion of the trans-isomers of the following compounds, N-(1-benzoyl-6-bromo-1,2,3,4-tetrahydro-2-methyl-4-quinolyl)-acetanilide,
N-(1-benzoyl-6-chloro-1,2,3,4-tetrahydro-2-methyl-4-quinolyl)-acetanilide,
N-(1-benzoyl-1,2,3,4-tetrahydro-2-methyl-4-quinolinyl)-N-(4-methoxyphenyl)-2-methyl-propanamide,
N-[1-(4-fluorobenzoyl)-1,2,3,4-tetrahydro-2-methyl-4-quinolinyl]-N-phenyl-butanamide,
N-phenyl-N-[1,2,3,4-tetrahydro-1-(3-methoxybenzoyl)-2-methyl-4-quinolinyl]-pentanamide,
N-[1-[(4-fluorophenyl)acetyl]-1,2,3,4-tetrahydro-2-methyl-4-quinolinyl]-N-phenyl-propanamide,
N-(1-benzoyl-1,2,3,4-tetrahydro-2-methyl-4-quinolinyl)-2,2-dimethyl-N-phenyl-propanamide,
N-(1-benzoyl-6-bromo-1,2,3,4-tetrahydro-2-methyl-4-quinolinyl)-N-phenyl-pentanamide,
N-[1-(2-furanylcarbonyl)-1,2,3,4-tetrahydro-2-methyl-4-quinolinyl]-N-phenyl-acetamide,
2-methyl-N-phenyl-N-[1,2,3,4-tetrahydro-1-(3-methoxybenzoyl)-2-methyl-4-quinolinyl]-propanamide,
2,2,2-trifluoro-N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-(3-methoxyphenyl)-acetamide,
N-(1-benzoyl-1,2,3,4-tetrahydro-2-methyl-4-quinolinyl)-N-(4-methylphenyl)-acetamide,
N-[1-(4-chloro-3-nitrobenzoyl)-1,2,3,4-tetrahydro-2-methyl-4-quinolinyl]-N-phenyl-acetamide, N-phenyl-N-[1,2,3,4-tetrahydro-2-methyl-1-(3-nitrobenzoyl)-4-quinolinyl]-acetamide,
N-phenyl-N-[1,2,3,4-tetrahydro-1-[3-(4-methoxyphenyl)-1-oxo-2-propenyl]-2-methyl-4-quinolinyl]-acetamide,
N-[1-(3-chlorobenzoyl)-1,2,3,4-tetrahydro-2-methyl-4-quinolinyl]-N-phenyl-acetamide,
N-[1-(3-fluorobenzoyl)-1,2,3,4-tetrahydro-2-methyl-4-quinolinyl]-N-phenyl-acetamide,
N-[1-[4-(1,1-dimethylethyl)benzoyl]-1,2,3,4-tetrahydro-2-methyl-4-quinolinyl]-N-phenyl-acetamide,
N-phenyl-N-[1,2,3,4-tetrahydro-2-methyl-1-(1-oxo-3-phenyl-2-propenyl)-4-quinolinyl]-acetamide,
N-phenyl-N-[1,2,3,4-tetrahydro-2-methyl-1-(2-thienylcarbonyl)-4-quinolinyl]-acetamide,
N-phenyl-N-[1,2,3,4-tetrahydro-1-(4-methoxybenzoyl)-2-methyl-4-quinolinyl]-acetamide,
N-[1-(3,5-dinitrobenzoyl)-1,2,3,4-tetrahydro-2-methyl-4-quinolinyl]-N-phenyl-acetamide,
N-phenyl-N-[1,2,3,4-tetrahydro-2-methyl-1-(4-nitrobenzoyl)-4-quinolinyl]-acetamide,
N-phenyl-N-[1,2,3,4-tetrahydro-1-(2-iodobenzoyl)-2-methyl-4-quinolinyl]-acetamide,
N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-phenyl-pentanamide,
N-(1-benzoyl-1,2,3,4-tetrahydro-2-methyl-4-quinolinyl)-N-phenyl-butanamide,
N-(1-benzoyl-1,2,3,4-tetrahydro-2-methyl-4-quinolinyl)-N-phenyl-propanamide,
1-benzoyl-1,2,3,4-tetrahydro-4-(N-phenylacetamido)-quinaldine,
N-[1-benzoyl-1,2,3,4-tetrahydro-2-methyl-4-quinolinyl]-2-methyl-N-phenyl propanamide;
N-[1-(4-bromobenzoyl)-1,2,3,4-tetrahydro-2,6-dimethyl-4-quinolinyl]-acetamide;
N-(1-benzoyl-1,2,3,4-tetrahydro-2,6-dimethyl-4-quinolinyl)-acetamide; and,
N-(1-benzoyl-1,2,3,4-tetrahydro-2-methyl-4-quinolinyl)-acetamide.

Compounds of formula (I) wherein $R^4$ represents $(C_1-C_4)$ alkyl, have two chiral centers, numbered $C^{*1}$ and $C^{*2}$ on the following formula

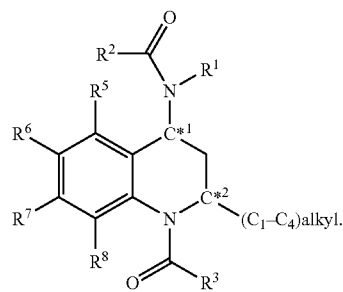

As each of $C^{*1}$ and $C^{*2}$ can have a Cahn-Ingold-prelog configuration R or S, compounds of formula (I) exist in four different forms:
$C^{*1}(R)-C^{*2}(S)-(CIS)$,
$C^{*1}(S)-C^{*2}(R)-(CIS)$,
$C^{*1}(R)-C^{*2}(R)(TRANS)$, and,
$C^{*1}(S)-C^{*2}(S)(TRANS)$.

As mentioned above, a compound of formula (I), wherein $R^4$ represents $(C_1-C_4)$alkyl, includes four diastereoisomers that can be represented by the following formula (Ia), (Ib), (Ic) and (Id):

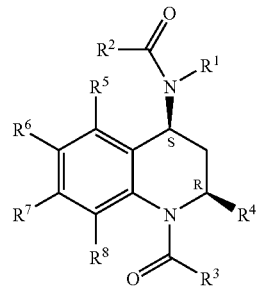

(Ia)

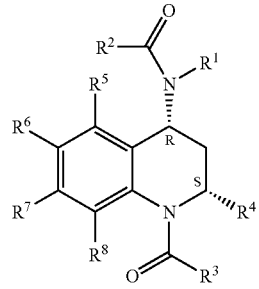

(Ib)

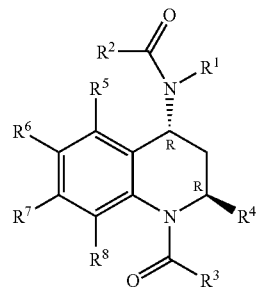

(Ic)

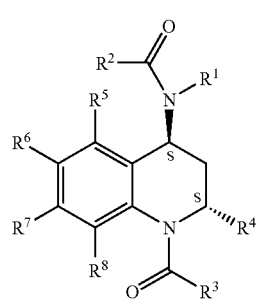

(Id)

wherein (Ia) and (Ib) are the cis isomers and (Ic) and (Id) are the trans isomers.

In the present application, the terms "optical isomer" include the diastereoisomers of formula (Ia), (Ib), (Ic) and (Id) and mixture thereof.

Preferred compounds of formula (I) are compounds of formula (Ia), (Ib) and mixture thereof.

In the above groups of compounds, the following substitutions are further preferred:

Preferably, $R^1$ represents H, $(C_1-C_4)$alkyl, $(C_2-C_4)$alkenyl, $(C_2-C_4)$alkynyl or $(CH_2)_m-R^{1'}$, wherein $R^{1'}$ is selected from phenyl and $(C_3-C_6)$cycloalkyl wherein the phenyl and the cycloalkyl groups are unsubstituted or substituted by one or several groups, preferably 1 to 3, selected from $Q^1$, and, $(C_1-C_4)$alkyl optionally substituted with one or several, preferably 1 to 3, groups which are the same or different and which are selected from $Q^1$, wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl;

m is an integer selected from 0, 1 and 2;

and $R^2$, $R^3$, $R^4$, $R^5$, $R^6$, $R^7$ and $R^8$ are as defined in the summary of the invention.

Preferably, $R^1$ represents $(CH_2)_m-R'^1$, wherein $R'^1$ is selected from phenyl and $(C_3-C_6)$cycloalkyl wherein the phenyl and the cycloalkyl groups are unsubstituted or substituted by 1 to 3 groups selected from $OR^9$, $COOR^9$ and $(C_1-C_4)$alkyl optionally substituted with a group $COOR^9$ wherein $R^9$ is selected from H or $(C_1-C_4)$alkyl, m is an integer selected from 0 and 1;

and $R^2$, $R^3$, $R^4$, $R^5$, $R^6$, $R^7$ and $R^8$ are as defined in the summary of the invention.

Another preferred group of compounds include compounds of formula (I) wherein $R^1$ represents $(C_1-C_4)$alkyl, $(C_2-C_4)$alkenyl, $(C_2-C_4)$alkynyl or $(CH_2)_m-R'^1$, in which $R'^1$ is selected from aromatic heterocycle and $(C_3-C_6)$ cycloalkyl wherein the heterocycle and the cycloalkyl groups are unsubstituted or substituted by one or several groups, preferably 1 to 3, selected from $Q^1$, and, $(C_1-C_4)$alkyl optionally substituted with one or several, preferably 1 to 3, groups which are the same or different and which are selected from $Q^1$, wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl;

m is an integer selected from 0, 1 and 2;

and $R^2$, $R^3$, $R^4$, $R^5$, $R^6$, $R^7$ and $R^8$ are as defined in the summary of the invention.

Preferably $R^1$ represents a $(C_3-C_6)$cycloalkyl wherein the cycloalkyl group is unsubstituted or substituted by one or several groups, preferably 1 to 3, selected from $Q^1$, and, $(C_1-C_4)$alkyl optionally substituted with one or several, preferably 1 to 3, groups which are the same or different and which are selected from $Q^1$, wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl;

m is an integer selected from 0, 1 and 2.

Preferably, $R^1$ represents a $(C_3-C_6)$cycloalkyl, more preferably, a cyclopropyl group.

Preferably, $R^1$ is phenyl unsubstituted or substituted in the para position by a substituent selected from halogen, $OR^9$, $CH_2COOR^9$ and $CH_2COOR^9$ wherein $R^9$ is selected from H and $(C_1-C_4)$alkyl.

Preferably, $R^2$ represents $(C_1-C_4)$alkyl, optionally substituted with $COOR^9$ wherein $R^9$ is selected from H and $(C_1-C_4)$alkyl.

Preferably, $R^2$ represents unsubstituted $(C_1-C_4)$alkyl, more preferably a methyl group.

$R^3$ is preferably selected from $(C_3-C_6)$cycloalkyl and -A-$R'^3$, wherein

A represents a bond, $(C_1-C_3)$alkylene, straight or branched, or $(C_2-C_3)$alkenylene;

$R'^3$ represents an heterocycle, optionally aromatic, having from 5 to 10 atoms in the cycle, unsubstituted or substituted by one or several, preferably 1 to 3, substituents selected from, $(C_6-C_{12})$aryl, an heterocycle, $Q^2$, and, $(C_1-C_4)$alkyl optionally substituted with one or several, preferably 1 to 3, groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl, with the proviso that $R^3$ is not selected from unsubstituted thienyl or unsubstituted furanyl.

Preferably, $R^3$ is selected from $(C_3-C_6)$cycloalkyl and -A-$R'^3$, wherein

A represents a bond, $(C_1-C_3)$alkylene, straight or branched, or $(C_2-C_3)$alkenylene;

$R'^3$ represents isoxazolyl, pyrazolyl, pyrrolyl, thiazolyl, thiadiazolyl, isothiazolyl, thiazolyl, tetrazolyl or an heterocycle, optionally aromatic, having from 6 to 10 atoms in the cycle, unsubstituted or substituted by one or several, preferably 1 to 3, substituents selected from, $(C_6-C_{12})$aryl, an heterocycle, $Q^2$, and, $(C_1-C_4)$alkyl optionally substituted with one or several, preferably 1 to 3, groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl;

Preferably, $R^3$ is selected from -A-$R'^3$, wherein

A represents a bond;

$R'^3$ represents isoxazolyl, pyrazolyl, pyrrolyl, thiazolyl, thiadiazolyl, isothiazolyl, thiazolyl, tetrazolyl or an heterocycle, optionally aromatic, having from 6 to 10 atoms in the cycle, unsubstituted or substituted by one or several, preferably 1 to 3, substituents selected from, $(C_6-C_{12})$aryl, an heterocycle, $Q^2$, and, $(C_1-C_4)$alkyl optionally substituted with one or several, preferably 1 to 3, groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl.

Preferably, $R^3$ is selected from -A-$R'^3$, wherein

A represents a bond, straight or branched $(C_1-C_3)$alkylene, or $(C_2-C_3)$alkenylene;

R¹³ represents $(C_6-C_{12})$aryl, preferably phenyl, unsubstituted or substituted by one or several, preferably 1 to 3, substituents selected from,
$(C_6-C_{12})$aryl, an heterocycle,
$Q^2$, and,
$(C_1-C_4)$alkyl optionally substituted with one or several, preferably 1 to 3, groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl.

Preferably, $R^3$ is selected from -A-R¹³, wherein
A represents a bond, straight or branched $(C_1-C_3)$alkylene, or $(C_2-C_3)$alkenylene;
R¹³ represents a phenyl, unsubstituted or substituted by 1 to 3, substituents selected from $(C_6-C_{12})$aryl, heterocycle, halogen, CN, $CF_3$, $OR^9$ and $COOR^9$ wherein $R^9$ is selected from H and $(C_1-C_4)$alkyl.

Preferably, $R^4$ represents $(C_1-C_4)$alkyl, more preferably a methyl group.

Preferably $R^5$, $R^6$, $R^7$ and $R^8$ are the same or different and are selected from H, halogen and $OR^9$ wherein $R^9$ is selected from H and $(C_1-C_4)$alkyl.

In the following and in the foregoing text:
Halogen includes fluoro, chloro, bromo, and iodo.
Alkyl groups include straight or branched carbon chains. Examples of $(C_1-C_4)$alkyl groups are methyl, ethyl, propyl, isopropyl, n-butyl, isobutyl and tert-butyl.

The term alkenyl groups include straight and branched hydrocarbon radicals having at least one double bond. Examples of $(C_2-C_4)$alkenyl groups are ethenyl, 3-buten-1-yl and the like.

The term alkynyl groups includes straight and branched hydrocarbon radicals having at least one triple bond. Examples of $(C_2-C_4)$ alkynyl are ethynyl, 3-butyn-1-yl, propynyl, and the like.

The term $(C_3-C_6)$cycloalkyl includes cyclopropyl, cyclobutyl, cyclopentyl and cyclohexyl.

The term heterocycle includes carbocycles, optionally aromatic, having from 5 to 10 atoms in the cycle, containing from 1 to 4 heteroatoms selected from O, S and N in the cycle. A preferred group of heterocycles includes 5 or 6-membered heterocycles containing from 1 to 3 heteroatoms selected from O, S and N.

Particularly preferred heterocycles are isoxazolyl, oxazolyl thienyl, pyrazolyl, pyrrolyl, triazolyl, tetrazolyl, thiazolyl, isothiazolyl, thiadiazolyl, pyridinyl, pyrazinyl, benzo-oxadiazolyl or pyrazolo-pyridinyl, quinolinyl and quinoxalinyl.

$(C_6-C_{12})$aryl is understood to refer to an aromatic carbocycle containing between 6 and 12 carbon atoms. A preferred aryl group is phenyl.

Preferred compounds are:
Cis-N-[2-Methyl-1-(thiophene-2-carbonyl)-1,2,3,4-tetrahydroquinolin-4-yl]-N-phenyl-acetamide;
Cis-(1-Benzoyl-2-methyl-1,2,3,4-tetrahydroquinolin-4-yl)-N-phenyl-acetamide;
Cis-N-[2-Methyl-1-(pyridine-4-carbonyl)-1,2,3,4-tetrahydroquinolin-4-yl]-N-phenyl-acetamide;
Cis-N-[2-Methyl-1-(1-oxy-pyridine-4-carbonyl)-1,2,3,4-tetrahydroquinolin-4-yl]-N-phenyl-acetamide;
Cis-N-[1-(4-Methoxy-benzoyl)-2-methyl-1,2,3,4-tetrahydroquinolin-4-yl]-N-phenyl-acetamide;
Cis-N-[1-(4-Hydroxy-benzoyl)-2-methyl-1,2,3,4-tetrahydroquinolin-4-yl]-N-phenyl-acetamide;
Cis-N-[2-Methyl-1-(4-trifluoromethyl-benzoyl)-1,2,3,4-tetrahydroquinolin-4-yl]-N-phenyl-acetamide;
Cis-N-[2-Methyl-1-(3-phenyl-acryloyl)-1,2,3,4-tetrahydroquinolin-4-yl]-N-phenyl-acetamide;
Cis-N-[1-(4-Cyano-benzoyl)-2-methyl-1,2,3,4-tetrahydroquinolin-4-yl]-N-phenyl-acetamide;
Cis-N-[1-(4-Chloro-benzoyl)-2-methyl-1,2,3,4-tetrahydroquinolin-4-yl]-N-phenyl-acetamide;
4-[Cis-4-(Acetyl-phenyl-amino)-2-methyl-3,4-dihydro-2H-quinoline-1-carbonyl]-benzoic acid methyl ester;
4-[Cis-4-(Acetyl-phenyl-amino)-2-methyl-3,4-dihydro-2H-quinoline-1-carbonyl]-benzoic acid;
Cis-N-[2-Methyl-1-(3-phenyl-propionyl)-1,2,3,4-tetrahydroquinolin-4-yl]-N-phenyl-acetamide;
Cis-N-[2-Methyl-1-(5-methyl-thiophene-2-carbonyl)-1,2,3,4-tetrahydroquinolin-4-yl]-N-phenyl-acetamide;
Cis-N-[1-(Benzofurazan-5-carbonyl)-2-methyl-1,2,3,4-tetrahydroquinolin-4-yl]-N-phenyl-acetamide;
Cis-N-(2-Methyl-1-phenylacetyl-1,2,3,4-tetrahydroquinolin-4-yl)-N-phenyl-acetamide;
Cis-N-[2-Methyl-1-(pyrazine-2-carbonyl)-1,2,3,4-tetrahydroquinolin-4-yl]-N-phenyl-acetamide;
Cis-N-[1-(6-Chloro-pyridine-3-carbonyl)-2-methyl-1,2,3,4-tetrahydroquinolin-4-yl]-N-phenyl-acetamide;
Cis-N-[2-Methyl-1-(6-trifluoromethyl-pyridine-3-carbonyl)-1,2,3,4-tetrahydroquinolin-4-yl]-N-phenyl-acetamide;
Cis-N-[1-(2,6-Dimethoxy-pyridine-3-carbonyl)-2-methyl-1,2,3,4-tetrahydroquinolin-4-yl]-N-phenyl-acetamide;
Cis-N-[1-(2-Methoxy-pyridine-3-carbonyl)-2-methyl-1,2,3,4-tetrahydroquinolin-4-yl]-N-phenyl-acetamide;
Cis-N-[2-Methyl-1-(2-methylsulfanyl-pyridine-3-carbonyl)-1,2,3,4-tetrahydroquinolin-4-yl]-N-phenyl-acetamide;
Cis-N-[1-(2-Chloro-pyridine-3-carbonyl)-2-methyl-1,2,3,4-tetrahydroquinolin-4-yl]-N-phenyl-acetamide;
Cis-N-[2-Methyl-1-(5-methyl-pyrazine-2-carbonyl)-1,2,3,4-tetrahydroquinolin-4-yl]-N-phenyl-acetamide;
Cis-N-[1-(2-Chloro-6-methyl-pyridine-3-carbonyl)-2-methyl-1,2,3,4-tetrahydroquinolin-4-yl]-N-phenyl-acetamide;
Cis-N-[1-(4-Chloro-1,3-dimethyl-1H-pyrazolo[3,4-b]pyridine-3-carbonyl)-2-methyl-1,2,3,4-tetrahydroquinolin-4-yl]-N-phenyl-acetamide;
Cis-N-[2-Methyl-1-(6-(2,2,2-trifluoro-ethoxy)-pyridine-3-carbonyl)-1,2,3,4-tetrahydroquinolin-4-yl]-N-phenyl-acetamide;
Cis-N-[2-Methyl-1-(2-propylsulfanyl-pyridine-3-carbonyl)-1,2,3,4-tetrahydroquinolin-4-yl]-N-phenyl-acetamide;
Cis-N-[1-(5,6-Dichloro-pyridine-3-carbonyl)-2-methyl-1,2,3,4-tetrahydroquinolin-4-yl]-N-phenyl-acetamide;
Cis-N-[1-(2,6-Dichloro-pyridine-3-carbonyl)-2-methyl-1,2,3,4-tetrahydroquinolin-4-yl]-N-phenyl-acetamide;
Cis-N-[2-Methyl-1-(4-methyl-[1,2,3]thiadiazole-5-carbonyl)-1,2,3,4-tetrahydroquinolin-4-yl]-N-phenyl-acetamide;
Cis-N-[2-Methyl-1-(5-methyl-isoxazole-3-carbonyl)-1,2,3,4-tetrahydroquinolin-4-yl]-N-phenyl-acetamide;
Cis-N-[1-(2,5-Dimethyl-2H-pyrazole-3-carbonyl)-2-methyl-1,2,3,4-tetrahydroquinolin-4-yl]-N-phenyl-acetamide;
Cis-N-[2-Methyl-1-(1-methyl-1H-pyrrole-2-carbonyl)-1,2,3,4-tetrahydroquinolin-4-yl]-N-phenyl-acetamide;
Cis-N-[1-(Isoxazole-5-carbonyl)-2-methyl-1,2,3,4-tetrahydroquinolin-4-yl]-N-phenyl-acetamide;

Cis-N-[2-Methyl-1-(5-methyl-isoxazole-4-carbonyl)-1,2,3,4-tetrahydroquinolin-4-yl]-N-phenyl-acetamide;
Cis-N-[1-(2,4-Dimethyl-thiazole-5-carbonyl)-2-methyl-1,2,3,4-tetrahydroquinolin-4-yl]-N-phenyl-acetamide;
Cis-N-[1-(5-Chloro-thiophene-2-carbonyl)-2-methyl-1,2,3,4-tetrahydroquinolin-4-yl]-N-phenyl-acetamide;
Cis-N-[1-(1,5-Dimethyl-1H-pyrazole-3-carbonyl)-2-methyl-1,2,3,4-tetrahydroquinolin-4-yl]-N-phenyl-acetamide;
Cis-N-[2-Methyl-1-(4-methyl-isothiazole-5-carbonyl)-1,2,3,4-tetrahydroquinolin-4-yl]-N-phenyl-acetamide
Cis-5-[4-(Acetyl-phenyl-amino)-2-methyl-3,4-dihydro-2H-quinoline-1-carbonyl]-thiophene-2-carboxylic acid dimethylamide
Cis-N-[1-(4-Hydroxy-quinoline-6-carbonyl)-2-methyl-1,2,3,4-tetrahydroquinolin-4-yl]-N-phenyl-acetamide
Cis-N-[1-(4-tert-Butyl-thiazole-2-carbonyl)-2-methyl-1,2,3,4-tetrahydroquinolin-4-yl]-N-phenyl-acetamide
Cis-N-[1-(4-tert-Butyl-thiazole-2-carbonyl)-2-methyl-1,2,3,4-tetrahydroquinolin-4-yl]-N-phenyl-acetamide
Cis-N-[1-(2-Ethyl-pyridine-4-carbonyl)-2-methyl-1,2,3,4-tetrahydroquinolin-4-yl]-N-phenyl-acetamide
Cis-N-[1-(3,6-Dichloro-pyridine-2-carbonyl)-2-methyl-1,2,3,4-tetrahydroquinolin-4-yl]-N-phenyl-acetamide
Cis-N-[1-(4-Chloro-2H-pyrazole-3-carbonyl)-2-methyl-1,2,3,4-tetrahydroquinolin-4-yl]-N-phenyl-acetamide
Cis-2-[4-(Acetyl-phenyl-amino)-2-methyl-3,4-dihydro-2H-quinoline-1-carbonyl]-isonicotinic acid methyl ester
Cis-N-[2-Methyl-1-(4-[1,2,4]triazol-4-yl-benzoyl)-1,2,3,4-tetrahydroquinolin-4-yl]-N-phenyl-acetamide
Cis-N-[1-(2,6-Dimethoxy-pyridine-4-carbonyl)-2-methyl-1,2,3,4-tetrahydroquinolin-4-yl]-N-phenyl-acetamide
Cis-N-[1-(5-Ethyl-isoxazole-3-carbonyl)-2-methyl-1,2,3,4-tetrahydroquinolin-4-yl]-N-phenyl-acetamide
Cis-N-[2-Methyl-1-(2-tetrazol-1-yl-pyridine-4-carbonyl)-1,2,3,4-tetrahydroquinolin-4-yl]-N-phenyl-acetamide
Cis-N-[2-Methyl-1-(5-propyl-isoxazole-3-carbonyl)-1,2,3,4-tetrahydroquinolin-4-yl]-N-phenyl-acetamide
Cis-N-[1-(5-Isobutyl-2-methyl-2H-pyrazole-3-carbonyl)-2-methyl-1,2,3,4-tetrahydroquinolin-4-yl]-N-phenyl-acetamide
Cis-N-[1-(5-Bromo-furan-2-carbonyl)-2-methyl-1,2,3,4-tetrahydroquinolin-4-yl]-N-phenyl-acetamide
Cis-N-[2-Methyl-1-(6-phenyl-pyridine-3-carbonyl)-1,2,3,4-tetrahydroquinolin-4-yl]-N-phenyl-acetamide
Cis-N-[2-Methyl-1-(2-phenyl-pyridine-4-carbonyl)-1,2,3,4-tetrahydroquinolin-4-yl]-N-phenyl-acetamide
Cis-N-[2-Methyl-1-(quinoline-6-carbonyl)-1,2,3,4-tetrahydroquinolin-4-yl]-N-phenyl-acetamide
Cis-N-[1-(3,4-Dimethoxy-furan-2-carbonyl)-2-methyl-1,2,3,4-tetrahydroquinolin-4-yl]-N-phenyl-acetamide
Cis-N-[2-Methyl-1-(3-methyl-furan-2-carbonyl)-1,2,3,4-tetrahydroquinolin-4-yl]-N-phenyl-acetamide
Cis-N-[1-(2,5-Dimethyl-furan-3-carbonyl)-2-methyl-1,2,3,4-tetrahydroquinolin-4-yl]-N-phenyl-acetamide
Cis-N-[1-(2,4-Dimethyl-oxazole-5-carbonyl)-2-methyl-1,2,3,4-tetrahydroquinolin-4-yl]-N-phenyl-acetamide
Cis-N-[1-(5-Methoxymethyl-furan-2-carbonyl)-2-methyl-1,2,3,4-tetrahydroquinolin-4-yl]-N-phenyl-acetamide
Cis-N-[1-(5-Fluoro-pyridine-3-carbonyl)-2-methyl-1,2,3,4-tetrahydroquinolin-4-yl]-N-phenyl-acetamide
Cis-N-[2-Methyl-1-(quinoline-2-carbonyl)-1,2,3,4-tetrahydroquinolin-4-yl]-N-phenyl-acetamide
Cis-N-[2-Methyl-1-(6-methyl-pyridine-3-carbonyl)-1,2,3,4-tetrahydroquinolin-4-yl]-N-phenyl-acetamide
Cis-N-[2-Methyl-1-(quinoline-3-carbonyl)-1,2,3,4-tetrahydroquinolin-4-yl]-N-phenyl-acetamide
Cis-N-[2-Methyl-1-(1H-pyrazole-3-carbonyl)-1,2,3,4-tetrahydroquinolin-4-yl]-N-phenyl-acetamide
Cis-N-[2-Methyl-1-(2H-pyrazole-3-carbonyl)-1,2,3,4-tetrahydroquinolin-4-yl]-N-phenyl-acetamide
Cis-N-[1-(5-Isobutyl-isoxazole-3-carbonyl)-2-methyl-1,2,3,4-tetrahydroquinolin-4-yl]-N-phenyl-acetamide
Cis-N-[2-Methyl-1-(quinoline-4-carbonyl)-1,2,3,4-tetrahydroquinolin-4-yl]-N-phenyl-acetamide
Cis-N-[2-Methyl-1-(6-methyl-pyridine-2-carbonyl)-1,2,3,4-tetrahydroquinolin-4-yl]-N-phenyl-acetamide
Cis-N-[2-Methyl-1-(quinoxaline-5-carbonyl)-1,2,3,4-tetrahydroquinolin-4-yl]-N-phenyl-acetamide
Cis-N-[1-(3-Methoxy-thiophene-2-carbonyl)-2-methyl-1,2,3,4-tetrahydroquinolin-4-yl]-N-phenyl-acetamide
Cis-N-[1-(5-tert-Butyl-2-methyl-furan-3-carbonyl)-2-methyl-1,2,3,4-tetrahydroquinolin-4-yl]-N-phenyl-acetamide
Cis-N-[1-(5-Ethyl-2-methyl-2H-pyrazole-3-carbonyl)-2-methyl-1,2,3,4-tetrahydroquinolin-4-yl]-N-phenyl-acetamide
Cis-N-[2-Methyl-1-([1,2,5]thiadiazole-3-carbonyl)-1,2,3,4-tetrahydroquinolin-4-yl]-N-phenyl-acetamide
Cis-N-[2-Methyl-1-(2-methyl-5-propyl-2H-pyrazole-3-carbonyl)-1,2,3,4-tetrahydroquinolin-4-yl]-N-phenyl-acetamide
Cis-N-(1-Benzoyl-2-methyl-1,2,3,4-tetrahydroquinolin-4-yl)-N-Benzyl-acetamide;
Cis-N-Benzyl-N-[2-methyl-1-(thiophene-2-carbonyl)-1,2,3,4-tetrahydroquinolin-4-yl]-acetamide;
Trans-N-Benzyl-N-[2-methyl-1-(thiophene-2-carbonyl)-1,2,3,4-tetrahydroquinolin-4-yl]-acetamide;
Cis-N-Cyclohexyl-N-[2-methyl-1-(thiophene-2-carbonyl)-1,2,3,4-tetrahydroquinolin-4-yl]-acetamide;
Cis-N-(1-Benzoyl-6-methoxy-2-methyl-1,2,3,4-tetrahydroquinolin-4-yl)-N-phenyl-acetamide;
Cis-N-(1-Benzoyl-6-hydroxy-2-methyl-1,2,3,4-tetrahydroquinolin-4-yl)-N-phenyl-acetamide;
Cis-N-(1-Benzoyl-6-chloro-2-methyl-1,2,3,4-tetrahydroquinolin-4-yl)-N-phenyl-acetamide;
Cis-N-(1-Benzoyl-7-chloro-2-methyl-1,2,3,4-tetrahydroquinolin-4-yl)-N-phenyl-acetamide;
N-(1-Benzoyl-2-methyl-1,2,3,4-tetrahydroquinolin-4-yl)-N-prop-2-ynyl-acetamide;
Cis-N-(1-Benzoyl-2-methyl-1,2,3,4-tetrahydroquinolin-4-yl)-N-(4-methoxy-phenyl)-acetamide;
Cis-N-(1-Benzoyl-2-methyl-1,2,3,4-tetrahydroquinolin-4-yl)-N-(4-hydroxy-phenyl)-acetamide;
Cis-{4-[Acetyl-(1-benzoyl-2-methyl-1,2,3,4-tetrahydroquinolin-4-yl)-amino]-phenyl}-acetic acid ethyl ester;
Cis-N-(1-Benzoyl-2-methyl-1,2,3,4-tetrahydroquinolin-4-yl)-N-phenyl-malonamic acid methyl ester;
Cis-N-(1-Benzoyl-2-methyl-1,2,3,4-tetrahydroquinolin-4-yl)-N-phenyl-malonamic acid;
Cis-N-[2-Methyl-1-(pyridine-3-carbonyl)-1,2,3,4-tetrahydroquinolin-4-yl]-N-phenyl-acetamide;
Cis-N-(1-Benzoyl-2-methyl-1,2,3,4-tetrahydroquinolin-4-yl)-N-Cyclopropyl-acetamide;
Cis-N-Cyclopropyl-N-[2-methyl-1-(pyridine-3-carbonyl)-1,2,3,4-tetrahydroquinolin-4-yl]-acetamide
(+)-Cis-N-cyclopropyl-N-[2-methyl-1-(pyridine-3-carbonyl)-1,2,3,4-tetrahydroquinolin-4-yl]-acetamide
(−)-Cis-N-cyclopropyl-N-[2-methyl-(pyridine-3-carbonyl)-1,2,3,4-tetrahydroquinolin-4-yl]-acetamide;
Cis-N-Cyclopropyl-N-[2-methyl-1-(3-methyl-isoxazole-5-carbonyl)-1,2,3,4-tetrahydroquinolin-4-yl]-acetamide;
Cis-N-Phenyl-N-[1-(thiophene-2-carbonyl)-1,2,3,4-tetrahydroquinolin-4-yl]-acetamide;

Cis-N-(1-Benzoyl-1,2,3,4-tetrahydroquinolin-4-yl)-N-phenyl-acetamide
Cis-N-[2-Ethyl-1-(pyridine-3-carbonyl)-1,2,3,4-tetrahydroquinolin-4-yl]-N-phenyl-acetamide;
Cis-N-Ethyl-N-[2-Methyl-1-(pyridine-3-carbonyl)-1,2,3,4-tetrahydroquinolin-4-yl]-acetamide.

The following compounds are particularly preferred:
Cis-N-[2-Methyl-1-(pyridine-4-carbonyl)-1,2,3,4-tetrahydroquinolin-4-yl]-N-phenyl-acetamide;
Cis-N-[2-Methyl-1-(1-oxy-pyridine-4-carbonyl)-1,2,3,4-tetrahydroquinolin-4-yl]-N-phenyl-acetamide;
Cis-N-[1-(4-Hydroxy-benzoyl)-2-methyl-1,2,3,4-tetrahydroquinolin-4-yl]-N-phenyl-acetamide;
Cis-N-[2-Methyl-1-(4-trifluoromethyl-benzoyl)-1,2,3,4-tetrahydroquinolin-4-yl]-N-phenyl-acetamide;
Cis-N-[1-(4-Cyano-benzoyl)-2-methyl-1,2,3,4-tetrahydroquinolin-4-yl]-N-phenyl-acetamide;
Cis-N-[1-(4-Chloro-benzoyl)-2-methyl-1,2,3,4-tetrahydroquinolin-4-yl]-N-phenyl-acetamide;
4-[Cis-4-(Acetyl-phenyl-amino)-2-methyl-3,4-dihydro-2H-quinoline-1-carbonyl]-benzoic acid methyl ester;
4-[Cis-4-(Acetyl-phenyl-amino)-2-methyl-3,4-dihydro-2H-quinoline-1-carbonyl]-benzoic acid;
Cis-N-[2-Methyl-1-(3-phenyl-propionyl)-1,2,3,4-tetrahydroquinolin-4-yl]-N-phenyl-acetamide;
Cis-N-[2-Methyl-1-(5-methyl-thiophene-2-carbonyl)-1,2,3,4-tetrahydroquinolin-4-yl]-N-phenyl-acetamide;
Cis-N-[1-(Benzofurazan-5-carbonyl)-2-methyl-1,2,3,4-tetrahydroquinolin-4-yl]-N-phenyl-acetamide;
Cis-N-(2-Methyl-1-phenylacetyl-1,2,3,4-tetrahydroquinolin-4-yl)-N-phenyl-acetamide;
Cis-N-[2-Methyl-1-(pyrazine-2-carbonyl)-1,2,3,4-tetrahydroquinolin-4-yl]-N-phenyl-acetamide;
Cis-N-[1-(6-Chloro-pyridine-3-carbonyl)-2-methyl-1,2,3,4-tetrahydroquinolin-4-yl]-N-phenyl-acetamide;
Cis-N-[2-Methyl-1-(6-trifluoromethyl-pyridine-3-carbonyl)-1,2,3,4-tetrahydroquinolin-4-yl]-N-phenyl-acetamide;
Cis-N-[1-(2,6-Dimethoxy-pyridine-3-carbonyl)-2-methyl-1,2,3,4-tetrahydroquinolin-4-yl]-N-phenyl-acetamide;
Cis-N-[1-(2-Methoxy-pyridine-3-carbonyl)-2-methyl-1,2,3,4-tetrahydroquinolin-4-yl]-N-phenyl-acetamide;
Cis-N-[2-Methyl-1-(2-methylsulfanyl-pyridine-3-carbonyl)-1,2,3,4-tetrahydroquinolin-4-yl]-N-phenyl-acetamide;
Cis-N-[1-(2-Chloro-pyridine-3-carbonyl)-2-methyl-1,2,3,4-tetrahydroquinolin-4-yl]-N-phenyl-acetamide;
Cis-N-[2-Methyl-1-(5-methyl-pyrazine-2-carbonyl)-1,2,3,4-tetrahydroquinolin-4-yl]-N-phenyl-acetamide;
Cis-N-[1-(2-Chloro-6-methyl-pyridine-3-carbonyl)-2-methyl-1,2,3,4-tetrahydroquinolin-4-yl]-N-phenyl-acetamide;
Cis-N-[1-(4-Chloro-1,3-dimethyl-1H-pyrazolo[3,4-b]pyridine-3-carbonyl)-2-methyl-1,2,3,4-tetrahydroquinolin-4-yl]-N-phenyl-acetamide;
Cis-N-[2-Methyl-1-(6-(2,2,2-trifluoro-ethoxy)-pyridine-3-carbonyl)-1,2,3,4-tetrahydroquinolin-4-yl]-N-phenyl-acetamide;
Cis-N-[2-Methyl-1-(2-propylsulfanyl-pyridine-3-carbonyl)-1,2,3,4-tetrahydroquinolin-4-yl]-N-phenyl-acetamide;
Cis-N-[1-(5,6-Dichloro-pyridine-3-carbonyl)-2-methyl-1,2,3,4-tetrahydroquinolin-4-yl]-N-phenyl-acetamide;
Cis-N-[1-(2,6-Dichloro-pyridine-3-carbonyl)-2-methyl-1,2,3,4-tetrahydroquinolin-4-yl]-N-phenyl-acetamide;
Cis-N-[2-Methyl-1-(4-methyl-[1,2,3]thiadiazole-5-carbonyl)-1,2,3,4-tetrahydroquinolin-4-yl]-N-phenyl-acetamide;
Cis-N-[2-Methyl-1-(5-methyl-isoxazole-3-carbonyl)-1,2,3,4-tetrahydroquinolin-4-yl]-N-phenyl-acetamide;
Cis-N-[1-(2,5-Dimethyl-2H-pyrazole-3-carbonyl)-2-methyl-1,2,3,4-tetrahydroquinolin-4-yl]-N-phenyl-acetamide;
Cis-N-[2-Methyl-1-(1-methyl-1H-pyrrole-2-carbonyl)-1,2,3,4-tetrahydroquinolin-4-yl]-N-phenyl-acetamide;
Cis-N-[1-(Isoxazole-5-carbonyl)-2-methyl-1,2,3,4-tetrahydroquinolin-4-yl]-N-phenyl-acetamide;
Cis-N-[2-Methyl-1-(5-methyl-isoxazole-4-carbonyl)-1,2,3,4-tetrahydroquinolin-4-yl]-N-phenyl-acetamide;
Cis-N-[1-(2,4-Dimethyl-thiazole-5-carbonyl)-2-methyl-1,2,3,4-tetrahydroquinolin-4-yl]-N-phenyl-acetamide;
Cis-N-[1-(5-Chloro-thiophene-2-carbonyl)-2-methyl-1,2,3,4-tetrahydroquinolin-4-yl]-N-phenyl-acetamide;
Cis-N-[1-(1,5-Dimethyl-1H-pyrazole-3-carbonyl)-2-methyl-1,2,3,4-tetrahydroquinolin-4-yl]-N-phenyl-acetamide;
Cis-N-[2-Methyl-1-(4-methyl-isothiazole-5-carbonyl)-1,2,3,4-tetrahydroquinolin-4-yl]-N-phenyl-acetamide
Cis-5-[4-(Acetyl-phenyl-amino)-2-methyl-3,4-dihydro-2H-quinoline-1-carbonyl]-thiophene-2-carboxylic acid dimethylamide
Cis-N-[1-(4-Hydroxy-quinoline-6-carbonyl)-2-methyl-1,2,3,4-tetrahydroquinolin-4-yl]-N-phenyl-acetamide
Cis-N-[1-(4-tert-Butyl-thiazole-2-carbonyl)-2-methyl-1,2,3,4-tetrahydroquinolin-4-yl]-N-phenyl-acetamide
Cis-N-[1-(2-Ethyl-pyridine-4-carbonyl)-2-methyl-1,2,3,4-tetrahydroquinolin-4-yl]-N-phenyl-acetamide
Cis-N-[1-(3,6-Dichloro-pyridine-2-carbonyl)-2-methyl-1,2,3,4-tetrahydroquinolin-4-yl]-N-phenyl-acetamide
Cis-N-[1-(4-Chloro-2H-pyrazole-3-carbonyl)-2-methyl-1,2,3,4-tetrahydroquinolin-4-yl]-N-phenyl-acetamide
Cis-2-[4-(Acetyl-phenyl-amino)-2-methyl-3,4-dihydro-2H-quinoline-1-carbonyl]-isonicotinic acid methyl ester
Cis-N-[2-Methyl-1-(4-[1,2,4]triazol-4-yl-benzoyl)-1,2,3,4-tetrahydroquinolin-4-yl]-N-phenyl-acetamide
Cis-N-[1-(2,6-Dimethoxy-pyridine-4-carbonyl)-2-methyl-1,2,3,4-tetrahydroquinolin-4-yl]-N-phenyl-acetamide
Cis-N-[1-(5-Ethyl-isoxazole-3-carbonyl)-2-methyl-1,2,3,4-tetrahydroquinolin-4-yl]-N-phenyl-acetamide
Cis-N-[2-Methyl-1-(2-tetrazol-1-yl-pyridine-4-carbonyl)-1,2,3,4-tetrahydroquinolin-4-yl]-N-phenyl-acetamide
Cis-N-[2-Methyl-1-(5-propyl-isoxazole-3-carbonyl)-1,2,3,4-tetrahydroquinolin-4-yl]-N-phenyl-acetamide
Cis-N-[1-(5-Isobutyl-2-methyl-2H-pyrazole-3-carbonyl)-2-methyl-1,2,3,4-tetrahydroquinolin-4-yl]-N-phenyl-acetamide
Cis-N-[1-(5-Bromo-furan-2-carbonyl)-2-methyl-1,2,3,4-tetrahydroquinolin-4-yl]-N-phenyl-acetamide
Cis-N-[2-Methyl-1-(6-phenyl-pyridine-3-carbonyl)-1,2,3,4-tetrahydroquinolin-4-yl]-N-phenyl-acetamide
Cis-N-[2-Methyl-1-(2-phenyl-pyridine-4-carbonyl)-1,2,3,4-tetrahydroquinolin-4-yl]-N-phenyl-acetamide
Cis-N-[2-Methyl-1-(quinoline-6-carbonyl)-1,2,3,4-tetrahydroquinolin-4-yl]-N-phenyl-acetamide
Cis-N-[1-(3,4-Dimethoxy-furan-2-carbonyl)-2-methyl-1,2,3,4-tetrahydroquinolin-4-yl]-N-phenyl-acetamide
Cis-N-[2-Methyl-1-(3-methyl-furan-2-carbonyl)-1,2,3,4-tetrahydroquinolin-4-yl]-N-phenyl-acetamide
Cis-N-[1-(2,5-Dimethyl-furan-3-carbonyl)-2-methyl-1,2,3,4-tetrahydroquinolin-4-yl]-N-phenyl-acetamide
Cis-N-[1-(2,4-Dimethyl-oxazole-5-carbonyl)-2-methyl-1,2,3,4-tetrahydroquinolin-4-yl]-N-phenyl-acetamide
Cis-N-[1-(5-Methoxymethyl-furan-2-carbonyl)-2-methyl-1,2,3,4-tetrahydroquinolin-4-yl]-N-phenyl-acetamide Cis-N-[1-(5-Fluoro-pyridine-3-carbonyl)-2-methyl-1,2,3,4-tetrahydroquinolin-4-yl]-N-phenyl-acetamide
Cis-N-[2-Methyl-1-(quinoline-2-carbonyl)-1,2,3,4-tetrahydroquinolin-4-yl]-N-phenyl-acetamide
Cis-N-[2-Methyl-1-(6-methyl-pyridine-3-carbonyl)-1,2,3,4-tetrahydroquinolin-4-yl]-N-phenyl-acetamide
Cis-N-[2-Methyl-1-(quinoline-3-carbonyl)-1,2,3,4-tetrahydroquinolin-4-yl]-N-phenyl-acetamide
Cis-N-[2-Methyl-1-(1H-pyrazole-3-carbonyl)-1,2,3,4-tetrahydroquinolin-4-yl]-N-phenyl-acetamide
Cis-N-[2-Methyl-1-(2H-pyrazole-3-carbonyl)-1,2,3,4-tetrahydroquinolin-4-yl]-N-phenyl-acetamide
Cis-N-[1-(5-Isobutyl-isoxazole-3-carbonyl)-2-methyl-1,2,3,4-tetrahydroquinolin-4-yl]-N-phenyl-acetamide
Cis-N-[2-Methyl-1-(quinoline-4-carbonyl)-1,2,3,4-tetrahydroquinolin-4-yl]-N-phenyl-acetamide
Cis-N-[2-Methyl-1-(6-methyl-pyridine-2-carbonyl)-1,2,3,4-tetrahydroquinolin-4-yl]-N-phenyl-acetamide
Cis-N-[2-Methyl-1-(quinoxaline-5-carbonyl)-1,2,3,4-tetrahydroquinolin-4-yl]-N-phenyl-acetamide
Cis-N-[1-(3-Methoxy-thiophene-2-carbonyl)-2-methyl-1,2,3,4-tetrahydroquinolin-4-yl]-N-phenyl-acetamide
Cis-N-[1-(5-tert-Butyl-2-methyl-furan-3-carbonyl)-2-methyl-1,2,3,4-tetrahydroquinolin-4-yl]-N-phenyl-acetamide
Cis-N-[1-(5-Ethyl-2-methyl-2H-pyrazole-3-carbonyl)-2-methyl-1,2,3,4-tetrahydroquinolin-4-yl]-N-phenyl-acetamide
Cis-N-[2-Methyl-1-([1,2,5]thiadiazole-3-carbonyl)-1,2,3,4-tetrahydroquinolin-4-yl]-N-phenyl-acetamide
Cis-N-[2-Methyl-1-(2-methyl-5-propyl-2H-pyrazole-3-carbonyl)-1,2,3,4-tetrahydroquinolin-4-yl]-N-phenyl-acetamide
Cis-N-(1-Benzoyl-2-methyl-1,2,3,4-tetrahydroquinolin-4-yl)-N-Benzyl-acetamide;
Cis-N-Benzyl-N-[2-methyl-1-(thiophene-2-carbonyl)-1,2,3,4-tetrahydroquinolin-4-yl]-acetamide;
Trans-N-Benzyl-N-[2-methyl-1-(thiophene-2-carbonyl)-1,2,3,4-tetrahydroquinolin-4-yl]-acetamide;
Cis-N-Cyclohexyl-N-[2-methyl-1-(thiophene-2-carbonyl)-1,2,3,4-tetrahydroquinolin-4-yl]-acetamide;
Cis-N-(1-Benzoyl-6-methoxy-2-methyl-1,2,3,4-tetrahydroquinolin-4-yl)-N-phenyl-acetamide;
Cis-N-(1-Benzoyl-6-hydroxy-2-methyl-1,2,3,4-tetrahydroquinolin-4-yl)-N-phenyl-acetamide;
Cis-N-(1-Benzoyl-6-chloro-2-methyl-1,2,3,4-tetrahydroquinolin-4-yl)-N-phenyl-acetamide;
N-(1-Benzoyl-2-methyl-1,2,3,4-tetrahydroquinolin-4-yl)-N-prop-2-ynyl-acetamide;
Cis-N-(1-Benzoyl-2-methyl-1,2,3,4-tetrahydroquinolin-4-yl)-N-(4-methoxy-phenyl)-acetamide;
Cis-N-(1-Benzoyl-2-methyl-1,2,3,4-tetrahydroquinolin-4-yl)-N-(4-hydroxy-phenyl)-acetamide;
Cis-{4-[Acetyl-(1-benzoyl-2-methyl-1,2,3,4-tetrahydroquinolin-4-yl)-amino]-phenyl}-acetic acid ethyl ester;
Cis-N-(1-Benzoyl-2-methyl-1,2,3,4-tetrahydroquinolin-4-yl)-N-phenyl-malonamic acid methyl ester;
Cis-N-(1-Benzoyl-2-methyl-1,2,3,4-tetrahydroquinolin-4-yl)-N-phenyl-malonamic acid;
Cis-N-[2-Methyl-1-(pyridine-3-carbonyl)-1,2,3,4-tetrahydroquinolin-4-yl]-N-phenyl-acetamide;
Cis-N-(1-Benzoyl-2-methyl-1,2,3,4-tetrahydroquinolin-4-yl)-N-Cyclopropyl-acetamide;
Cis-N-Cyclopropyl-N-[2-methyl-1-(pyridine-3-carbonyl)-1,2,3,4-tetrahydroquinolin-4-yl]-acetamide
(+)-Cis-N-cyclopropyl-N-[2-methyl-1-(pyridine-3-carbonyl)-1,2,3,4-tetrahydroquinolin-4-yl]-acetamide (−)-Cis-N-cyclopropyl-N-[2-methyl-1 (pyridine-3-carbonyl)-1,2,3,4-tetrahydroquinolin-4-yl]-acetamide;
Cis-N-Cyclopropyl-N-[2-methyl-1-(3-methyl-isoxazole-5-carbonyl)-1,2,3,4-tetrahydroquinolin-4-yl]-acetamide;
Cis-N-Phenyl-N-[1-(thiophene-2-carbonyl)-1,2,3,4-tetrahydroquinolin-4-yl]-acetamide;
Cis-N-(1-Benzoyl-1,2,3,4-tetrahydroquinolin-4-yl)-N-phenyl-acetamide
Cis-N-[2-Ethyl-1-(pyridine-3-carbonyl)-1,2,3,4-tetrahydroquinolin-4-yl]-N-phenyl-acetamide;
Cis-N-Ethyl-N-[2-Methyl-1-(pyridine-3-carbonyl)-1,2,3,4-tetrahydroquinolin-yl]-acetamide;

The above compounds of configuration $C^{*1}(R)$—$C^{*2}(S)$, $C^{*1}(S)$—$C^{*2}(R)$ or mixture thereof are particularly preferred:

Most preferred compounds are:
Cis-N-[2-Methyl-1-(pyridine-4-carbonyl)-1,2,3,4-tetrahydroquinolin-4-yl]-N-phenyl-acetamide;
Cis-N-[1-(4-Hydroxy-benzoyl)-2-methyl-1,2,3,4-tetrahydroquinolin-4-yl]-N-phenyl-acetamide;
Cis-N-[2-Methyl-1-(4-trifluoromethyl-benzoyl)-1,2,3,4-tetrahydroquinolin-4-yl]-N-phenyl-acetamide;
Cis-N-[1-(4-Chloro-benzoyl)-2-methyl-1,2,3,4-tetrahydroquinolin-4-yl]-N-phenyl-acetamide;
Cis-N-[2-Methyl-1-(5-methyl-thiophene-2-carbonyl)-1,2,3,4-tetrahydroquinolin-4-yl]-N-phenyl-acetamide;
Cis-N-[1-(Benzofurazan-5-carbonyl)-2-methyl-1,2,3,4-tetrahydroquinolin-4-yl]-N-phenyl-acetamide;
Cis-N-[1-(6-Chloro-pyridine-3-carbonyl)-2-methyl-1,2,3,4-tetrahydroquinolin-4-yl]-N-phenyl-acetamide;
Cis-N-[2-Methyl-1-(6-trifluoromethyl-pyridine-3-carbonyl)-1,2,3,4-tetrahydroquinolin-4-yl]-N-phenyl-acetamide;
Cis-N-[1-(2,6-Dimethoxy-pyridine-3-carbonyl)-2-methyl-1,2,3,4-tetrahydroquinolin-4-yl]-N-phenyl-acetamide;
Cis-N-[2-Methyl-1-(6-(2,2,2-trifluoro-ethoxy)-pyridine-3-carbonyl)-1,2,3,4-tetrahydroquinolin-4-yl]-N-phenyl-acetamide;
Cis-N-[2-Methyl-1-(5-methyl-isoxazole-3-carbonyl)-1,2,3,4-tetrahydroquinolin-4-yl]-N-phenyl-acetamide;
Cis-N-[1-(Isoxazole-5-carbonyl)-2-methyl-1,2,3,4-tetrahydroquinolin-4-yl]-N-phenyl-acetamide;
Cis-N-[1-(5-Chloro-thiophene-2-carbonyl)-2-methyl-1,2,3,4-tetrahydroquinolin-4-yl]-N-phenyl-acetamide;
Cis-N-[2-Methyl-1-(5-propyl-isoxazole-3-carbonyl)-1,2,3,4-tetrahydroquinolin-4-yl]-N-phenyl-acetamide
Cis-N-[2-Methyl-1-(quinoline-6-carbonyl)-1,2,3,4-tetrahydroquinolin-4-yl]-N-phenyl-acetamide
Cis-N-[1-(5-Methoxymethyl-furan-2-carbonyl)-2-methyl-1,2,3,4-tetrahydroquinolin-4-yl]-N-phenyl-acetamide
Cis-N-[1-(5-Isobutyl-isoxazole-3-carbonyl)-2-methyl-1,2,3,4-tetrahydroquinolin-4-yl]-N-phenyl-acetamide
Cis-N-[1-(3-Methoxy-thiophene-2-carbonyl)-2-methyl-1,2,3,4-tetrahydroquinolin-4-yl]-N-phenyl-acetamide
Cis-N-[2-Methyl-1-([1,2,5]thiadiazole-3-carbonyl)-1,2,3,4-tetrahydroquinolin-4-yl]-N-phenyl-acetamide
Cis-N-Benzyl-N-[2-methyl-1-(thiophene-2-carbonyl)-1,2,3,4-tetrahydroquinolin-4-yl]-acetamide;
Cis-N-(1-Benzoyl-6-hydroxy-2-methyl-1,2,3,4-tetrahydroquinolin-4-yl)-N-phenyl-acetamide;
Cis-N-(1-Benzoyl-6-chloro-2-methyl-1,2,3,4-tetrahydroquinolin-4-yl)-N-phenyl-acetamide;
N-(1-Benzoyl-2-methyl-1,2,3,4-tetrahydroquinolin-4-yl)-N-prop-2-ynyl-acetamide;
Cis-N-(1-Benzoyl-2-methyl-1,2,3,4-tetrahydroquinolin-4-yl)-N-(4-methoxy-phenyl)-acetamide;

Cis-N-(1-Benzoyl-2-methyl-1,2,3,4-tetrahydroquinolin-4-yl)-N-(4-hydroxy-phenyl)-acetamide;
Cis-{4-[Acetyl-(1-benzoyl-2-methyl-1,2,3,4-tetrahydroquinolin-4-yl)-amino]-phenyl}-acetic acid ethyl ester;
Cis-N-(1-Benzoyl-2-methyl-1,2,3,4-tetrahydroquinolin-4-yl)-N-phenyl-malonamic acid methyl ester;
Cis-N-[2-Methyl-1-(pyridine-3-carbonyl)-1,2,3,4-tetrahydroquinolin-4-yl]-N-phenyl-acetamide;
Cis-N-(1-Benzoyl-2-methyl-1,2,3,4-tetrahydroquinolin-4-yl)-N-Cyclopropyl-acetamide;
Cis-N-Cyclopropyl-N-[2-methyl-1-(pyridine-3-carbonyl)-1,2,3,4-tetrahydroquinolin-4-yl]-acetamide
(+)-Cis-N-cyclopropyl-N-[2-methyl-1-(pyridine-3-carbonyl)-1,2,3,4-tetrahydroquinolin-4-yl]-acetamide
(−)-Cis-N-cyclopropyl-N-[2-methyl-1 (pyridine-3-carbonyl)-1,2,3,4-tetrahydroquinolin-4-yl]-acetamide;
Cis-N-Cyclopropyl-N-[2-methyl-1-(3-methyl-isoxazole-5-carbonyl)-1,2,3,4-tetrahydroquinolin-4-yl]-acetamide;
Cis-N-Phenyl-N-[1-(thiophene-2-carbonyl)-1,2,3,4-tetrahydroquinolin-4-yl]-acetamide, and,
Cis-N-[2-Ethyl-1-(pyridine-3-carbonyl)-1,2,3,4-tetrahydroquinolin-4-yl]-N-phenyl-acetamide.

The invention further relates to the above compounds or groups of compounds as medicaments. The invention further relates to the above compounds or groups of compounds as CRTH2 antagonists.

General Process for the Preparation of Compounds of the Invention

The invention also relates to a process for manufacturing a compound of formula (I),

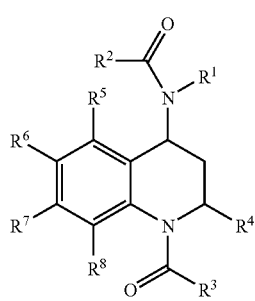

(I)

wherein $R^1$, $R^2$, $R^3$, $R^5$, $R^6$, $R^7$ and $R^8$ are as defined in the summary of the invention and $R^4$ is $(C_1-C_4)$alkyl, said process comprising the following steps:

(1) reacting a compound of formula (1a),

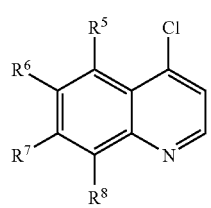

(1a)

wherein $R^5$, $R^6$, $R^7$ and $R^8$ are as defined in the summary of the invention, with sodium methoxide, in the presence of a solvent such as methanol, to give the compound of formula (1b),

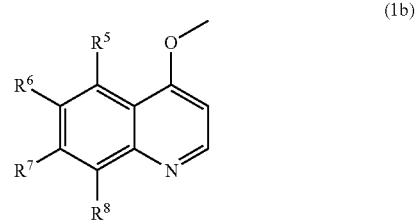

(1b)

in which $R^5$, $R^6$, $R^7$ and $R^8$ are as defined above;

(2) reacting said compound of formula (1b) with a compound of formula $R^4$—MgCl, wherein $R^4$ is $(C_1-C_4)$alkyl in an anhydrous ether such as tetrahydrofuran and then with benzylchloroformate, to give the compound of formula (1c),

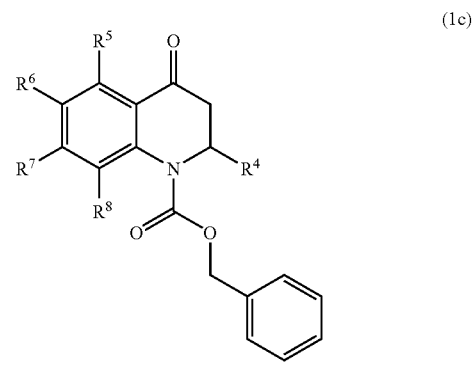

(1c)

in which $R^4$, $R^5$, $R^6$, $R^7$ and $R^8$ are as defined above;

(3) reacting said compound of formula (1c) with a compound of formula $R^1$—$NH_2$, wherein $R^1$ is as defined in the summary of the invention, in the presence of a base and of $TiCl_4$ to give the compound of formula (1d),

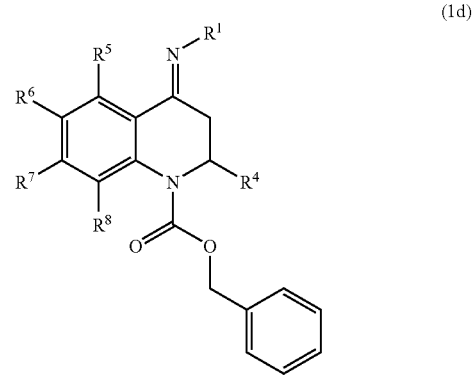

(1d)

in which $R^1$, $R^4$, $R^5$, $R^6$, $R^7$ and $R^8$ are as defined above;

(4) reducing said compound of formula (1d), using for example NaBH$_4$ and MeOH in the presence of acetic acid, to give the compound of formula (1e),

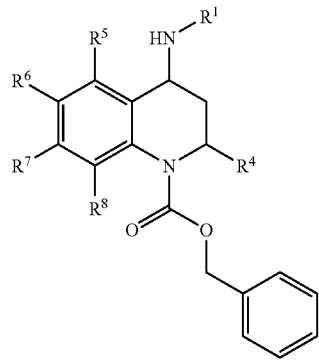
(1e)

in which R$^1$, R$^4$, R$^5$, R$^6$, R$^7$ and R$^8$ are as defined above;

(5) reacting said compound of formula (1e) with a compound of formula R$^2$COCl, wherein R$^2$ is as defined in the summary of the invention, in the presence of a base, to give the compound of formula (1f),

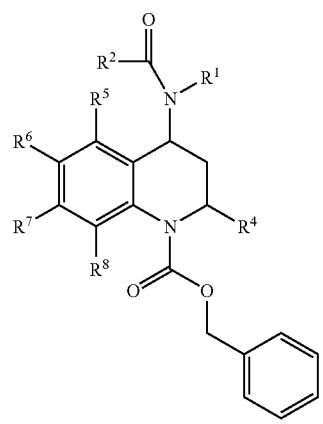
(1f)

in which R$^1$, R$^2$, R$^4$, R$^5$, R$^6$, R$^7$ and R$^8$ are as defined above;

(6) deprotecting said compound of formula (1f) by hydrogenolysis, using for example ammonium formate catalyzed by palladium on charcoal, to give the compound of formula (1g)

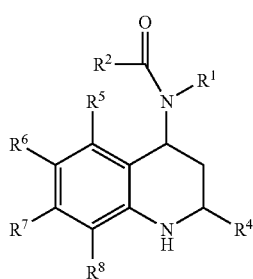
(1g)

in which R$^1$, R$^2$, R$^4$, R$^5$, R$^6$, R$^7$ and R$^8$ are as defined above;

(7) reacting said compound of formula (1g) with R$^3$COCl, wherein R$^3$ is as defined in the summary of the invention, in the presence of a base, to give a compound of formula (I) wherein R$^1$, R$^2$, R$^4$, R$^5$, R$^6$, R$^7$ and R are as defined above R$^4$ is (C$_1$–C$_4$)alkyl, (8) isolating said compound of formula (I), or, (9) separating compounds of formula (Ia) and (Ib)

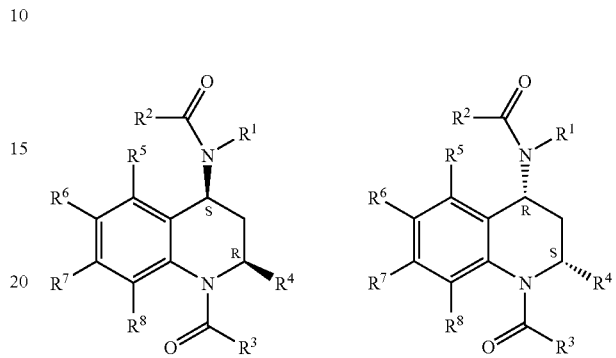

from compounds of formula (Ic) and (Id)

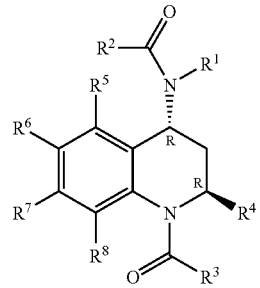
(Ic)

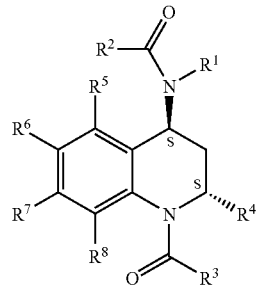
(Id)

and, isolating said compounds of formula (Ia) and (Ib) and compounds of formula (Ic) and (Id), or further separating compounds of formula (Ia) and (Ib) and compounds of formula (Ic) and (Id) to obtain four separated diastereoisomers and isolating them.

The invention also relates to a process for manufacturing a compound of formula (Ia) or (Ib) or a mixture thereof,

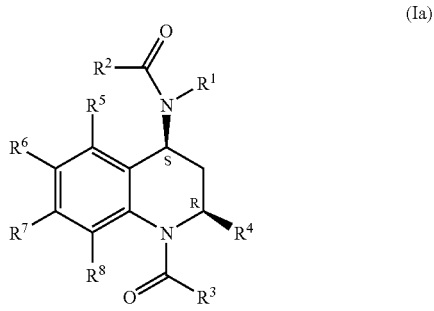
(Ia)

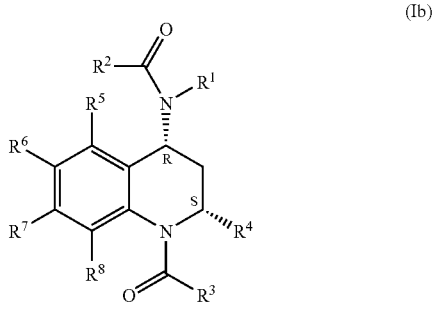
(Ib)

wherein $R^1$, $R^2$, $R^3$, $R^5$, $R^6$, $R^7$ and $R^8$ and $R^4$ is $(C_1-C_4)$ alkyl, said process being characterized in that a compound of formula (1d)

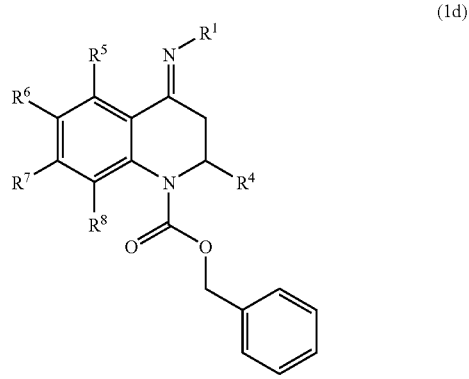
(1d)

wherein $R^1$, $R^5$, $R^6$, $R^7$ and $R^8$ are as defined in the summary of the invention and $R^4$ is $(C_1-C_4)$alkyl, is reacted with a mineral borohydride such as sodium triacetoxy borohydride in acetic acid, to give a compound cis-(1e) of formula

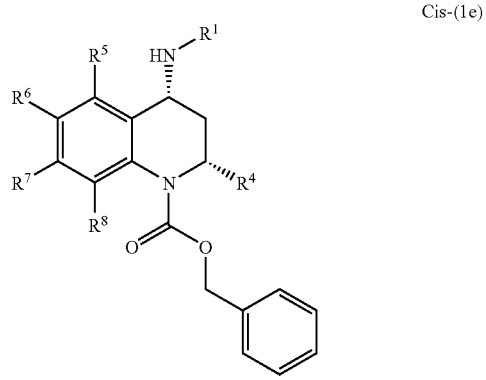
Cis-(1e)

wherein $R^1$, $R^4$, $R^5$, $R^6$, $R^7$ and $R^8$ are as defined above.

Steps 5, 6 and 7 are then performed as disclosed in scheme 1 to give a mixture of compound of formula (Ia) and (Ib) wherein $R^1$, $R^2$, $R^3$, $R^4$, $R^5$, $R^6$, $R^7$ and $R^8$ are as defined above. Optionally, compounds of formula (Ia) and (Ib) may be separated and isolated.

The invention also relates to a process for manufacturing a compound of formula (Ia) or (Ib) or a mixture thereof,

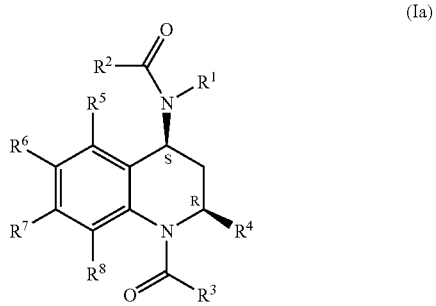
(Ia)

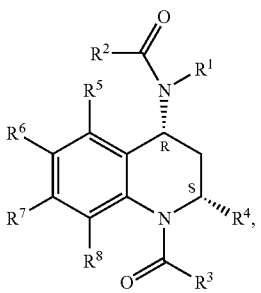
(Ib)

said process being comprising the following steps,
(1) reacting a compound of formula (3a)

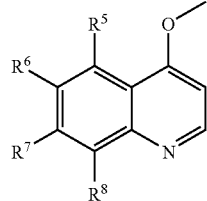

(3a)

wherein $R^5$, $R^6$, $R^7$ and $R^8$ are as defined in the summary of the invention, with a compound of formula $R^4$—MgCl, wherein $R^4$ is $(C_1-C_4)$alkyl in an anhydrous ether such as tetrahydrofuran, and then with, a compound of formula $R^3$—COCl, to give a compound of formula (3b)

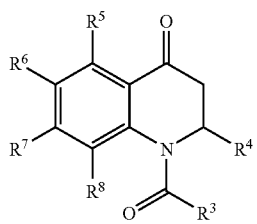

(3b)

wherein $R^3$, $R^4$, $R^5$, $R^6$, $R^7$ and $R^8$ are as defined above;

(2) reacting said compound of formula (3b) with a compound of formula $R^1$—$NH_2$, wherein $R^1$ is as defined in the summary of the invention, in the presence of a base to give a compound of formula (3c),

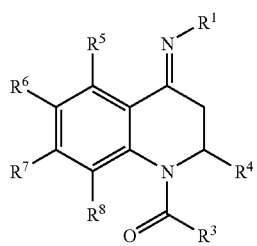

(3c)

wherein $R^1$, $R^3$, $R^4$, $R^5$, $R^6$, $R^7$ and $R^8$ are as defined above;

(3) reducing said compound of formula (3c) using for example a mineral borohydride such as sodium triacetoxy borohydride in acetic acid to give a compound of formula (3d),

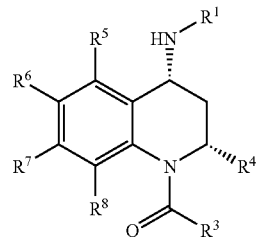

(3d)

wherein $R^1$, $R^3$, $R^4$, $R^5$, $R^6$, $R^7$ and $R^8$ are as defined above;

(4) reacting said compound of formula (3d) with a compound of formula $R^2$COCl, wherein $R^2$ is as defined in the summary of the invention, in the presence of a base, to give a mixture of compounds of formula (Ia) and (Ib) wherein $R^1$, $R^2$, $R^3$, $R^4$, $R^5$, $R^6$, $R^7$ and $R^8$ are as defined above;

(5) isolating said mixture, or (6) separating and isolating said compounds of formula (Ia) and (Ib).

The invention also relates to a process for manufacturing a compound of formula (Ia) or (Ib) or mixture thereof,

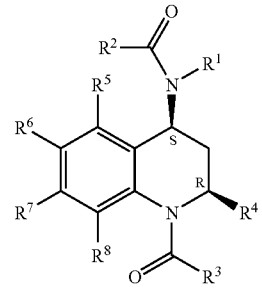

(Ia)

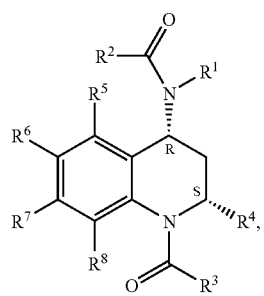

(Ib)

said process being comprising the following steps,
(1) reacting a compound of formula (4a)

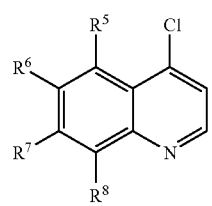

(4a)

with a compound of formula $R^1$—$NH_2$, wherein $R^1$ is as defined in the summary of the invention, to give the compound of formula (4b),

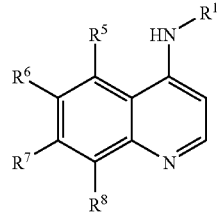

(4b)

in which $R^1$, $R^5$, $R^6$, $R^7$ and $R^8$ are as defined above;

(2) reacting said compound of formula (4b), with a compound of formula $R^2COCl$, wherein $R^2$ is as defined in the summary of the invention, in the presence of a base, to give the compound of formula (4c),

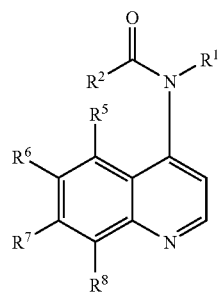

(4c)

in which $R^1$, $R^2$, $R^5$, $R^6$, $R^7$ and $R^8$ are as defined above;

(3) reacting said compound of formula (4c) with benzyl-halogen in a solvent such as acetone to give the compound of formula (4d),

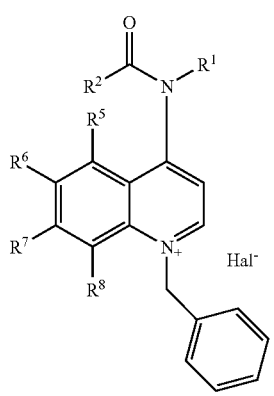

(4d)

in which $R^1$, $R^2$, $R^5$, $R^6$, $R^7$ and $R^8$ are as defined above;

(4) optionally, reacting said compound of formula (4d) with a compound of formula $R^4$—MgCl, wherein $R^4$ is $(C_1-C_4)$alkyl in an anhydrous ether such as tetrahydrofuran to give the compound of formula (4e),

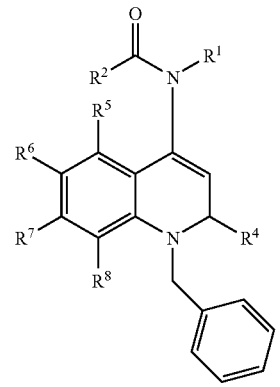

(4e)

in which $R^1$, $R^2$, $R^5$, $R^6$, $R^7$ and $R^8$ are as defined above and $R^4$ is $(C_1-C_4)$ alkyl;

(5) reducing said compound of formula (4d) or (4e), for example by hydrogenation in MeOH in presence (R,R)-(−)-1,2-bis[(o-methoxyphenyl)(phenyl)phosphino]ethane (1,5-cyclooctadiene)rhodium (I) tetrafluoroborate or $NiCl_2/NaBH_4$, to give a compound of formula (4f)

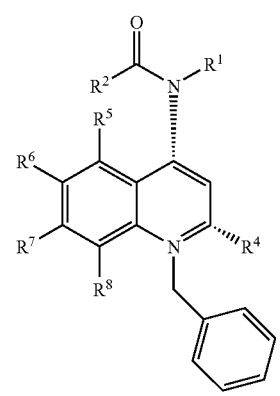

(4f)

in which $R^1$, $R^2$, $R^5$, $R^6$, $R^7$ and $R^8$ are as defined above and $R^4$ is hydrogen or $(C_1-C_4)$ alkyl;

(6) deprotecting said compound of formula (4f) by hydrogenolysis using for example ammonium formate catalysed by palladium on charcoal, to give a compound of formula (4g)

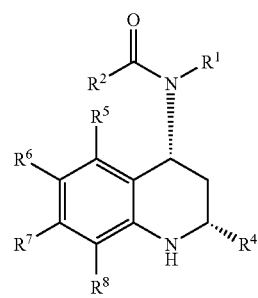

(4g)

in which R $R^2$, $R^4$, $R^5$, $R^6$, $R^7$ and $R^8$ are as defined above;

(7) reacting said compound of formula (4g) with R³COCl, wherein R³ is as defined in the summary of the invention, in the presence of a base, to give a mixture compounds of formula (Ia) and (Ib) wherein R¹, R², R³, R⁴, R⁵, R⁶, R⁷ and R⁸ are as defined above;

(8) isolating said compounds of formula (Ia) and (Ib), or, (9) separating compounds of formula (Ia) and (Ib) and isolating them.

Depending of their substitution, compounds of formula (I) may have further chiral centers. Optical isomers due to said further chiral centers are included within the scope of the invention.

The compounds utilized in the invention include pharmaceutically acceptable derivatives of compounds of formula (I) such as solvates, hydrates, pharmaceutically acceptable salts and polymorphs (different crystalline lattice descriptors).

Pharmaceutically acceptable salts of a compound of formula (I) include salts having a basic part and salts having an acidic part.

The expression pharmaceutically acceptable salt of a compound of formula (I) having a basic part should be understood to refer to the addition salts of the compounds of formula (I) which may be formed from non-toxic inorganic or organic acids such as, for example, hydrobromic, hydrochloric, sulfuric, phosphoric, nitric, acetic, succinic, tartaric, citric, maleic, hydroxymaleic, benzoic, fumaric and toluenesulfonic acid salts, and the like. The various quaternary ammonium salts of the derivatives (I) are also included in this category of compounds of the invention. In addition, the expression pharmaceutically acceptable salt of a compound of formula (I) having an acidic part is understood to refer to the usual salts of the compounds of formula (I) which may be formed from non-toxic inorganic or organic bases such as, for example, the hydroxides of alkali metals and alkaline-earth metals (sodium, potassium, magnesium and calcium), amines (dibenzylethylenediamine, trimethylamine, piperidine, pyrrolidine, benzylamine and the like) or alternatively quaternary ammonium hydroxides such as tetramethylammonium hydroxide. (See also "Pharmaceutical salts" by Berge S. M. et al. (1997) *J. Pharm. Sci.* 66: 1–19, which is incorporated herein by reference.).

Use of a prodrug of a compound of the invention such as it would occur to one skilled in the art (see Bundgaard, et al., *Acta Pharm. Suec.*, 1987; 24: 233–246), is also contemplated.

Pharmaceutical Compositions

The products of the invention are administered in the form of compositions, which are appropriate for the nature, and severity of the complaint to be treated. The daily dose in humans is usually between 1 mg and 1 g of product, which may be taken in one or more individual doses. The compositions are prepared in forms which are compatible with the intended route of administration, such as, for example, tablets, coated tablets, capsules, mouthwashes, aerosols, powders for inhalation, suppositories, enemas, foams (such as rectal foams), gels or suspensions. These compositions are prepared by methods which are familiar to those skilled in the art and comprise from 0.5 to 60% by weight of active principle (compound of the invention) and 40 to 99.5% by weight of a pharmaceutical vehicle or carrier which is appropriate and compatible with the active principle and the physical form of the intended composition.

Solid form preparations include powders, tablets, dispersible granules, capsules, cachets, and suppositories. A solid carrier can be one or more substances which may also act as diluents, flavouring agents, solubilizers, lubricants, suspending agents, binders, or tablet disintegrating agents; it can also be an encapsulating material. In powders, the carrier is a finely divided solid, which is in a mixture with the finely divided active component. In tablets, the active component is mixed with the carrier having the necessary binding properties in suitable proportions and compacted in the shape and size desired. The powders, tablets, cachets or encapsulated forms for capsules preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration. The drug may be delivered as a spray (either in a pressurized container fitted with an appropriate valve or in a non-pressurized container fitted with a metering valve).

Liquid form preparations include solutions, suspensions, and emulsions.

Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify. Enemas are obtained according to known procedures to prepare solutions adapted for rectal administration. Foams are prepared according to known methods (these foams can notably be similar to those used to administer a drug such as 5-ASA for treating rectocolite).

Preferably the pharmaceutical preparation is in unit dosage form. In such form, the preparation is divided into unit doses containing appropriate quantities of drug. The unit dosage form can be a packaged preparation, the package containing discrete quantities of the preparation, for example, packaged tablets, capsules, and powders in vials or ampoules. The unit dosage form can also be a capsule, cachet, or tablet itself, or it can be the appropriate number of any of these packaged forms.

Use

The compounds of the invention are CRTH2 antagonists, preferably selective CRTH2 antagonists. These compounds have low $IC_{50}$ values, typically at most 10 μM, preferably below 1 μM, more preferably below 500 nM.

Compounds of the invention can be used in the prevention and the treatment of disease that can be treated by a CRTH2 antagonist such as Th2 cells-related diseases, eosinophils-related diseases and basophils-related diseases. Preferably, the compounds of the invention can be used for the prevention or the treatment of diseases involving inflammatory components including, without limitation, inflammatory disorders such as rheumatoid arthritis, osteoarthritis, atherosclerosis, Crohn's disease, colitis ulcerosa, inflammatory bowel disease; disorders of the skin including psoriasis, eczema, erythema, pruritis, and acne; systemic lupus erythematous, chronic obstructive pulmonary disease, angioedema, stroke, and any disease marked by reperfusion injury, graft rejection, and autoimmune diseases, allergic diseases, such as allergic asthma, atopic dermatitis, and allergic rhinitis.

The invention finally relates to a method for the treatment of the above-mentioned diseases comprising administering to a mammal, particularly a human, in need thereof an effective amount of compound of the invention.

Processes for Synthesizing Compounds of the Invention

Protocol A

Protocol A is useful for the preparation of compounds of formula (I) wherein $R^4$ is ($C_1$–$C_4$) alkyl.

Scheme 1 illustrates the preparation of cis isomers of compounds of formula (I) wherein $R^4$ is ($C_1$–$C_4$) alkyl.

Scheme 1

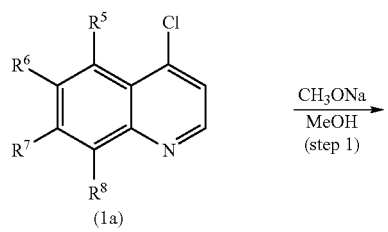

(1a)

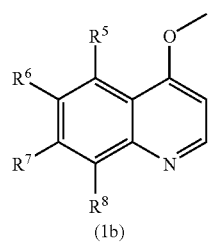

(1b)

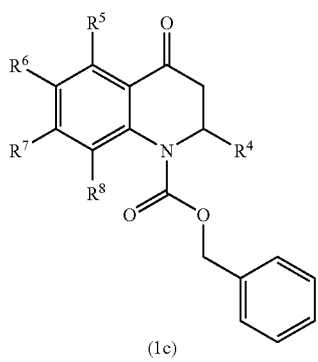

(1c)

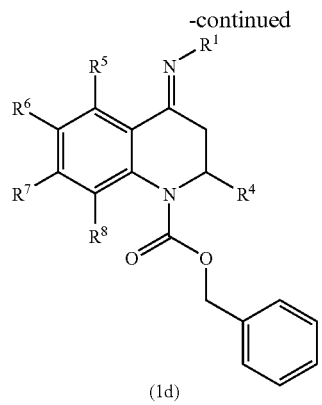

(1d)

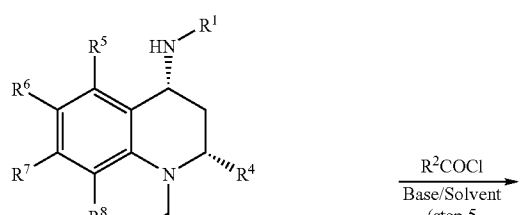

Cis-(1e)

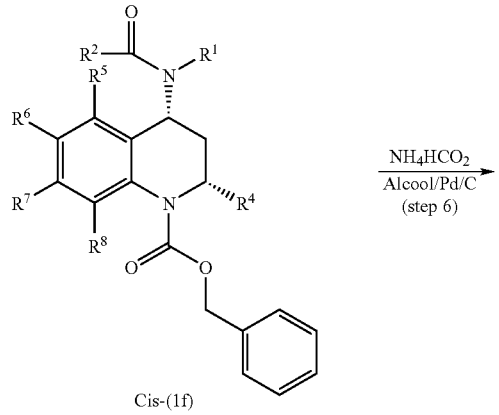

Cis-(1f)

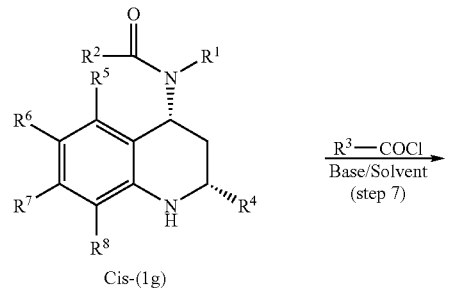

Cis-(1g)

-continued

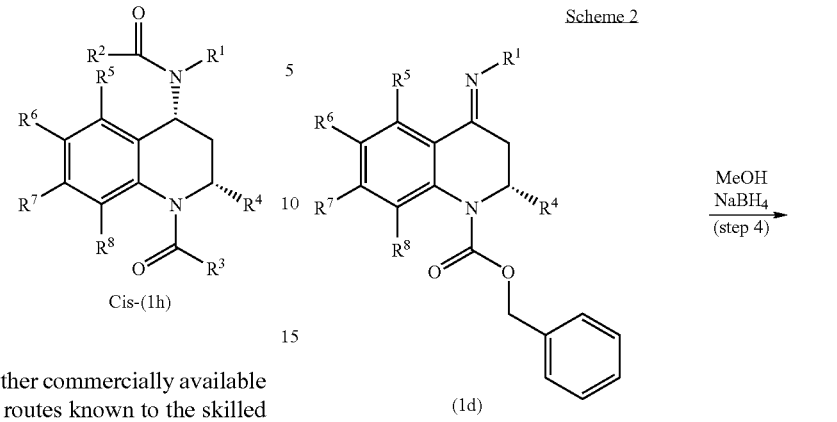

Cis-(1h)

The starting compounds are either commercially available or can be prepared according to routes known to the skilled person.

In step 1, compound (1a), where $R^5$, $R^6$, $R^7$ and $R^8$ are as defined in the summary of the invention, is reacted with sodium methoxide (preferably 5–10 eq) in methanol under reflux to form the desired methoxy quinoline.

In step 2, compound (1b) is reacted with an excess of a solution of $R^4$-magnesium chloride in anhydrous ether (for example tetrahydrofuran) at low temperature, preferably between 0 and −78° C., and then treated with an excess of benzyl chloroformate in the same condition of temperature to give compound (1c).

In step 3, compound (1c) is reacted with an amine (for example aniline), a solution of titanium chloride (preferably 1 to 1.1 eq) in toluene, a base (preferably 4 to 8 eq) such as triethyl amine, in a chlorinated solvent such as dichloromethane at a temperature below 0° C. to give compound (1d).

In step 4, compound (1d) is reacted with an excess of sodium triacetoxy borohydride in acetic acid at room temperature to give the desired amine (cis).

In step 5, compound cis-(1e) is acylated with an acyl chloride of formula $R^2$—COCl (preferably 5–30 eq) in a solvent such as dioxane or DMF and a base such as diisopropylethyl amine under reflux to give compound cis-(1f).

In step 6, compound cis-(1f) is deprotected by hydrogenolysis (for example ammonium formate catalyzed by palladium on charcoal) in an alcool, such as ethanol, under reflux, to form compound cis-(1g).

In step 7, compound cis-(1g) is reacted with an acyl chloride (commercially available or prepared from the corresponding acid) of formula $R^3$—COCl, in a solvent such as dioxane, THF or DMF, and a base in solution or its solid supported form, such as diisopropylethyl amine, at room temperature to give a compound of formula (I) wherein $R^4$ is $(C^1–C^4$ alkyl).

Optionally, cis-isomers of configuration $C^{*1}(R)$—$C^{*2}(S)$ or $C^{*1}(S)$—$C^{*2}(R)$ can be separated by using methods known to the skilled man, such as flash chromatography.

Scheme 2 illustrates the preparation of a mixture of diastereoisomers of compounds of formula (I) wherein $R^4$ is $(C_1–C_4)$ alkyl, starting from compound (1d) of scheme 1.

Scheme 2

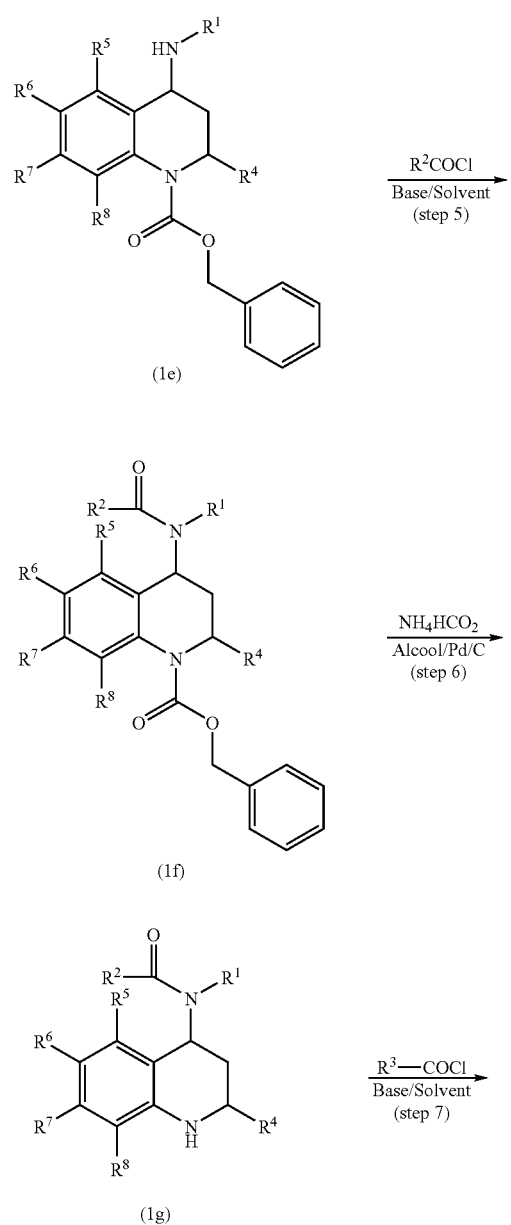

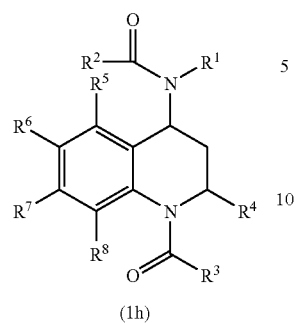

(1h)

Compound 1h is a mixture of 4 diastereoisomers, containing two isomers with a cis configuration and two isomers with a trans configuration. Cis isomers and trans isomers can be separated using methods known to the skilled man, such as flash chromatography.

Protocole B

Protocol B is an alternative process for the preparation of compounds of formula (I) wherein $R^4$ is ($C_1$–$C_4$) alkyl. Scheme 3 illustrates the preparation of cis-isomers of compounds of formula (I).

Scheme 3

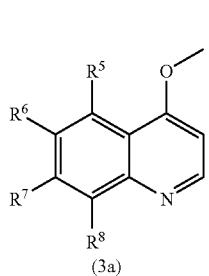 

(3a)

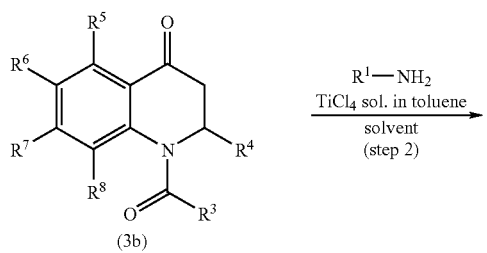

(3b)

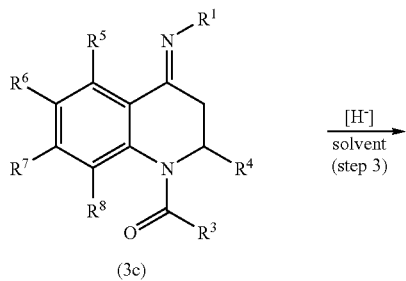 

(3c)

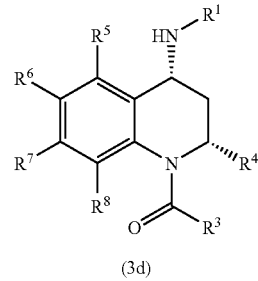 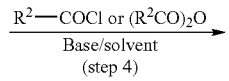

(3d)

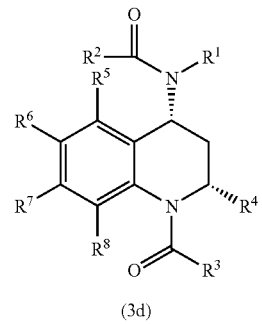

(3d)

Compound (3a) is obtained according to step 1 of scheme 1.

In step 1, compound (3b) is reacted with a solution of $R^4$—MgCl (preferably 5 to 10 eq) in anhydrous ether such as tetrahydrofuran at low temperature, preferably between 0° C. and −78° C., and then treated with $R^3$—COCl (preferably 5 to 10 eq) in the same condition of temperature to form compound (3b).

In step 2, compound (3b) is reacted with a compound of formula $R^1$—$NH_2$, (preferably 2 to 3 eq.), titanium chloride (preferably 1 eq) in solution in toluene, TEA (preferably 4 to 8 eq.) in a chlorinated solvent, such as dichloromethane or dichloroethane at a temperature below 0° C. and stirred over night at a temperature preferably comprised between room temperature and 80° C., to give the imine derivative (3c).

In step 3, compound (3c) is reduced with a mineral borohydride (preferably 5 to 6 eq) such as sodium triacetoxyborohydride, in acetic acid. The reaction is carried out at room temperature to form the amine (3d).

In step 4, compound (3d) is acylated with $R^2$—COCl (preferably 1 to 6 eq), in a solvent such as dioxane or DMF, and a base such diisopropylethyl amine (preferably 1 to 3 eq) at room temperature to give the desired compound of formula (I).

A mixture of diastereoisomers of compounds of formula (I) can be obtained by replacing step 3 of scheme 3 by step 4 of scheme 2. The trans isomers can then be obtained using classical methods of diastereoisomers separation.

Protocole C

Protocol C is an alternative process for the preparation of compounds of formula (I) wherein $R^4$ is ($C_1$–$C_4$) alkyl or hydrogen.

Scheme 4 illustrates the preparation of cis isomers of compounds of formula (I) wherein $R^4$ is H or ($C_1$–$C_4$) alkyl.

Scheme 4

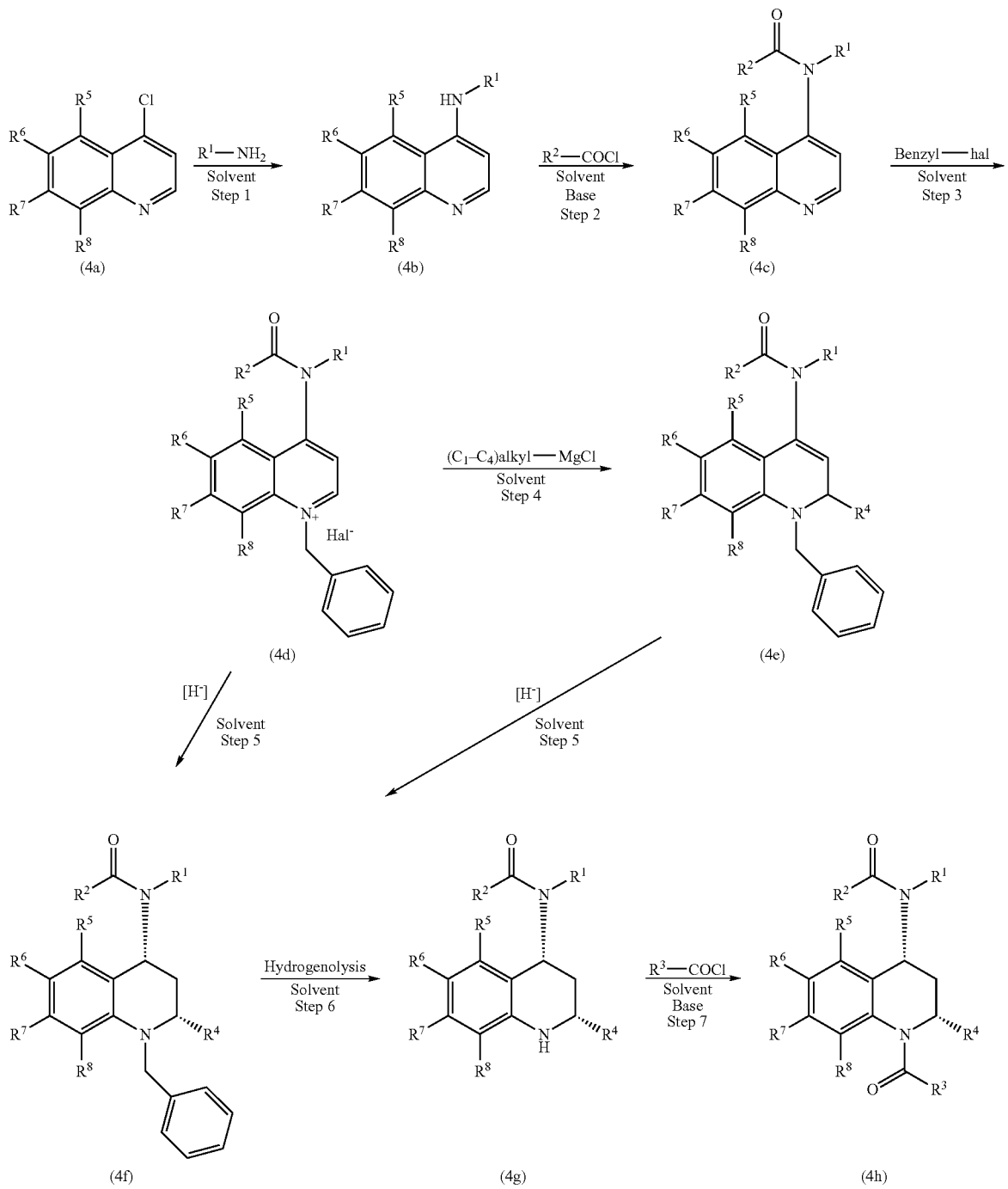

In step 1, compounds (4a) is reacted with a compound of formula $R^1$—$NH_2$, optionally in a solvent such as acetonitrile, preferably at a temperature between 150° C. to 200° C. for 0.5 to 1 hour, to form compound (4b).

In step 2, compound (4b) is acylated with an acid chloride of formula $R^2$—COCl (preferably 5 to 10 eq), in an appropriate solvent such as pyridine or dioxane with or without N-ethyl-N,N-diisopropylamine, preferably at a temperature of between 50 and 130° C. to form compound (4c).

In step 3, compound (4c) is reacted with benzyle-halogene, said halogen being preferably Cl or Br, in a solvent such as acetone to obtain compound of formula (4d).

Step 4 is performed to obtain compounds of formula (I) in which $R^4$ is $(C_1-C_4)$ alkyl. Step 4 is as disclosed in Scheme 1. Alternatively, to obtain compounds of formula (I) where $R^4$ is H, step 5 is performed directly after step 3.

In step 5, compound (4d) (from step 3) or compound (4e) (from step 4) is reduced into compound (4f). The reduction is preferably carried out using NiCl$_2$/NaBH$_4$ in MeOH/THF or by hydrogenation in MeOH in presence (R,R)-(−)-1,2-bis[(o-methoxyphenyl)(phenyl)phosphino]ethane(1,5-cyclooctadiene)rhodium (I) tetrafluoroborate.

In step 6, compound (4f) is deprotected by hydrogenolysis (for example ammonium formate catalysed by palladium on charcoal) in an alcool, such as ethanol, under reflux, to form compound (4g).

In step 7, compound (4g) acylated with a compound of formula R$^3$—COCl (preferably 5 to 10 eq), in an appropriate solvent such as pyridine or dioxane with or without N-ethyl-N,N-diisopropylamine, preferably at a temperature of between 50 and 130° C. to form compound (4h).

SYNTHESIS EXAMPLES

The following examples illustrate, without limiting it, the synthesis of particularly active compounds of formula (I) according to the invention.

$^1$H-NMR spectra were recorded at 400 MHz. The residual solvent peak, usually chloroform ($\delta_H$ 7.27 ppm) or DMSO ($\delta_H$ 2.5 ppm) was used as internal shift reference. Analytical HPLC was run on a DIONEX Summit equipped with a diode array detector, using a Kromasil C-18 reversed-phase column and eluting with the following general system: acetonitrile with 0.1% v/v of acid formic in water with 0.1% v/v of acid formic (5:95 to 95:5 in a 13 minutes gradient). LC/MS studies were run on a Hewlett-Packard HPLC 1100 coupled to a Micromass mass spectrometer.

HPLC: the purity was obtained at 214 nm, and expressed as a percentage of areas (are of the considered peak vs total of the peak areas).

Preparation of Intermediates

Intermediate A

Cis-N-(2-Methyl-1,2,3,4-tetrahydroquinolin-4-yl)-N-phenyl-acetamide

Intermediate A corresponds to a compound of formula cis-(1g), prepared according to step 1 to 6 of scheme 1 (R$^1$: Phenyl, R$^2$: CH$_3$, R$^4$: CH$_3$, R$^5$: H, R$^6$: H, R$^7$: H, R$^8$: H).

4-Methoxy Quinoline (Compound of Formula (1b))

To a solution of sodium methoxide (33 g) in methanol (130 ml), 4-chloroquinoline (10 g) was added under stirring. The mixture was heated under reflux for 6 hours. After cooling, the reaction mixture was concentrated, then dissolved in dichloromethane (250 ml) and washed with water (250 ml). The organic layer was dried over sodium sulfate. The solvent was evaporated to give a yellow oil (7.39 g, 76% yield) which was not purified.

$^1$H NMR [(CD$_3$)$_2$SO]: δ 8.8 (m, 1H), 8.15 (m, 1H), 8 (m, 1H), 7.8 (m, 1H), 7.6 (m, 1H), 7 (m, 1H), 4 (s, 3H).

MS positive ESI: m/z (m+H)$^+$=159

HPLC: r$_T$: 10.77, 97.16% purity

2-Methyl-4-oxo-3,4-dihydro-2H-quinoline-1-carboxylic Acid Benzyl Ester (Compound of Formula (1c))

To a solution of 4-methoxy quinoline (3g) in tetrahydrofuran (80 ml), under nitrogen, and under cooling at −78° C. in an acetone-dry ice bath and under stirring, a solution of methyl magnesium chloride at 3 M/l in tetrahydrofuran was added dropwise (77 ml) for 30 minutes. The mixture was stirred for 30 minutes and then benzyl chloroformate (32.15 g) was added dropwise for 45 minutes at −78° C. The mixture was stirred at room temperature over night. The reaction mixture was hydrolyzed with methanol (200 ml) and then with HCl 1 mol/l (200 ml) and finally concentrated. Dichloromethane (200 ml) and aqueous solution of sodium bicarbonate were added to the mixture under stirring. The separate organic layer was washed with an aqueous solution of sodium chloride (200 ml). The solvent was removed under reduce pressure to give an oil, which was chromatographed in silica gel with an eluent of cyclohexane/ethyl acetate (95/5). The fractions containing the desired compound were combined and evaporated to give an oil (5.44 g, 98% yield).

$^1$H NMR [(CD$_3$)$_2$SO]: δ 7.9 (m, 2H), 7.6 (t, 1H), 7.3–7.5 (m, 5H), 7.2 (m, 1H), 5.3 (d, 2H), 5.1 (t, 1H), 3.2 (m, 1H), 2.5 (m, 1H), 1.15 (d, 3H).

HPLC: r$_T$: 7.30, 96.9% purity

2-Methyl-4-phenylimino-3,4-dihydro-2H-quinoline-1-carboxylic Acid Benzyl Ester (Compound of Formula (1d))

To a solution of 2-Methyl-4-oxo-3,4-dihydro-2H-quinoline-1-carboxylic acid benzyl ester (9 g), triethylamine (24.65 g), aniline (5.7 g) in dichloromethane (110 ml), cooled at −5° C. in an ice/sodium chloride bath, a solution of titanium chloride in toluene 1 mol/l was dropwise added for 10 minutes. The mixture was stirred over night at room temperature and then washed with dichloromethane and an aqueous solution of potassium carbonate. The organic layer was separated, dried over sodium sulfate and the solvent was removed under reduced pressure to give a brown oil (16 g) which was directly used in the next step.

$^1$H NMR [CDCl$_3$]: δ 8.3 (m, 1H), 7.8 (m, 1H), 7.3–7.5 (m, 8H), 7.2 (m, 1H), 7.1 (m,1H), 6.8 (m, 2H), 5.2 (dd, 2H), 5 (m, 1H), 2.75 (m, 1H), 2.55 (m, 1H), 1.15 (m, 3H).

Cis-2-methyl-4-phenylamino-3,4-dihydro-2H-quinoline-1-carboxylic Acid Benzyl Ester (Compound of Formula Cis-(1e))

To a solution of 2-methyl-4-phenylimino-3,4-dihydro-2H-quinoline-1-carboxylic acid benzyl ester (16 g) in acetic acid (450 ml), sodium triacetoxyborohydride was added in small amounts (32.32 g), under stirring, at room temperature. The reaction mixture was then stirred at room temperature for one hour and poured on 1 liter of cold water under stirring. After precipitation, the mixture was filtered, dissolved in ethyl acetate and then, washed with water. The organic layer was separated and dried over sodium sulfate. The solvent was removed to give the crude compound (9g), recrystallised in hot cyclohexane (40 ml), and then filtered at room temperature to give the desired compound (5.3 g, 46.6% yield).

$^1$H NMR [CDCl$_3$]: δ 7.5 (m, 1H), 7.15–5.5 (m, 9H), 7.1 (m, 1H), 6.75 (m, 1H), 6.65 (m, 2H), 5.25 (dd, 2H), 4.6 (m, 1H), 4.3 (m, 1H), 3.8 (m, 1H), 2.6 (m, 1H), 1.4 (m, 1H), 1.25 (m, 3H).

HPLC: r$_T$: 12.50, 100% purity

Cis-4-(acetyl-phenylamino)-2-methyl-3,4-dihydro-2H-quinoline-1-carboxylic Acid Benzyl Ester (Compound of Formula Cis-(1f))

To a solution of cis-2-methyl-4-phenylamino-3,4-dihydro-2H-quinoline-1-carboxylic acid benzyl ester (5.3 g), diisopropyl ethyl amine (2.73 g) in dioxane (31 ml), anhydride acetic (7.26 g) was added under stirring. The mixture was heated under reflux over night. After cooling, dichloromethane and an aqueous solution of potassium carbonate were added. The organic layer was separated, and then dried over sodium sulfate. Organic solvent was removed under reduce pressure to give the crude compound (18 g). The desired compound (3.8 g, 64% yield) was obtained after purification by flash chromatography on silica gel with cyclohexane/ethyl acetate (80/20) as eluent and then cyclohexane/ethyl acetate (50/50).

¹H NMR [CDCl₃]: δ 7.1–7.5 (m, 14H), 5.45 (m, 1H), 5.2 (dd, 2H), 4.45 (m, 1H), 2.2 (m, 1H), 2.05 (s, 3H), 1.3 (m, 1H), 1.1 (m,3H).

HPLC: r$_T$: 11.64, 100% purity

Intermediate A (Compound of Formula Cis-(1 g))

To a solution of cis-4-(acetyl-phenylamino)-2-methyl-3,4-dihydro-2H-quinoline-1-carboxylic acid benzyl ester (3.8 g), ammonium formate (5.7 g) in ethanol (90 ml), palladium (PD/C at 10% few milligrams) was added. The reaction mixture was heated under reflux for two hours. After cooling the mixture was filtered on celite and the solvent was evaporated under reduce pressure to give intermediate A (2.3 g, 90% yield).

¹H NMR [CDCl₃]: δ 7.25 (m, 4H), 7.0 (m, 3H), 6.75 (t, 1H), 6.45 (d, 1H), 6.3 (m, 1H), 3.55 (m, 2H), 1.9 (m+s, 4H), 1.35 (m, 1H), 1.1 (d, 3H).

HPLC: r$_T$: 8.14, 100% purity

Intermediate B

N-Benzyl-(2-methyl-1,2,3,4-tetrahydroquinolin-4-yl)-acetamide

Intermediate B corresponds to compound of formula (1g) wherein R¹: benzyl, R²: CH₃, R⁴: CH₃, R⁵: H, R⁶: H, R⁷: H and R⁸: H.

Intermediate Cis-B (Cis-N-Benzyl-(2-methyl-1,2,3,4-tetrahydroquinolin-4-yl)-acetamide) and Trans-B (Trans-N-Benzyl-(2-methyl-1,2,3,4-tetrahydroquinolin-4-yl)-acetamide) were prepared as follows:

2-Methyl-4-benzylimino-3,4-dihydro-2H-quinoline-1-carboxylic Acid Benzyl Ester (Compound of Formula (1d))

To a solution of 2-Methyl-4-oxo-3,4-dihydro-2H-quinoline-1-carboxylic acid benzyl ester (1.00 g, 3.39 mmol), triethylamine (3.77 mL, 27.1 mmol) in dichloromethane (10 ml), cooled at 0° C. in an ice/sodium chloride bath, a solution of titanium tetrachloride in toluene (3.39 mL, 1.0 M in toluene) was dropwise added for 10 minutes. Benzyl amine (0.74 mL, 3.39 mmol) was added and the mixture was stirred over night at room temperature. The reaction was quenched with saturated NaHCO₃ solution (100 mL) and the mixture was extracted with ethyl acetate (3×200 mL). The combined organic layers were washed with brine (200 mL), dried (Na₂SO₄), filtered and concentrated to give a reddish oil (1.70 g) which was used directly in the next step.

¹H NMR [CDCl₃]: δ 8.3 (d, 1H), 7.6 (d, 1H), 7.1–7.5 (m, 12H), 5.3 (d, 1H), 5.2 (d, 1H) 5.1 (m, 1H), 4.7 (d, 1H), 4.6 (d, 1H) 2.8 (m, 2H), 1.1 (d, 3H).

MS positive ESI: m/z (m+H)⁺=385

Cis and Trans-2-Methyl-4-benzylamino-3,4-dihydro-2H-quinoline-1-carboxylic Acid Benzyl Ester (Compound of Formula (1e))

To a solution of 2-Methyl-4-benzylimino-3,4-dihydro-2H-quinoline-1-carboxylic acid benzyl ester (1.70 g, 3.38 mmol) in methanol (50 ml), was added sodium borohydride (2.56 g, 67.7 mmol) in small portions. The reaction was stirred overnight and then concentrated to near dryness under vacuum. This was then diluted with a concentrated solution of potassium carbonate (50 mL) and then extracted with ethyl acetate (3×150 mL). The combined organic layers were washed with brine (200 mL), dried (Na₂SO₄), filtered and concentrated to give a pale yellow oil (1.34 g). This material was purified on silica gel with 15% ethyl acetate/hexane to provide two fractions:

Higher Rf fraction—Cis-2-Methyl-4-benzylamino-3,4-dihydro-2H-quinoline-1-carboxylic acid benzyl ester (300 mg): ¹H NMR [D₆ DMSO]:: δ7.5 (d, 1H), 7.4 (d, 2H), 7.1–7.3 (m, 11H), 5.1 (q, 1H), 5.2 (d, 2H), 4.3 (m, 1H), 3.9 (m, 2H), 2.8 (m, 1H), 1.1 (d, 3H), 1.0 (m, 1H).

MS positive ESI: m/z (m+H)⁺=387

A portion of this material was treated with HCl gas and recrystallized to provide a single crystal which was identified as the cis diastereomer by X-ray diffraction.

Lower Rf fraction—Trans-2-Methyl-4-benzylamino-3,4-dihydro-2H-quinoline-1-carboxylic acid benzyl ester (300 mg): ¹H NMR [D₆ DMSO]:: δ7.5 (d, 1H), 7.4–7.2 (m, 8H), 7.0 (t, 1H), 5.2 (q, 2H), 4.5 (m, 1H), 3.7 (m, 1H), 3.6 (m, 2H), 2.5 (m, 1H), 2.3 (m, 1H), 1.5 (m, 1H), 1.1 (d, 3H).

MS positive ESI: m/z (m+H)⁺=387

Cis-4-(acetyl-benzylamino)-2-methyl-3,4-dihydro-2H-quinoline-1-carboxylic Acid Benzyl Ester (Compound of Formula Cis-(1f)

To a solution of Cis-2-Methyl-4-benzylamino-3,4-dihydro-2H-quinoline-1-carboxylic acid benzyl ester (300 mg, 0.776 mmol), diisopropyl ethyl amine (0.135 mL, 0.776 mmol) in dioxane (1.5 mL), was added anhydride acetic (0.732 mL, 7.76 mmol) with stirring. The mixture was heated under reflux over night, cooled and directly chromatographed on silica gel utilizing 50% ethyl acetate/hexane to provide the title compound (300 mg) as an oil. ¹H NMR [CDCl₃]: δ 7.6–6.9 (m, 14H), 5.5 (d, 1H), 5.3 (d, 1H), 5.2 (t, 1H), 4.8 (m, 1H), 4.4 (m, 2H), 3.8 (d, 1H), 2.4 (s, 3H), 1.5 (m, 1H), 1.2 (m, 3H).

MS positive ESI: m/z (m+NH₄)⁺=446

Trans-4-(acetyl-benzylamino)-2-methyl-3,4-dihydro-2H-quinoline-1-carboxylic acid benzyl ester (compound of formula trans-(1f)). When the Trans isomer (300 mg) was utilized in the above reaction, the title compound (320 mg) was isolated as an oil. ¹H NMR [CDCl₃]: δ 7.8 (d, 1H), 7.4–7.0 (m, 13H), 6.6 (m, 1H), 5.2 (s, 2H), 4.8 (m, 1H), 4.4 (d, 2H), 4.1 (d, 1H), 2.4, 2.1 (s, 3H), 2.0 (m, 1H), 1.2 (d, 3H), 1.3 (m, 2H).

MS positive ESI: m/z (m+NH₄)⁺=446

Cis-N-Benzyl-(2-methyl-1,2,3,4-tetrahydroquinolin-4-yl)-acetamide (Intermediate Cis-B)

To a solution of Cis-4-(acetyl-benzylamino)-2-methyl-3,4-dihydro-2H-quinoline-1-carboxylic acid benzyl ester (290 mg, 0.677 mmol) and methanol (10 mL) was added 10% Pd-C (100 mg). Hydrogen gas was then added via a balloon, and the solution was stirred rapidly. After 1 h, the reaction was filtered, the residual catalyst washed with toluene, and the organic layers combined and concentrated to give the title compound as an oil. ¹H NMR [CDCl₃]: δ 7.4–7.2 (m, 5H), 7.1 (m, 1H), 6.9 (m, 1H), 6.7 (m, 1H), 6.5 (m, 1H), 6.3 (br s, 1H), 5.3, 5.1 (m, 1H), 4.5 (d, 1H), 4.2 (d, 1H), 3.9–3.5 (m, 3H), 2.4, 2.1 (s, 3H), 2.1, 1.9 (m, 1H), 1.5 (m, 1H), 1.1 (m, 3H).

MS positive ESI: m/z (m+H)⁺=295

Trans-N-Benzyl-(2-methyl-1,2,3,4-tetrahydroquinolin-4-yl)-acetamide (Intermediate Trans-B)

Trans-4-(acetyl-benzylamino)-2-methyl-3,4-dihydro-2H-quinoline

When the trans isomer (306 mg) was utilized in the above reaction, the title compound was isolated as an oil. ¹H NMR [CDCl₃]: δ 7.4–7.2 (m, 3H), 7.2 (d, 1H), 7.1 (t, 1H), 6.9 (d, 1H), 6.7 (m, 2H), 6.0 (t, 1H), 5.1, 4.9 (m, 1H), 4.5 (d, 1H), 4.4 (d, 1H), 3.9–3.3 (m, 3H), 2.4, 2.1 (s, 3H), 2.1, 1.9 (m, 1H), 1.5 (m, 2H), 1.1 (m, 3H).

MS: 295, MH+

Example 1

Cis-N-[2-Methyl-1-(thiophene-2-carbonyl)-1,2,3,4-tetrahydroquinolin-4-yl]-N-phenyl-acetamide $R^1$: phenyl, $R^2$: $CH_3$, $R^3$: thien-2-yl, $R^4$: $CH_3$, $R^5$: H, $R^6$: H, $R^7$: H, $R^8$: H.

To a solution of intermediate A (0.1 g), diisopropyl ethyl amine (0.05 g) in dioxane (1 ml), was added 2-thiophencarbonyl chloride (0.057 mg), under stirring, at room temperature for 3 hours. Then dichloromethane (2 ml) and water (2 ml) were added. The organic layer was separated and the solvent was removed under reduce pressure. The crude compound was crystallized in diethyl ether, filtered and dried to give a white solid (0.055 g, 39.6% yield).

1H NMR [CDCl3]: d 7.4–7.2 (m, 8H), 7.05 (m, 1H), 6.85 (t, 1H), 6.75 (t, 1H), 6.7 (d, 1H), 5.5 (m, 1H), 4.7 (m, 1H), 2.3 (m, 1H), 2.0 (s, 3H), 1.6 (s, 1H), 1.1 (d, 3H).

HPLC: $r_T$: 10.15, 100% purity

MS positive ESI: m/z $(m+H)^+$=391

Example 2

Cis-N-(1-Benzoyl-2-methyl-1,2,3,4-tetrahydroquinolin-4-yl)-N-phenyl-acetamide $R^1$: phenyl, $R^2$: $CH_3$, $R^3$: phenyl, $R^4$: $CH_3$, $R^5$: H, $R^6$: H, $R^7$: H, $R^8$: H.

The titled compound was prepared according to protocol A, using intermediate A and appropriate reactants.

1H NMR [CDCl3]: d 7.4–7.15 (m, 12H), 6.9 (t, 1H), 6.5 (d, 1H), 5.6 (m, 1H), 4.8 (m, 1H), 2.3 (m, 1H), 2.0 (s, 3H), 1.6 (s, 1H), 1.1 (d, 3H).

HPLC: $r_T$: 10.15, 100% purity

MS positive ESI: m/z $(m+H)^+$=385

Example 3

Cis-N-[2-Methyl-1-(pyridine-4-carbonyl)-1,2,3,4-tetrahydroquinolin-4-yl]-N-phenyl-acetamide $R^1$: phenyl, $R^2$: $CH_3$, $R^3$: pyridin-4-yl, $R^4$: $CH_3$, $R^5$: H, $R^6$: H, $R^7$: H, $R^8$: H.

The titled compound was prepared according to protocol A, using intermediate A and appropriate reactants.

1H NMR [CDCl3]: d 8.5 (d, 2H), 7.4 (m, 4H), 7.2 (m, 3H), 7.0 (d, 2H), 6.9 (t, 1H), 6.45 (d, 1H), 5.6 (m, 1H), 4.8 (m, 1H), 2.3 (m, 1H), 2.0 (s, 3H), 1.65 (s, 1H), 1.1 (d, 3H).

HPLC: $r_T$: 7.76, 98.2% purity

MS positive ESI: m/z $(m+H)^+$=386

Example 4

Cis-N-[2-Methyl-1-(1-oxy-pyridine-4-carbonyl)-1,2,3,4-tetrahydroquinolin-4-yl]-N-phenyl-acetamide $R^1$: phenyl, $R^2$: $CH_3$, $R^3$: 1-oxy-pyridin-4-yl, $R^4$: $CH_3$, $R^5$: H, $R^6$: H, $R^7$: H, $R^8$: H.

To a solution of Cis-N-[2-methyl-1-(pyridine-4-carbonyl)-1,2,3,4-tetrahydroquinolin-4-yl]-N-phenyl-acetamide (0.1 g) in dichloromethane (2.6 ml) was added meta-chloro-para-benzoic acid (0.26 mmol). After 3 hours, dichloromethane was added and the solution was washed using water and carbonate potassium. The organic layer was separated and dried over sodium sulfate. The solvent was removed to give the title compound (60 mg).

$^1$H NMR [CDCl$_3$]: δ 8.0 (d, 2H), 7.4 (m, 3H), 7.2 (m, 4H), 7.0 (m, 3H), 6.5 (d, 1H), 5.55 (m, 1H), 4.7 (m, 1H), 2.3 (m, 1H), 2.0 (s, 3H), 1.15 (m+d, 4H).

HPLC: $r_T$: 7.58, 97% purity

MS positive ESI: m/z $(m+H)^+$=402

Example 5

Cis-N-[1-(4-Methoxy-benzoyl)-2-methyl-1,2,3,4-tetrahydroquinolin-4-yl]-N-phenyl-acetamide $R^1$: phenyl, $R^2$: $CH_3$, $R^3$: 4-methoxyphenyl, $R^4$: $CH_3$, $R^5$: H, $R^6$: H, $R^7$: H, $R_8$: H.

The titled compound was prepared according to protocol A, using intermediate A and appropriate reactants.

$^1$H NMR [CDCl$_3$]: δ 7.4 (m, 4H), 7.3 (m, 2H), 7.2 (m, 3H), 6.9 (t, 1H), 6.7 (d, 2H), 6.5 (d, 1H), 5.6 (m, 1H), 4.75 (m, 1H), 3.75 (s, 3H), 2.3 (m, 1H), 2.0 (s, 3H), 1.6 (s, 1H), 1.15 (d, 3H).

HPLC: $r_T$: 10.20, 97.7% purity

MS positive ESI: m/z $(m+H)^+$=415

Example 6

Cis-N-[1-(4-Hydroxy-benzoyl)-2-methyl-1,2,3,4-tetrahydroquinolin-4-yl]-N-phenyl-acetamide $R^1$: phenyl, $R^2$: $CH_3$, $R^3$: 4-hydroxyphenyl, $R^4$: $CH_3$, $R^5$: H, $R^6$: H, $R^7$: H, $R^8$: H.

To a solution N-[1-(4-Methoxy-benzoyl)-2-methyl-1,2,3,4-tetrahydroquinolin-4-yl]-N-phenyl-acetamide (0.1 g) in dichloromethane (2.4 ml) at 0° C., was added boron tribromide (0.265 mmol). After 3 hours, ice and ethyl acetate were added and the solution was washed using water and carbonate potassium. The organic layer was separated and dried over sodium sulfate. The solvent was removed to afford an amorphous materiel. The product was purified by chromatography on silica gel using a mixture of dichloromethane and ethanol (95:5) as eluent to give the title compound (50 mg).

$^1$H NMR [CDCl$_3$]: δ 7.95 (s, 1H), 7.4–7.2 (m, 6H), 7.1 (t, 1H), 6.9 (m, 3H), 6.5 (d, 1H), 6.4 (d, 2H), 5.5 (m, 1H), 4.65 (m, 1H), 2.2 (m, 1H), 2.0 (s, 3H), 1.05 (m+d, 4H).

HPLC: $r_T$: 9.08, 95.6% purity

MS positive ESI: m/z $(m+H)^+$=401

Example 7

Cis-N-[2-Methyl-1-(4-trifluoromethyl-benzoyl)-1,2,3,4-tetrahydroquinolin-4-yl]-N-phenyl-acetamide $R^1$: phenyl, $R^2$: $CH_3$, $R^3$: 4-trifluoromethylphenyl, $R^4$: $CH_3$, $R^5$: H, $R^6$: H, $R^7$: H, $R^8$: H.

The titled compound was prepared according to protocol A, using intermediate A and appropriate reactants.

$^1$H NMR [CDCl$_3$]: δ 7.4–7.1 (m, 11H), 6.85 (t, 1H), 6.35 (d, 1H), 5.55 (m, 1H), 4.7 (m, 1H), 2.25 (m, 1H), 2.0 (s, 3H), 1.1 (d+m, 4H).

HPLC: $r_T$: 11.36, 93.6% purity

MS positive ESI: m/z $(m+H)^+$=453

Example 8

Cis-N-[2-Methyl-1-(3-phenyl-acryloyl)-1,2,3,4-tetrahydroquinolin-4-yl]-N-phenyl-acetamide $R^1$: phenyl, $R^2$: $CH_3$, $R^3$: —CH=CH-phenyl, $R^4$: $CH_3$, $R^5$: H, $R^6$: H, $R^7$: H, $R^8$: H.

The titled compound was prepared according to protocol A, using intermediate A and appropriate reactants.

¹H NMR [CDCl₃]: δ 7.7 (d, 1H), 7.4–7.2 (m, 13H), 7.1 (d, 1H), 6.6 (d, 1H), 5.4 (m, 1H), 4.75 (m, 1H), 2.25 (m, 1H), 2.0 (s, 3H), 1.6 (s, 1H), 1.15 (d, 3H).

HPLC: $r_T$: 10.92, 100% purity

MS positive ESI: m/z (m+H)⁺=411

Example 9

Cis-N-[1-(4-Cyano-benzoyl)-2-methyl-1,2,3,4-tetrahydroquinolin-4-yl]-N-phenyl-acetamide R¹: phenyl, R²: CH₃, R³: 4-cyano-benzoyl, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.4–7.2 (m, 11H), 6.9 (t, 1H), 6.4 (d, 1H), 5.6 (m, 1H), 4.8 (m, 1H), 2.3 (m, 1H), 2.0 (s, 3H), 1.15 (d+m, 4H).

HPLC: $r_T$: 10.05, 99.5% purity

MS positive ESI: m/z (m+H)⁺=410

Example 10

Cis-N-[1-(4-Chloro-benzoyl)-2-methyl-1,2,3,4-tetrahydroquinolin-4-yl]-N-phenyl-acetamide R¹: phenyl, R²: CH₃, R³: 4-chloro-phenyl, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.4–7.1 (m, 11H), 6.9 (t, 1H), 6.45 (d, 1H), 5.6 (m, 1H), 4.75 (m, 1H), 2.3 (m, 1H), 2.0 (s, 3H), 1.1 (d+m, 4H).

HPLC: $r_T$: 10.98, 99.5% purity

MS positive ESI: m/z (m+H)⁺=419

Example 11

4-[cis-4-(Acetyl-phenyl-amino)-2-methyl-3,4-dihydro-2H-quinoline-1-carbonyl]-benzoic Acid Methyl Ester R¹: phenyl, R²: CH₃, R³: 4-benzoic acid methyl ester, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.9 (d, 2H), 7.4–7.25 (m, 8H), 7.15 (t, 1H), 6.9 (m, 1H), 6.4 (d, 1H), 5.6 (m, 1H), 4.8 (m, 1H), 3.9 (s, 3H), 2.3 (m, 1H), 2.0 (s, 3H), 1.15 (d+m, 4H).

HPLC: 100% purity

MS positive ESI: m/z (m+H)⁺=443

Example 12

4-[Cis-4-(Acetyl-phenyl-amino)-2-methyl-3,4-dihydro-2H-quinoline-1-carbonyl]-benzoic Acid R¹: phenyl, R²: CH₃, R³: 4-benzoic acid, R⁴: CH₃, R⁵: H, R⁶: H, R⁷: H, R⁸: H.

A solution of 4-[4-(Acetyl-phenyl-amino)-2-methyl-3,4-dihydro-2H-quinoline-1-carbonyl]-benzoic acid methyl ester (50 mg) and lithium hydroxyde (0.283 mmol) in methanol (2 ml) and water (1 ml) was stirred at room temperature overnight. After addition of water, the mixture was washed with dichloromethane. The aqueous layer was acidified and then extracted using ethyl acetate. The organic layer is separated and dried over sodium sulfate. The solvent was removed to give the title compound (50 mg).

¹H NMR [CDCl₃]: δ 7.9 (d, 2H), 7.4–7.2 (m, 9H), 6.9 (m, 1H), 6.4 (d, 1H), 5.6 (m, 1H), 4.8 (m, 1H), 2.3 (m, 1H), 2.0 (s, 3H), 1.15 (d+m, 4H).

HPLC: $r_T$: 8.92, 100% purity

MS positive ESI: m/z (m+H)⁺=429

Example 13

Cis-N-[2-Methyl-1-(3-phenyl-propionyl)-1,2,3,4-tetrahydroquinolin-4-yl]-N-phenyl-acetamide R¹: phenyl, R²: CH₃, R³: —(CH₂)₂-phenyl, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.4–7.2 (m, 10H), 7.1 (m, 3H), 6.95 (d, 1H), 5.2 (m, 1H), 4.7 (m, 1H), 3.0–2.6 (m, 4H), 2.1 (m, 1H), 2.0 (s, 3H), 1.0 (d+m, 4H).

HPLC: $r_T$: 10.71, 100% purity

MS positive ESI: m/z (m+H)⁺=413

Example 14

Cis-N-[2-Methyl-1-(5-methyl-thiophene-2-carbonyl)-1,2,3,4-tetrahydroquinolin-4-yl]-N-phenyl-acetamide R¹: phenyl, R²: CH₃, R³: 5-methyl-thien-2-yl, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.4 (m, 4H), 7.25 (m, 3H), 7.1 (t, 1H), 6.9 (d, 1H), 6.5 (d, 1H), 6.4 (d, 1H), 5.5 (m, 1H), 4.6 (m, 1H), 2.3 (s, 3H), 2.2 (m, 1H), 2.0 (s, 3H), 1.1 (d+m, 4H).

HPLC: $r_T$: 10.51, 95.3% purity

MS positive ESI: m/z (m+H)⁺=405

Example 15

Cis-N-[1-(Benzofurazan-5-carbonyl)-2-methyl-1,2,3,4-tetrahydroquinolin-4-yl]-N-phenyl-acetamide R¹: phenyl, R²: CH₃, R³: benzo[1,2,5]oxadiazol-5-yl, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.9 (s, 1H), 7.5 (m, 1H), 7.3 (m, 4H), 7.15 (m, 3H), 6.9 (m, 2H), 6.5 (m, 1H), 5.5 (m, 1H), 4.7 (m, 1H), 2.25 (m, 1H), 2.0 (s, 3H), 1.1 (d+m, 4H).

HPLC: $r_T$: 10.92, 100% purity

MS positive ESI: m/z (m+H)⁺=427

Example 16

Cis-N-(2-Methyl-1-phenylacetyl-1,2,3,4-tetrahydroquinolin-4-yl)-N-phenyl-acetamide R¹: phenyl, R²: CH₃, R³: benzyl, R⁴: CH₃, R⁵: H, R⁶: H, R⁷: H, R⁸: H.

The titled compound was prepared according to protocol A, using intermediate A and appropriate reactants.

¹H NMR [CDCl₃]: δ 7.3–7.2 (m, 7H), 7.1–7.0 (m, 7H), 5.0 (m, 1H), 4.6 (m, 1H), 3.65 (dd, 2H), 2.1 (m, 1H), 1.9 (s, 3H), 1.0 (d+m, 4H).

HPLC: $r_T$: 10.41, 100% purity

MS positive ESI: m/z (m+H)⁺=399

Example 17

Cis-N-[2-Methyl-1-(pyrazine-2-carbonyl)-1,2,3,4-tetrahydroquinolin-4-yl]-N-phenyl-acetamide $R^1$: phenyl, $R^2$: $CH_3$, $R^3$: pyrazin-2-yl, $R^4$: $CH_3$, $R^5$: H, $R^6$: H, $R^7$: H, $R^8$: H.

The titled compound was prepared according to protocol A, using intermediate A and appropriate reactants.

Example 18

Cis-N-[1-(6-Chloro-pyridine-3-carbonyl)-2-methyl-1,2,3,4-tetrahydroquinolin-4-yl]-N-phenyl-acetamide $R^1$: phenyl, $R^2$: $CH_3$, $R^3$: 6-chloro-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 19

Cis-N-[2-Methyl-1-(6-trifluoromethyl-pyridine-3-carbonyl)-1,2,3,4-tetrahydroquinolin-4-yl]-N-phenyl-acetamide $R^1$: phenyl, $R^2$: $CH_3$, $R^3$: 6-trifluoromethyl-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 20

Cis-N-[1-(2,6-Dimethoxy-pyridine-3-carbonyl)-2-methyl-1,2,3,4-tetrahydroquinolin-4-yl]-N-phenyl-acetamide $R^1$: phenyl, $R^2$: $CH_3$, $R^3$: 2,6-dimethoxy-pyridin-3-yl, $R^4$: $CH_3$, $R^5$: H, $R^6$: H, $R^7$: H, $R^8$H.

The titled compound was prepared according to protocol A, using intermediate A and appropriate reactants.

Example 21

Cis-N-[1-(2-Methoxy-pyridine-3-carbonyl)-2-methyl-1,2,3,4-tetrahydroquinolin-4-yl]-N-phenyl-acetamide $R^1$: phenyl, $R^2$: $CH_3$, $R^3$: 2-methoxy-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 22

Cis-N-[2-Methyl-1-(2-methylsulfanyl-pyridine-3-carbonyl)-1,2,3,4-tetrahydroquinolin-4-yl]-N-phenyl-acetamide $R^1$: phenyl, $R^2$: $CH_3$, $R^3$: 2-methylsulfanyl-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 23

Cis-N-[1-(2-Chloro-pyridine-3-carbonyl)-2-methyl-1,2,3,4-tetrahydroquinolin-4-yl]-N-phenyl-acetamide $R^1$: phenyl, $R^2$: $CH_3$, $R^3$: 2-chloro-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 24

Cis-N-[2-Methyl-1-(5-methyl-pyrazine-2-carbonyl)-1,2,3,4-tetrahydroquinolin-4-yl]-N-phenyl-acetamide $R^1$: phenyl, $R^2$: $CH_3$, $R^3$: 5-methyl-pyrazin-2-yl, $R^4$: $CH_3$, $R^5$: H, $R^6$: H, $R^7$: H, $R^8$: H.

The titled compound was prepared according to protocol A, using intermediate A and appropriate reactants.

Example 25

Cis-N-[1-(2-Chloro-6-methyl-pyridine-3-carbonyl)-2-methyl-1,2,3,4-tetrahydroquinolin-4-yl]-N-phenyl-acetamide $R^1$: phenyl, $R^2$: $CH_3$, $R^3$: 2-chloro-6-methyl-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 26

Cis-N-[1-(4-Chloro-1,3-dimethyl-1H-pyrazolo[3,4-b]pyridine-3-carbonyl)-2-methyl-1,2,3,4-tetrahydroquinolin-4-yl]-N-phenyl-acetamide $R^1$: phenyl, $R^2$: $CH_3$, $R^3$: 4-chloro-1,3-dimethyl-1H-pyrazolo[3,4-b]pyridin-5-yl, $R^4$: $CH_3$, $R^5$: H, $R^6$: H, $R^7$: H, $R^8$: H.

The titled compound was prepared according to protocol A, using intermediate A and appropriate reactants.

Example 27

Cis-N-[2-Methyl-1-(6-(2,2,2-trifluoro-ethoxy)-pyridine-3-carbonyl)-1,2,3,4-tetrahydroquinolin-4-yl]-N-phenyl-acetamide $R^1$: phenyl, $R^2$: $CH_3$, $R^3$: 6-(2,2,2-trifluoroethoxy)-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 28

Cis-N-[2-Methyl-1-(2-propylsulfanyl-pyridine-3-carbonyl)-1,2,3,4-tetrahydroquinolin-4-yl]-N-phenyl-acetamide $R^1$: phenyl, $R^2$: $CH_3$, $R^3$: 2-propylsulfanyl-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 29

Cis-N-[1-(5,6-Dichloro-pyridine-3-carbonyl)-2-methyl-1,2,3,4-tetrahydroquinolin-4-yl]-N-phenyl-acetamide $R^1$: phenyl, R $CH_3$, $R^3$: 5,6-dichloro-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 30

Cis-N-[1-(2,6-Dichloro-pyridine-3-carbonyl)-2-methyl-1,2,3,4-tetrahydroquinolin-4-yl]-N-phenyl-acetamide $R^1$: phenyl, $R^2$: $CH_3$, $R^3$: 2,6-dichloro-pyridin-3-yl, $R^4$: $CH_3$, $R^5$: H, $R^6$: H, $R^7$: H, $R^8$: H.

The titled compound was prepared according to protocol A, using intermediate A and appropriate reactants.

Example 31

Cis-N-[2-Methyl-1-(4-methyl-[1,2,3]thiadiazole-5-carbonyl)-1,2,3,4-tetrahydroquinolin-4-yl]-N-phenyl-acetamide $R^1$: phenyl, $R^2$: $CH_3$, $R^3$: 4-methyl-[1,2,3]-thiadiazol-5-yl, $R^4$: $CH_3$, $R^5$: H, $R^6$: H, $R^7$: H, $R^8$: H.

The titled compound was prepared according to protocol A, using intermediate A and appropriate reactants.

Example 32

Cis-N-[2-Methyl-1-(5-methyl-isoxazole-3-carbonyl)-1,2,3,4-tetrahydroquinolin-4-yl]-N-phenyl-acetamide $R^1$: phenyl, $R^2$: $CH_3$, $R^3$: 5-methyl-isoxazol-3-yl, $R^4$: $CH_3$, $R^5$: H, $R^6$: H, $R^7$: H, $R^8$: H.

The titled compound was prepared according to protocol A, using intermediate A and appropriate reactants.

Example 33

Cis-N-[1-(2,5-Dimethyl-2H-pyrazole-3-carbonyl)-2-methyl-1,2,3,4-tetrahydroquinolin-4-yl]-N-phenyl-acetamide $R^1$: phenyl, $R^2$: $CH_3$, $R^3$: 2,5-dimethyl-2H-pyrazol-3-yl, $R^4$: $CH_3$, $R^5$: H, $R^6$: H, $R^7$: H, $R^8$: H.

The titled compound was prepared according to protocol A, using intermediate A and appropriate reactants.

Example 34

Cis-N-[2-Methyl-1-(1-methyl-1H-pyrrole-2-carbonyl)-1,2,3,4-tetrahydroquinolin-4-yl]-N-phenyl-acetamide $R^1$: phenyl, $R^2$: $CH_3$, $R^3$: 1-methyl-1H-pyrazol-2-yl, $R^4$: $CH_3$, $R^5$: H, $R^6$: H, $R^7$: H, $R^8$: H.

The titled compound was prepared according to protocol A, using intermediate A and appropriate reactants.

Example 35

Cis-N-[1-(Isoxazole-5-carbonyl)-2-methyl-1,2,3,4-tetrahydroquinolin-4-yl]-N-phenyl-acetamide $R^1$: phenyl, $R^2$: $CH_3$, $R^3$: isoxazol-5-yl, $R^4$: $CH_3$, $R^5$: H, $R^6$: H, $R^7$: H, $R^8$: H.

The titled compound was prepared according to protocol A, using intermediate A and appropriate reactants.

Example 36

Cis-N-[2-Methyl-1-(5-methyl-isoxazole-4-carbonyl)-1,2,3,4-tetrahydroquinolin-4-yl]-N-phenyl-acetamide $R^1$: phenyl, $R^2$: $CH_3$, $R^3$: 5-methyl-isoxazol-4-yl, $R^4$: $CH_3$, $R^5$: H, $R^6$: H, $R^7$: H, $R^8$: H.

The titled compound was prepared according to protocol A, using intermediate A and appropriate reactants.

Example 37

Cis-N-[1-(2,4-Dimethyl-thiazole-5-carbonyl)-2-methyl-1,2,3,4-tetrahydroquinolin-4-yl]-N-phenyl-acetamide $R^1$: phenyl, $R^2$: $CH_3$, $R^3$: 2,4-dimethyl-thiazol-5-yl, $R^4$: $CH_3$, $R^5$: H, $R^6$: H, $R^7$: H, $R^8$: H.

The titled compound was prepared according to protocol A, using intermediate A and appropriate reactants.

Example 38

Cis-N-[1-(5-Chloro-thiophene-2-carbonyl)-2-methyl-1,2,3,4-tetrahydroquinolin-4-yl]-N-phenyl-acetamide $R^1$: phenyl, $R^2$: $CH_3$, $R^3$: 5-chloro-thien-2-yl, $R^4$. $CH_3$, $R^5$: H, $R^6$: H, $R^7$: H, $R^8$: H.

The titled compound was prepared according to protocol A, using intermediate A and appropriate reactants.

Example 39

Cis-N-[1-(1,5-Dimethyl-1H-pyrazole-3-carbonyl)-2-methyl-1,2,3,4-tetrahydroquinolin-4-yl]-N-phenyl-acetamide $R^1$: phenyl, $R^2$: $CH_3$, $R^3$: 1,5-dimethyl-1H-pyrazol-3-yl, $R^4$: $CH_3$, $R^5$: H, $R^6$: H, $R^7$: H, $R^8$: H.

The titled compound was prepared according to protocol A, using intermediate A and appropriate reactants.

| Example | Name | $R^1$ | $R^2$ | $R^3$ | $R^4$ | $R^5$ | $R^6$ | $R^7$ | $R^8$ | LC (tR.; purity) | MS (ESI) |
|---|---|---|---|---|---|---|---|---|---|---|---|
| 40 | cis-N-[2-Methyl-1-(4-methyl-isothiazole-5-carbonyl)-1,2,3,4-tetrahydro-quinolin-4-yl]-N-phenyl-acetamide | Phenyl | $CH_3$ | 4-methyl-isothiazol-5-yl | $CH_3$ | H | H | H | H | 3.12 min 100% | 406 MH+ |
| 41 | ci-5-[4-(Acetyl-phenyl-amino)-2-methyl-3,4-dihydro-2H-quinoline-1-carbonyl]-thiophene-2-carboxylic acid dimethylamide | Phenyl | $CH_3$ | 2-carboxylic acid dimethylamide-thiophen-5-yl | $CH_3$ | H | H | H | H | 3.09 min 100% | 462 MH+ |
| 42 | cis-N-[1-(4-Hydroxy-quinoline-6-carbonyl)-2-methyl-1,2,3,4-tetrahydro-quinolin-4-yl]-N-phenyl-acetamide | Phenyl | $CH_3$ | 4-Hydroxy-quinolin-6-yl | $CH_3$ | H | H | H | H | 2.95 min 100% | 452 MH+ |
| 43 | cis-N-[1-(4-tert-Butyl-thiazole-2-carbonyl)-2-methyl-1,2,3,4-tetrahydro-quinolin-4-yl]-N-phenyl-acetamide | Phenyl | $CH_3$ | 4-tert-Butyl-thiazol-2-yl | $CH_3$ | H | H | H | H | 3.54 min 100% | 448 MH+ |

-continued

| Example | Name | R¹ | R² | R³ | R⁴ | R⁵ | R⁶ | R⁷ | R⁸ | LC (tR.; purity) | MS (ESI) |
|---|---|---|---|---|---|---|---|---|---|---|---|
| 44 | cis-N-[1-(2-Ethyl-pyridine-4-carbonyl)-2-methyl-1,2,3,4-tetrahydro-quinolin-4-yl]-N-phenyl-acetamide | Phenyl | CH₃ | 2-ethyl-pyridin-4-yl | CH₃ | H | H | H | H | 3.04 min 100% | 414 MH+ |
| 45 | cis-N-[1-(3,6-Dichloro-pyridine-2-carbonyl)-2-methyl-1,2,3,4-tetrahydro-quinolin-4-yl]-N-phenyl-acetamide | Phenyl | CH₃ | 3,6-Dichloro-pyridin-2-yl | CH₃ | H | H | H | H | 3.32 min 100% | 454 MH+ |
| 46 | cis-N-[1-(4-Chloro-2H-pyrazole-3-carbonyl)-2-methyl-1,2,3,4-tetrahydro-quinolin-4-yl]-N-phenyl-acetamide | Phenyl | CH₃ | 4-Chloro-2H-pyrazol-3-yl | CH₃ | H | H | H | H | 2.94 min 100% | 409 MH+ |
| 47 | cis-2-[4-(Acetyl-phenyl-amino)-2-methyl-3,4-dihydro-2H-quinoline-1-carbonyl]-isonicotinic acid methyl ester | Phenyl | CH₃ | 4-carboxylic acid methyl ester-pyridin-2-yl | CH₃ | H | H | H | H | 3.09 min 100% | 444 MH+ |
| 48 | cis-N-[2-Methyl-1-(4-[1,2,4]triazol-4-yl-benzoyl)-1,2,3,4-tetrahydro-quinolin-4-yl]-N-phenyl-acetamide | Phenyl | CH₃ | 4-[1,2,4]triazol-4-yl-benzoyl | CH₃ | H | H | H | H | 2.95 min 100% | 452 MH+ |
| 49 | cis-N-[1-(2,6-Dimethoxy-pyridine-4-carbonyl)-2-methyl-1,2,3,4-tetrahydro-quinolin-4-yl]-N-phenyl-acetamide | Phenyl | CH₃ | 2,6-Dimethoxy-pyridin-4-yl | CH₃ | H | H | H | H | 3.32 min 100% | 446 MH+ |
| 50 | cis-N-[1-(5-Ethyl-isoxazole-3-carbonyl)-2-methyl-1,2,3,4-tetrahydro-quinolin-4-yl]-N-phenyl-acetamide | Phenyl | CH₃ | 5-Ethyl-isoxazol-3-yl | CH₃ | H | H | H | H | 3.14 min 100% | 404 MH+ |
| 51 | cis-N-[2-Methyl-1-(2-tetrazol-1-yl-pyridine-4-carbonyl)-1,2,3,4-tetrahydro-quinolin-4-yl]-N-phenyl-acetamide | Phenyl | CH₃ | 2-tetrazol-1-yl-pyridin-4-yl | CH₃ | H | H | H | H | 3.01 min 100% | 454 MH+ |
| 52 | cis-N-[2-Methyl-1-(5-propyl-isoxazole-3-carbonyl)-1,2,3,4-tetrahydro-quinolin-4-yl]-N-phenyl-acetamide | Phenyl | CH₃ | 5-propyl-isoxazol-3-yl | CH₃ | H | H | H | H | 3.27 min 100% | 418 MH+ |
| 53 | cis-N-[1-(5-Isobutyl-2-methyl-2H-pyrazole-3-carbonyl)-2-methyl-1,2,3,4-tetrahydro-quinolin-4-yl]-N-phenyl-acetamide | Phenyl | CH₃ | 5-Isobutyl-2-methyl-2H-pyrazol-3-yl | CH₃ | H | H | H | H | 3.44 min 100% | 445 MH+ |
| 54 | cis-N-[1-(5-Bromo-furan-2-carbonyl)-2-methyl-1,2,3,4-tetrahydro-quinolin-4-yl]-N-phenyl-acetamide | Phenyl | CH₃ | 5-Bromo-furan-2-yl | CH₃ | H | H | H | H | 3.27 min 100% | 455 MH+ |
| 55 | cis-N-[2-Methyl-1-(6-phenyl-pyridine-3-carbonyl)-1,2,3,4-tetrahydro-quinolin-4-yl]-N-phenyl-acetamide | Phenyl | CH₃ | 6-phenyl-pyridin-3-yl | CH₃ | H | H | H | H | 3.39 min 100% | 462 MH+ |
| 56 | cis-N-[2-Methyl-1-(2-phenyl-pyridine-4-carbonyl)-1,2,3,4-tetrahydro-quinolin-4-yl]-N-phenyl-acetamide | Phenyl | CH₃ | 2-phenyl-pyridin-4-yl | CH₃ | H | H | H | H | 3.36 min 100% | 462 MH+ |
| 57 | cis-N-[2-Methyl-1-(quinoline-6-carbonyl)-1,2,3,4-tetrahydro-quinolin-4-yl]-N-phenyl-acetamide | Phenyl | CH₃ | quinolin-6-yl | CH₃ | H | H | H | H | 3.20 min 100% | 436 MH+ |
| 58 | cis-N-[1-(3,4-Dimethoxy-furan-2-carbonyl)-2-methyl-1,2,3,4-tetrahydro-quinolin-4-yl]-N-phenyl-acetamide | Phenyl | CH₃ | 3,4-Dimethoxy-furan-2-yl | CH₃ | H | H | H | H | 3.19 min 100% | 435 MH+ |
| 59 | cis-N-[2-Methyl-1-(3-methyl-furan-2-carbonyl)-1,2,3,4-tetrahydro-quinolin-4-yl]-N-phenyl-acetamide | Phenyl | CH₃ | 3-methyl-furan-2-yl | CH₃ | H | H | H | H | 3.19 min 100% | 389 MH+ |
| 60 | cis-N-[1-(2,5-Dimethyl-furan-3-carbonyl)-2-methyl-1,2,3,4-tetrahydro-quinolin-4-yl]-N-phenyl-acetamide | Phenyl | CH₃ | 2,5-Dimethyl-furan-3-yl | CH₃ | H | H | H | H | 3.36 min 100% | 403 MH+ |
| 61 | cis-N-[1-(2,4-Dimethyl-oxazole-5-carbonyl)-2-methyl-1,2,3,4-tetrahydro-quinolin-4-yl]-N-phenyl-acetamide | Phenyl | CH₃ | 2,4-Dimethyl-oxazol-5-yl | CH₃ | H | H | H | H | 3.10 min 100% | 404 MH+ |
| 62 | cis-N-[1-(5-Methoxymethyl-furan-2-carbonyl)-2-methyl- | Phenyl | CH₃ | 5-Methoxymethyl-furan-2-yl | | | | | | 3.13 min 100% | 419 MH+ |

-continued

| Example | Name | R¹ | R² | R³ | R⁴ | R⁵ | R⁶ | R⁷ | R⁸ | LC (tR.; purity) | MS (ESI) |
|---|---|---|---|---|---|---|---|---|---|---|---|
| | 1,2,3,4-tetrahydro-quinolin-4-yl]-N-phenyl-acetamide | | | | | | | | | | |
| 63 | cis-N-[1-(5-Fluoro-pyridine-3-carbonyl)-2-methyl-1,2,3,4-tetrahydro-quinolin-4-yl]-N-phenyl-acetamide | Phenyl | CH₃ | 5-Fluoro-pyridin-3-yl | CH₃ | H | H | H | H | 3.07 min 100% | 404 MH+ |
| 64 | cis-N-[2-Methyl-1-(quinoline-2-carbonyl)-1,2,3,4-tetrahydro-quinolin-4-yl]-N-phenyl-acetamide | Phenyl | CH₃ | quinoline-2-yl | CH₃ | H | H | H | H | 3.22 min 100% | 436 MH+ |
| 65 | cis-N-[2-Methyl-1-(6-methyl-pyridine-3-carbonyl)-1,2,3,4-tetrahydro-quinolin-4-yl]-N-phenyl-acetamide | Phenyl | CH₃ | 6-methyl-pyridin-3-yl | CH₃ | H | H | H | H | 3.00 min 100% | 400 MH+ |
| 66 | cis-N-[2-Methyl-1-(quinoline-3-carbonyl)-1,2,3,4-tetrahydro-quinolin-4yl]-N-phenyl-acetamide | Phenyl | CH₃ | quinolin-3-yl | CH₃ | H | H | H | H | 3.27 min 100% | 436 MH+ |
| 67 | cis-N-[2-Methyl-1-(1H-pyrazole-3-carbonyl)-1,2,3,4-tetrahydro-quinolin-4-yl]-N-phenyl-acetamide | Phenyl | CH₃ | 1H-pyrazol-3-yl | CH₃ | H | H | H | H | 2.88 min 100% | 375 MH+ |
| 68 | cis-N-[2-Methyl-1-(2H-pyrazole-3-carbonyl)-1,2,3,4-tetrahydro-quinolin-4-yl]-N-phenyl-acetamide | Phenyl | CH₃ | 2H-pyrazol-3-yl | CH₃ | H | H | H | H | 2.88 min 100% | 375 MH+ |
| 69 | cis-N-[1-(5-Isobutyl-isoxazole-3-carbonyl)-2-methyl-1,2,3,4-tetrahydro-quinolin-4-yl]-N-phenyl-acetamide | Phenyl | CH₃ | 5-Isobutyl-isoxazol-3-yl | CH₃ | H | H | H | H | 3.38 min 100% | 432 MH+ |
| 70 | cis-N-[2-Methyl-1-(quinoline-4-carbonyl)-1,2,3,4-tetrahydro-quinolin-4-yl]-N-phenyl-acetamide | Phenyl | CH₃ | quinolin-4-yl | CH₃ | H | H | H | H | 3.20 min 100% | 435 MH+ |
| 71 | cis-N-[2-Methyl-1-(6-methyl-pyridine-2-carbonyl)-1,2,3,4-tetrahydro-quinolin-4-yl]-N-phenyl-acetamide | Phenyl | CH₃ | 6-methyl-pyridin-2-yl | CH₃ | H | H | H | H | 3.06 min 100% | 400 MH+ |
| 72 | cis-N-[2-Methyl-1-(quinoxaline-5-carbonyl)-1,2,3,4-tetrahydro-quinolin-4-yl]-N-phenyl-acetamide | Phenyl | CH₃ | quinoxalin-5-yl | CH₃ | H | H | H | H | 3.15 min 100% | 437 MH+ |
| 73 | cis-N-[1-(3-Methoxy-thiophene-2-carbonyl)-2-methyl-1,2,3,4-tetrahydro-quinolin-4-yl]-N-phenyl-acetamide | Phenyl | CH₃ | 3-Methoxy-thiophen-2-yl | CH₃ | H | H | H | H | 3.25 min 100% | 421 MH+ |
| 74 | cis-N-[1-(5-tert-Butyl-2-methyl-furan-3-carbonyl)-2-methyl-1,2,3,4-tetrahydro-quinolin-4-yl]-N-phenyl-acetamide | Phenyl | CH₃ | 5-tert-Butyl-2-methyl-furan-3-yl | CH₃ | H | H | H | H | 3.65 min 100% | 445 MH+ |
| 75 | cis-N-[1-(5-Ethyl-2-methyl-2H-pyrazole-3-carbonyl)-2-methyl-1,2,3,4-tetrahydro-quinolin-4-yl]-N-phenyl-acetamide | Phenyl | CH₃ | 5-Ethyl-2-methyl-2H-pyrazol-3-yl | CH₃ | H | H | H | H | 3.23 min 100% | 417 MH+ |
| 76 | cis-N-[2-Methyl-1-([1,2,5]thiadiazole-3-carbonyl)-1,2,3,4-tetrahydro-quinolin-4-yl]-N-phenyl-acetamide | Phenyl | CH₃ | [1,2,5]thiadiazol-3-yl | CH₃ | H | H | H | H | 3.03 min 100% | 392 MH+ |
| 77 | cis-N-[2-Methyl-1-(2-methyl-5-propyl-2H-pyrazole-3-carbonyl)-1,2,3,4-tetrahydro-quinolin-4-yl]-N-phenyl-acetamide | Phenyl | CH₃ | 2-methyl-5-propyl-2H-pyrazol-3-yl | CH₃ | H | H | H | H | 3.35 min 100% | 431 MH+ |

Example 78

Cis-N-[2-Methyl-1-(pyridine-2-carbonyl)-1,2,3,4-tetrahydroquinolin-4-yl]-N-phenyl-acetamide R¹: phenyl, R²: CH₃, R³: pyridin-2-yl, R⁴: CH₃, R⁵: H, R⁶: H, R⁷: H, R⁸: H The titled compound was prepared according to protocol A, using intermediate A and appropriate reactants.

¹H NMR [(CDCl₃]: 8.5 (s, 1H), 7.4–7.1 (m, 7H), 6.95 (d, 1H), 6.8 (m, 1H), 6.5 (d, 1H), 5.55 (m, 1H), 4.8 (m, 1H), 2.3 (m, 1H), 2.0 (s, 3H), 1.25 (m, 1H), 1.1 (d, 3H).

HPLC: r_T: 8.6 min.

MS positive ESI: m/z (m+H)⁺=386

Example 79

Cis-N-(1-Benzoyl-2-methyl-1,2,3,4-tetrahydroquinolin-4-yl]-N-benzyl-acetamide $R^1$: benzyl, $R^2$: $CH_3$, $R^3$: phenyl, $R^4$: $CH_3$, $R^5$: H, $R^6$: H, $R^7$: H, $R^8$: H The titled compound was prepared according to protocol A, using intermediate Cis-B and appropriate reactants.

$^1$H NMR [($CDCl_3$]: 7.4 (m, 1H), 7.2 (m, 8H), 7.0 (m, 1H), 6.9 (m, 1H), 6.5 (m, 1H), 5.6 (d, 0.5H), 5.0 (m, 1H), 4.8 (m, 1H), 3.9 (m, 0.5H), 2.5 (m, 1H), 2.3, 2.4 (s, 3H), 1.5 (m, 1H), 1.2 (m, 3H)

HPLC: $r_T$: 3.17 min.
MS positive ESI: m/z (m+H)$^+$=399

Example 80

Cis-N-Benzyl-N-[2-methyl-1-(thiophene-2-carbonyl)-1,2,3,4-tetrahydroquinolin-4-yl]-acetamide $R^1$: benzyl, $R^2$: $CH_3$, $R^3$: thien-2-yl, $R^4$: $CH_3$, $R^5$: H, $R^6$: H, $R^7$: H, $R^8$: H.

The titled compound was prepared according to protocol A, using intermediate Cis-B and appropriate reactants.

$^1$H NMR [($CDCl_3$]: 7.5–6.7 (m, 12H), 5.6 (d, 0.5H), 4.9 (m, 1H), 4.7 (m, 1H), 3.9 (d, 0.5H), 2.5 (m, 1H), 2.31, 2.29 (s, 3H), 1.5 (m, 1H), 1.2 (app.d, 3H)

HPLC: $r_T$: 3.07 min.
MS positive ESI: m/z (m+H)$^+$=405

Example 81

Trans-N-Benzyl-N-[2-methyl-1-(thiophene-2-carbonyl)-1,2,3,4-tetrahydroquinolin-4-yl]-acetamide $R^1$: benzyl, $R^2$: $CH_3$, $R^3$: thien-2-yl, $R^4$: $CH_3$, $R^5$: H, $R^6$: H, $R^7$: H, $R^8$: H.

The titled compound was prepared according to protocol A, using intermediate Trans-B and appropriate reactants.

$^1$H NMR [($CDCl_3$]: 7.5–6.9 (m, 12H), 6.2 (t, 1H), 5.0 (m, 1H), 4.6 (d, 1H), 4.4 (d, 1H), 2.2 (s, 3H), 2.1 (m, 2H), 1.3 (d, 3H)

HPLC: $r_T$: 3.03 min.
MS positive ESI: m/z (m+H)$^+$=405

Example 82

Cis-N-Cyclohexyl-N-[2-methyl-1-(thiophene-2-carbonyl)-1,2,3,4-tetrahydroquinolin-4-yl]-acetamide $R^1$: cyclohexyl, $R^2$: $CH_3$, $R^3$: thien-2-yl, $R^4$: $CH_3$, $R^5$: H, $R^6$: H, $R^7$: H, $R^8$: H.

The titled compound was prepared according to protocol A, using appropriate reactants.

$^1$H NMR [($CDCl_3$]: 7.5–6.7 (m, 7H), 5.2 (m, 1H), 3.7 (m, 1H), 2.8 (m, 1H), 2.2 (s, 3H), 2.2–1.2 (m, 12H), 1.3 (d, 3H)

HPLC: $r_T$: 3.27 min.
MS positive ESI: m/z (m+H)$^+$=398

Example 83

Cis-N-(1-Benzoyl-6-methoxy-2-methyl-1,2,3,4-tetrahydroquinolin-4-yl)-N-phenyl-acetamide $R^1$: phenyl, $R^2$: $CH_3$, $R^3$: phenyl, $R^4$: $CH_3$, $R^5$: H, $R^6$: O—$CH_3$, $R^7$: H, $R^8$: H.

The titled compound was prepared according to protocol A, using appropriate reactants and starting from 4-chloro-6-methoxy-quinoline.

(0.045 g, 36% yield)

$^1$H NMR [($CD_3$)$_2$SO]: δ 7.5 (m, 2H), 7.4 (m, 3H), 7.3 (m, 1H), 7.2 (m, 2H), 7.1 (m, 2H), 6.9 (m, 1H), 6.5 (m, 1H), 6.4 (m, 1H), 5.4 (m, 1H), 4.6 (m, 1H), 3.6 (s, 3H), 2.6 (m, 1H), 1.9 (s, 3H), 1.2 (m, 1H), 1.0 (d,3H).

HPLC: $r_T$: 10.05, 98.8% purity

MS positive ESI: m/z (m+H)$^+$=415

Example 84

Cis-N-(1-Benzoyl-6-hydroxy-2-methyl-1,2,3,4-tetrahydroquinolin-4-yl)-N-phenyl-acetamide $R^1$: phenyl, $R^2$: $CH_3$, $R^3$: phenyl, $R^4$: $CH_3$, $R^5$: H, $R^6$: OH, $R^7$H, $R^8$H.

To a solution of 79 mg (0.19 mM) of Cis-N-(1-Benzoyl-6-methoxy-2-methyl-1,2,3,4-tetrahydroquinolin-4-yl)-N-phenyl-acetamide in 3 ml of dichloromethane were dropwise added 50 μl of boron tribromide. After 3 hours, ice was added and the mixture was extracted by ethyl acetate. The organic layer was dried by sodium sulfate and evaporated under reduced pressure to give a white solid that was purified by silicagel with dichloromethane/methanol 95/5 as eluent. (0.073 g, 96% yield).

$^1$H NMR [($CD_3$)$_2$SO]: δ+9.4 (s, 1H) 7.5 (m, 2H), 7.4 (m, 3H), 7.3 (m, 1H), 7.2 (m, 2H), 7.1 (m, 2H), 6.8 (s, 1H), 6.3 (s, 2H), 5.4 (m, 1H), 4.6 (m, 1H), 2.4 (m, 1H), 1.9 (s, 3H), 1.3 (m, 1H), 1.0 (m, 3H).

HPLC: $r_T$: 8.58, 100% purity
MS positive ESI: m/z (m+H)$^+$=401

Example 85

Cis-N-(1-Benzoyl-6-chloro-2-methyl-1,2,3,4-tetrahydroquinolin-4-yl)-N-phenyl-acetamide $R^1$: phenyl, $R^2$: $CH_3$, $R^3$: Phenyl, $R^4$: $CH_3$, $R^5$: H, $R^6$: Cl, $R^7$: H, $R^8$: H.

To a solution of 4,6-dichloroquinoline (4 g) in methanol (50 ml) was added 1.1 eq (1.1 g) of sodium methoxyde. The mixture was heated under reflux for 17 hours. After cooling, the reaction mixture was evaporated under reduce pressure, dissolved in dichloromethane (80 ml) and washed with water (80 ml). The aqueous layer was extracted by 80 ml of dichloromethane. The organic layers were combined and dried by sodium sulfate. The solvent was evaporated to give a brown oil which was chromatographed in silicagel using $CH_2Cl_2$ and $CH_2Cl_2$/MeOH 99/1 and then 98/2. The fractions containing 4-methoxy-6-chloro-quinoline (3a) were combined and evaporated to give a brown solid (2.5 g; yield=63%).

$^1$H NMR [($CD_3$)$_2$SO]: δ 8.8 (m, 1H), 8.10 (m, 1H), 7.98 (m, 1H), 7.75 (m, 1H), 7.10 (m, 1H), 4.05 (s, 1H).

MS positive ESI: m/z (m+H)$^+$=193 (75%), 195 (25%)
HPLC: $r_T$: 4.97, 100% purity To a solution of 4-methoxy-6-chloro-quinoline (2.5 g) in tetrahydrofuran (60 ml), under nitrogen and under cooling at −78° C. (in an acetone-dry ice bath) and stirring, a solution of methyl magnesium chloride (3 mol/L) in tetrahydrofaran was dropwise added (21.4 ml) for 1 hour and then benzoyl chloride (7.5 ml) was dropwise added for 30 minutes. The mixture was stirred for 2 hours. Methanol (130 ml) and then chlorhydric acid 1 mol/L (130 ml) were added and the reaction mixture was stirred overnight. Tetrahydrofuran and methanol were evaporated under reduce pressure and the aqueous layer was extracted by dichloromethane (200 ml). After separation, the organic layer was dried by sodium sulfate, evaporated under reduced pressure and chromatographied in silicagel with dichloromethane as eluent.

The fractions containing 1-benzoyl-6-chloro-2-methyl-2,3-dihydro-1H-quinolin-4-one (3b) were combined and evaporated under reduced pressure to give a yellow solid (0.7 g; yield=18%).

$^1$H NMR [(CD$_3$)$_2$SO]: δ 8–7 (m, 9H), 5(m, 1H), 3.33 (m, 1H), 2.60 (m, 1H), 1.20 (m, 1H).

HPLC: $r_T$: 10.50, 84% purity

MS positive ESI: m/z (m+H)$^+$=299 (75%), 301 (25%)

To a solution of 1-benzoyl-6-chloro-2-methyl-2,3-dihydro-1H-quinolin-4-one (0.7 g), aniline (3eq) and triethyamine (5eq) in dichloroethane (30 ml), cooled at 0° C. in an ice bath, 1 eq of a solution of titanium chloride in toluene (1 mol/l) was dropwise added for 15 min. The mixture was heated at 85° C. during 4H30. The mixture was washed by an aqueous solution of sodium bicarbonate. The organic layer was separated, dried over sodium sulfate and the solvent was removed under reduce pressure to give a brown oil (1 g) (6-chloro-2-methyl-4-phenylimino-3,4-dihydro-2H-quinolin-1-yl)-phenyl-methanone) (3c), which was not purified.

To a solution of 6-chloro-2-methyl-4-phenylimino-3,4-dihydro-2H-quinolin-1-yl)-phenyl-methanone (0.87 g) in glacial acetic acid (35 ml) was added in small amount sodium triacetoxyborohydride (6eq) under stirring at room temperature. The reaction was stirred during 2 hours.

Ice (100 g) was added and the mixture was basified by an aqueous solution of sodium hydroxyde until pH 6 (1 mol/l, 200 ml). The aqueous solution was extracted by dichloromethane (400 ml). The organic layer was separated, dried over sodium sulfate and the solvent was removed under reduce pressure to give an amber solid. A mixture of cis/trans (6-chloro-2-methyl-4-phenylamino-3,4-dihydro-2H-quinolyn-1-yl)-phenyl-methanone (86/14) was obtained after a first chromatography on silica gel (dichloromethane).

Cis-(6-chloro-2-methyl-4-phenylamino-3,4-dihydro-2H-quinolyn-1-yl)-phenyl-methanone was obtained after a second chromatography on silica gel (cyclohexane/ethylacetate 95/5) (90 mg, yield=10.3%).

$^1$H NMR [(CD$_3$)$_2$SO]: δ 7.3 (m, 5H), 7.12 (m, 3H), 6.99 (m, 1H), 6.78(m,2H), 6.62(m,1H), 6.51 (m, 1H), 6.04 (m, NH), 4.78 (m, 1H), 4.58 (m, 1H), 2.72 (m, 1H), 1.18 (m,3H).

HPLC: $r_T$: 11.70, 97% purity

MS positive ESI: m/z (m+H)$^+$=377

A solution of Cis-(6-chloro-2-methyl-4-phenylamino-3,4-dihydro-2H-quinolyn-1-yl)-phenyl-methanone (40 mg) in dimethylformamide (1 ml) and diisopropylethylamine (3eq) was stirred during 8 hours. Acetylchloride (6 eq) was added and the reaction mixture was stirred for 72H. The solvent was evaporated in reduce pressure and the residu was dissolved in dichloromethane (10 ml). The organic layer was washed by water (10 ml), dried over sodium sulfate and evaporated under reduced pressure. The crude material was purified by chromatography on silica gel (dichloromethane/methanol 100/0 and 99/1) to afford the title compound (0.025 g, 57% yield).

$^1$H NMR [(CD$_3$)$_2$SO]:δ 7.5 (m, 2H), 7.4 (m, 5H), 7.3 (m, 2H), 7.2 (m, 2H), 7.0 (m, 1H), 6.5 (m, 1H), 5.4 (m, 1H), 4.6 (m, 1H), 2.7 (m, 1H), 1.9 (s, 3H), 1.2 (m, 1H), 1.0 (m, 3H).

HPLC: $r_T$: 10.9, 99.2% purity

MS positive ESI: m/z (m+H)$^+$=419 (75%), 421 (25%)

Example 86

Cis-N-(1-Benzoyl-7-chloro-2-methyl-1,2,3,4-tetrahydro-quinolin-4-yl)-N-phenyl-acetamide R$^1$: phenyl, R$^2$: CH$_3$, R$^3$: phenyl, R$^4$: CH$_3$, R$^5$: H, R$^6$: H, R$^7$: Cl, R$^8$: H.

The titled compound was prepared according to protocol B, using appropriate reactants and starting from 4-methoxy-7-chloro-quinoline.

(1.04 g, 70% yield)

$^1$H NMR [(CD$_3$)$_2$SO]: δ 7.5 (m, 4H), 7.4 (m, 3H), 7.3 (m, 2H), 7.2 (m, 3H), 6.6 (m, 1H), 5.4 (m, 1H), 4.6 (m, 1H), 2.7 (m, 1H), 1.9 (s, 3H), 1.3 (m, 1H), 1.0 (m,3H).

HPLC: $r_T$: 10.9, 95% purity

MS positive ESI: m/z (m+H)$^+$=419 (75%), 421 (25%)

Example 87

N-(1-Benzoyl-2-methyl-1,2,3,4-tetrahydroquinolin-4-yl)-N-prop-2-ynyl-acetamide

R$^1$: propynyl, R$^2$: CH$_3$, R$^3$: phenyl, R$^4$: CH$_3$, R$^5$: H, R$^6$: H, R$^7$: H, R$^8$: H.

To a solution of 1-benzoyl-2-methyl-2,3-dihydro-1H-quinolin-4-one (corresponds to a compound of general formula (3b) wherein R$^3$ is phenyl, R$^4$ is CH$_3$ and R$^5$, R$^6$, R$^7$, R$^8$ are H, prepared as disclosed in example 46, according to protocol B, starting from 4-chloro-quinoline, (0.3 g), triethylamine (0.92 g), propargyl amine (0.125 g) in dichloroethane (20 ml), cooled at −5° C. in an ice/sodium chloride bath, a solution of titanium chloride in toluene 1 mol/l was dropwise added for 10 minutes. The mixture was stirred over night at room temperature and then washed with dichloromethane and an aqueous solution of potassium carbonate. The organic layer was separated, dried over sodium sulfate and the solvent was removed under reduced pressure to give (2-methyl-4-prop-2-ynylimino-3,4-dihydro-2H-quinolin-1-yl)-phenyl-methanone (brown oil) (0.5 g) which was not purified, but directly used in the next step MS positive ESI: m/z (m+H)$^+$=303

To a solution of (2-methyl-4-prop-2-ynylimino-3,4-dihydro-2H-quinolin-1-yl)-phenyl-methanone (0.5 g) in acetic acid (20 ml), sodium triacetoxyborohydride was added in small amounts (1.75 g) under stirring at room temperature. The reaction mixture was then stirred at room temperature for one hour and poured on 100 ml of cold water under stirring. The desired compound was filtered after precipitation. The compound was dissolved in ethyl acetate and washed with water. The organic layer was separated and dried over sodium sulfate. The solvent was removed under reduce pressure to give a brown oil which was purified by flash chromatography with cyclohexane/ethyl acetate (95/5) as eluent and then cyclohexane/ethyl acetate (90/10) to give a mixture of diastereoisomere cis-trans (50–50) of (2-methyl-4-prop-2-ynylamino-3,4-dihydro-2H-quinolin-1-yl)-phenyl-methanone (0.06 g, 17.6% yield).

$^1$H NMR [CDCl$_3$]: δ 6.95–7.4 (m, 7H), 6.9 (t, 1H), 6.5 (d, 1H), 4.85 (m, 1H), 4.15 (m, 0.5H), 3.9 (m, 0.5H), 3.7 (s, 1H), 3.5 (d, 0.5), 3.35 (d, 0.5H), 2.8 (m, 20.5), 2.5 (m, 0.5H), 2.3 (m, 1H), 1.75 (m, 0.5H), 1.1–1.4 (m, 3.5H).

HPLC: Cis $r_T$: 5.86 min, 46.96%, purity

Trans $r_T$: 6.27 min, 47.12%, purity

MS positive ESI: m/z (m+H)$^+$=305

To a solution of (2-methyl-4-prop-2-ynylamino-3,4-dihydro-2H-quinolin-1-yl)-phenyl-methanone (0.06 g), diisopropyl ethyl amine (0.038 g) in dioxane (5 ml), anhydride acetic (0.2 g) was added under stirring. The mixture was heated under reflux over the night. After cooling dichloromethane and an aqueous solution of potassium carbonate were added. The organic layer was separated, and then dried over sodium sulfate. Organic solvent was removed under reduce pressure to give the crude compound (0.15 g). Purification by chromatography was performed with dichloromethane/methanol (99/1) as eluent to give the desired title compound (0.04 g, 58.8% yield).

MS positive ESI: m/z (m+H)$^+$=347
HPLC: Cis $r_T$: 7.628 min, 49.05%, purity
Trans $r_T$: 7.915 min, 50.95%, purity Example 88

Cis-N-(1-Benzoyl-2-methyl-1,2,3,4-tetrahydroquinolin-4-yl)-N-(4-methoxy-phenyl)-acetamide $R^1$: 4-methoxy-phenyl, $R^2$: $CH_3$, $R^3$: phenyl, $R^4$: $CH_3$, $R^5$: H, $R^6$: H, $R^7$: H, $R^8$: H.

The titled compound was prepared according to protocol B, as disclosed in example 48, using 4-methoxy-phenylamine instead of propargyl-amine in the first step.

(0.07 g, 63.6% yield)
$^1$H NMR [$(CD_3)_2SO$]: δ 7.45 (m, 1H), 7.1–7.4 (m, 9H), 7 (m, 1H), 6.9 (m, 1H), 6.5 (m, 1H), 5.5 (m, 1H), 64.65 (m, 1H),3.8 (s, 3H), 2.7 (m, 1H), 1.9 (s, 3H), 1.25 (m, 1H), 1.05 (m, 3H).
HPLC: $r_T$: 10.003, 93.8% purity
MS positive ESI: m/z (m+H)$^+$=415

Example 89

Cis-N-(1-Benzoyl-2-methyl-1,2,3,4-tetrahydroquinolin-4-yl)-N-(4-hydroxy-phenyl)-acetamide $R^1$: 4-hydroxy-phenyl, $R^2$: $CH_3$, $R^3$: phenyl, $R^4$: $CH_3$, $R^5$: H, $R^6$: H, $R^7$: H, $R^8$: H.

To a solution of Cis-N-(1-Benzoyl-2-methyl-1,2,3,4-tetrahydroquinolin-4-yl)-N-(4-methoxy-phenyl)-acetamide (0.1 g) in dichloromethane (5 ml), boron tribromide (0.18 g) was added under stirring and under cooling at −78° C. in an acetone-dry ice bath.

The mixture was stirred over night at room temperature, and then washed with dichloromethane (20 ml) and water (20 ml). The organic layer was separated, dried over sodium sulfate and the solvent was removed under reduce pressure. The crude compound was purified by flash chromatography on silica gel with an eluent dichloromethane/methanol (97/3) to give a solid (0.045 g, 46.6% yield).

$^1$H NMR [$(CD_3)_2SO$]: δ 9.7 (s, 1H), 7.1–7.4 (m, 9H), 6.9 (m, 1H), 6.8 (m, 2H), 6.5 (m, 1H),5.45 (m, 1H), 4.65 (m,1H), 2.55 (m, 1H), 1.9 (s, 3H), 1.25 (m, 1H), 1.05 (m, 3H).
HPLC: $r_T$: 8.57, 100% purity
MS positive ESI: m/z (m+H)$^+$=401

Example 90

Cis-{4-[Acetyl-(1-benzoyl-2-methyl-1,2,3,4-tetrahydroquinolin-4-yl)-amino]-phenyl}-acetic Acid Ethyl Ester $R^1$: 4-methyl acid ethyl ester-phenyl, $R^2$: $CH_3$, $R^3$: phenyl, $R^4$: $CH_3$, $R^5$: H, $R^6$: H, $R^7$: H, $R^8$: H.

The titled compound was prepared according to protocol B, as disclosed in example 48, using 4-methyl acid ethyl ester-phenylamine.

(0.1 g, 30.4% yield)

$^1$H NMR [$CDCl_3$]: δ 7.1–7.4 (m, 11H), 6.9 (m, 1H), 6.5 (m, 1H), 6.65 (m, 1H), 4.8 (m, 1H), 4.15 (m, 2H), 3.65 (s, 2H), 2.35 (m, 1H), 2.05 (m, 3H), 1.25 (m, 4H), 1.1 (m, 3H).
HPLC: $r_T$: 10.42, 95.73% purity
MS positive ESI: m/z (m+H)$^+$=471

Example 91

Cis-N-(1-Benzoyl-2-methyl-1,2,3,4-tetrahydroquinolin-4-yl)-N-phenyl-malonamic Acid Methyl Ester $R^1$: phenyl, $R^2$: $CH_2$—$COOCH_3$, $R^3$: phenyl, $R^4$: $CH_3$, $R^5$: H, $R^6$: H, $R^7$: H, $R^8$: H.

The titled compound was prepared according to protocol B, using appropriate reactants. (0.1 g, 77.5% yield)
$^1$H NMR [$(CD_3)_2SO$]: δ 7.65 (m, 1H), 7.05–7.6 (m, 11H), 6.95 (m, 1H), 6.5 (m, 1H), 5.5 (m, 1H), 4.65 (m, 1H), 3.6 (s, 3H), 3.35 (m, 2H), 2.55 (m, 1H), 1.2 (m, 1H), 1 (m, 3H).
HPLC: $r_T$: 10.3, 100% purity
MS positive ESI: m/z (m+H)$^+$=442

Example 92

Cis-N-(1-Benzoyl-2-methyl-1,2,3,4-tetrahydroquinolin-4-yl)-N-phenyl-malonamic Acid $R^1$: phenyl, $R^2$: $CH_2$—COOH, $R^3$ phenyl, $R^4$: $CH_3$, $R^5$: H, $R^6$: H, $R^7$: H, $R^8$: H.

To a solution of Cis-N-(1-Benzoyl-2-methyl-1,2,3,4-tetrahydroquinolin-4-yl)-N-phenyl-malonamic acid methyl ester (0.031 g) in a mixture of methanol (1 ml) and water (1 ml), 0.0067 g of lithium hydroxide was added under stirring at room temperature, over night. In order to complete the reaction, 0.0067 g of lithium hydroxide was added and the mixture was stirred over night. Then dichloromethane and an aqueous solution of sodium bicarbonate were added, the organic layer was separated, dried over sodium sulfate, the solvent was removed under reduce pressure to give a solid which was purified by flash chromatography with dichloromethane/methanol (95/5) as eluent to give a solid (0.01 g, 33.3% yield).

HPLC: $r_T$: 9.09, 100% purity
MS positive ESI: m/z (m+H)$^+$=427

Example 93

Cis-N-[2-Methyl-1-(pyridine-3-carbonyl)-1,2,3,4-tetrahydroquinolin-4-yl]-N-phenyl-acetamide $R^1$: phenyl, $R^2$: $CH_3$, $R^3$: pyridin-3-yl, $R^4$: $CH_3$, $R^5$: H, $R^6$: H, $R^7$: H, $R^8$: H.

A mixture of 4-chloroquinoline (10 g) and aniline (11.4 g) was warmed to 150° C. for 30 min. A solution of sodium hydroxide 1 N (200 ml) was added. After extraction with ethyl acetate (1 L), the organic layer was separated and dried over sodium sulfate. The solvent was removed to afford an amorphous materiel, which was crystallized in cyclohexane. Phenyl-quinolin-4-yl-amine (13.7 g) was obtained after filtration.

$^1$H NMR [$(CD_3)_2SO$]: δ 8.95 (s, 1H), 8.45 (d, 1H), 8.35 (d, 1H), 7.9 (m, 1H), 7.7 (m, 1H), 7.55 (m, 1H), 7.4 (m, 4H), 7.15 (m, 1H), 6.95 (m, 1H).

To a solution of phenyl-quinolin-4-yl-amine (13 g) and N-ethyl-N,N-diisopropylamine (1.5 eq) in dioxane (105 ml) was added acetic anhydride (28.1 ml, 5 eq). The solution was warmed to reflux of dioxane for 5 days. After cooling, dichloromethane was added and the solution was washed by water and sodium hydroxide 1N. The organic layer was separated and dried over sodium sulfate. The solvent was removed and the mixture was purified by chromatography on silica gel (dichloromethane/ethanol (95:5)) to afford N-phenyl-N-quinolin-4-yl-acetamide (10 g).

$^1$H NMR [(CD$_3$)$_2$SO]: δ 9.0 (m, 1H), 8.1 (m, 2H), 7.8 (m, 1H), 7.65 (m, 1H), 7.55–7.3 (m, 6H), 2.2–2.0 (m, 3H).

A solution of N-phenyl-N-quinolin-4-yl-acetamide (2 g) and benzyle bromide (1.3 g) in acetone was warmed to reflux for 5 days. The solvent was removed to afford an amorphous material, which was crystallized in diethyl ether. 4-[Acetyl-(phenyl)-amino]-1-benzylquinolinium bromide (2 g) was obtained by filtration.

$^1$H NMR [(CD$_3$)$_2$SO]: δ 9.75 (d, 1H), 8.45 (q, 2H), 8.2 (m, 2H), 8.0 (m, 1H), 7.65 (m, 2H), 7.55–7.35 (m, 8H), 6.3 (s, 2H), 2.2 (s, 3H).

To a suspension of 4-[(acetyl)(phenyl)amino]-1-benzylquinolinium bromide (200 mg) in tetrahydrofuran, under cooling at −78° C. in an acetone-dry ice bath and under stirring, a solution of methyl magnesium chloride at 3M/l was dropwise added. The suspension became homogenous. At −78° C., a mixture of methanol and water were added, and then extracted with ethyl acetate. The organic layer was separated, dried over sodium sulfate. The solvent was removed under reduced pressure to give the desired compound (150 mg).

$^1$H NMR [(CD$_3$)$_2$SO]: δ 7.5–7.15 (m, 10H), 7.0–6.9 (m, 2H), 6.5 (m, 2H), 6.1 (m, 1H), 4.3 (m, 1H), 2.1 (2m, 3H), 1.15 (d, 3H).

A solution of N-(1-benzyl-2-methyl-1,2-dihydroquinolin-4-yl)-N-phenylacetamide (100 mg) and (R,R)-(−)-1,2-bis[(o-methoxyphenyl)(phenyl)phosphino]ethane(1,5-cyclooctadiene)rhodium (I) tetrafluoroborate (20 mg) in methanol (6 ml) was stirred under 20 bars of hydrogene overnight. Dichloromethane was added and the organic layer was washed by water and dried over sodium sulfate. The solvent was removed and the mixture was purified by chromatography on silica gel (dichloromethane/ethanol (99:1)) to afford N-(1-benzyl-2-methyl-1,2,3,4-tetrahydroquinolin-4-yl)-N-phenylacetamide (80 mg).

$^1$H NMR [(CDCl$_3$)]: δ 7.35–7.1 (m, 11H), 7.0 (t, 1H), 6.7 (t, 1H), 6.4 (d, 1H), 6.2 (m, 1H), 4.4 (dd, 2H), 3.6 (m, 2H), 1.9 (m+s, 4H), 1.5 (m, 1H), 1.05 (d, 3H).

A solution of N-(1-benzyl-2-methyl-1,2,3,4-tetrahydroquinolin-4-yl)-N-phenylacetamide (50 mg) and ammonium formate (85 mg) and palladium on activated carbon 10% in ethanol (2 ml) were warmed to reflux for 1 hour. The solution was filtered on celite and the solvent was removed to afford N-(2-methyl-1,2,3,4-tetrahydroquinolin-4-yl)-N-phenylacetamide (40 mg).

$^1$H NMR [(CDCl$_3$)]: δ 7.25 (m, 4H), 7.0 (m, 3H), 6.75 (t, 1H), 6.45 (d, 1H), 6.3 (m, 1H), 3.55 (m, 2H), 1.9 (m+s, 4H), 1.35 (m, 1H), 1.1 (d, 3H).

Nicotinoyl chloride (1.1 eq) was added to a solution of N-(2-methyl-1,2,3,4-tetrahydroquinolin-4-yl)-N-phenylacetamide (100 mg) and N-ethyl-N,N-diisopropylamine (2.2 eq) in dioxane (1 ml). The mixture was stirred overnight at room temperature. Dichloromethane was added and the organic layer was washed by water and sodium carbonate solution and dried over sodium sulfate. The solvent was removed and the mixture was purified by chromatography on silica gel (dichloromethane and ethanol (99:1)) to afford the title compound (30 mg).

1H NMR [CDCl3]: d 8.6 (s, 1H), 8.5 (d, 1H), 7.4–7.2 (m, 8H), 7.1 (m, 1H), 6.9 (t, 1H), 6.45 (d, 1H), 5.6 (m, 1H), 4.8 (m, 1H), 2.3 (m, 1H), 2.0 (s, 3H), 1.1 (d+m, 4H).

HPLC: r$_T$: 8.11, 97.2% purity

MS positive ESI: m/z (m+H)$^+$=386

Example 94

Cis-N-(1-Benzoyl-2-methyl-1,2,3,4-tetrahydroquinolin-4-yl)-N-Cyclopropyl-acetamide R$^1$: cyclopropyl, R$^2$: CH$_3$, R$^3$: phenyl, R$^4$: CH$_3$, R$^5$: H, R$^6$: H, R$^7$: H, R$^8$: H.

The titled compound was prepared according to protocol C, using appropriate reactants.

(0.24 g, 47% yield)

$^1$H NMR [(CD$_3$)$_2$SO]: δ 6.75–7.4 (m, 8H), 6.5 (m, 1H), 5.35 (m, 1H), 4.7 (m, 1H), 2.8 (m, 1H), 2.5 (m, 1H), 2.3 (m, 3H), 1.9 (m, 1H), 1.3 (m, 3H), 1.1 (m, 1H), 1 (m, 1H), 0.75 (m, 1H), 0.55 (m, 1H).

HPLC: 99.55%, purity

MS positive ESI: m/z (m+H)$^+$=349

Example 95

Cis-N-Cyclopropyl-N-[2-methyl-1-(pyridine-3-carbonyl)-1,2,3,4-tetrahydroquinolin-4-yl]-acetamide R$^1$: cyclopropyl, R$^2$: CH$_3$, R$^3$: pyridin-3-yl, R$^4$: CH$_3$, R$^5$: H, R$^6$: H, R$^7$: H, R$^8$: H.

A mixture of 4-chloroquinoline (13.9 g) and cyclopropyl amine (9.7 g) was heated at 180° C. under stirring for 16 hours. After cooling, a solution of sodium hydroxide 1N (200 ml) was added. After extraction with dichloromethane (200 ml), the organic layer was separated and dried over sodium sulfate. The solvent was removed under reduce pressure to afford an oil, which was crystallized in acetonitrile (50 ml). Cyclopropyl-quinolin-4-yl-amine (6.6 g; 42% yield) was obtained after filtration.

$^1$H NMR [(CD$_3$)$_2$SO]: δ 8.5 (m, 1H), 8.2 (m, 1H), 7.8 (m, 1H), 7.6 (m, 1H), 7.4 (m, 1H), 6.8 (m, 1H), 2.6 (m, 1H), 0.85 (m, 2H), 0.6 (m, 2H).

HPLC: r$_T$: 5.7, 100% purity

Acetic anhydride (18.3 g) was added to a solution of cyclopropyl-quinolin-4-yl-amine (6.6 g) in pyridine (50 ml) and the mixture was heated under reflux over night. After cooling, the solvent was removed under reduce pressure and then the mixture was washed with dichloromethane (200 ml) and an aqueous solution of sodium carbonate (200 ml). The organic layer was separated and dried over sodium sulfate. The solvent was removed under reduce pressure and the crude compound was purified by flash chromatography on silicagel using dichloromethane/methanol (98/2) as eluent to give cyclopropyl-quinolin-4-yl-acetamide (8 g, 98.7% yield).

$^1$H NMR [(CD$_3$)$_2$SO]: δ (T=400 K) 8.9 (m, 1H), 8.1 (m, 1H), 7.7–7.85 (m, 2H), 7.6 (m, 1H), 7.35 (m, 1H), 3.4 (m, 1H), 2.1 (s, 3H), 0.85 (m, 2H), 0.55 (m, 2H).

MS positive ESI: m/z (m+H)$^+$=227

Benzyl bromide (16.71 g) was added to a solution of cyclopropyl-quinolin-4-yl-acetamide (7.37 g) in acetone (50 ml). The mixture was heated 3 days under reflux. After cooling, the solid was filtered, washed with acetone (20 ml) and dried to give the 4-(acetyl-cyclopropyl-amino)-1-benzyl-quinolinium bromide (10.6 g, 81.7% yield).

$^1$H NMR [CDCl$_3$]: δ 10.7 (d, 1H), 8.4 (m, 1H), 8.2 (m, 1H), 8.05 (m, 1H), 7.95 (m, 1H), 7.8 (m, 1H), 7.3–7.5 (m, 5H), 6.6 (s, 2H), 3.6 (m, 1H), 2.6 (s, 3H), 1.2 (m, 2H), 0.75 (m, 2H).

HPLC: r$_T$: 6.69, 100% purity

To a mixture of 4-(acetyl-cyclopropyl-amino)-1-benzyl-quinolinium bromide (9.6 g) in tetrahydrofuran (200 ml), under nitrogen and under cooling at 0° C., a solution of methyl magnesium chloride 1 Mol/l (12 ml) was added during 15 minutes. After 2 hours, a solution of ammonium chloride in methanol (100 ml) was added. The solvent was removed under reduce pressure and then washed with dichloromethane and water. The organic layer was separated and the solvent was removed under reduce pressure. The crude compound was purified by flash chromatography on silicagel with an eluent of dichloromethane/methanol (98/2) to give the N-(1-benzyl-2-methyl-1,2-dihydro-quinolin-4-yl)-N-cyclopropyl-acetamide (7.9 g, 98.6% yield).

$^1$H NMR [CDCl$_3$]: δ 7.3 (m, 6H), 7.1 (m, 1H), 6.95 (m, 1H), 6.65 (m, 1H), 6.5 (m, 1H), 5.45 (m, 1H), 4.6 (m, 1H), 4.35 (m, 1H), 4.2 (m, 1H), 3.2 (m, 1H), 2.05 (m, 3H) 1.2 (m, 3H), 0.8 (m, 2H), 0.55 (m, 2H).

HPLC: r$_T$: 10.9, 100% purity

To a solution of N-(1-benzyl-2-methyl-1,2-dihydro-quinolin-4-yl)-N-cyclopropyl-acetamide (7.5 g) in methanol (160 ml) and tetrahydrofuran (375 ml), nickel chloride hexahydrate (5.4 g) was added. After cooling at 0° C., sodium borohydride (3.41 g) was added in small portions, and then the mixture was stirred at room temperature overnight. Dichloromethane and water were added to the mixture. The organic layer was separated and the solvent was removed under reduce pressure. The crude compound was purified by flash chromatography on silicagel using cyclohexane/methanol (90/10), then (80/20), then (70/30) to give the Cis-N-(1-benzyl-2-methyl-1,2,3,4-tetrahydroquinolin-4-yl)-N-cyclopropyl-acetamide (3.9 g, 51.7% yield).

$^1$H NMR [CDCl$_3$]: δ 7.3 (m, 5H), 6.95 (m, 1H), 6.7 (m, 1H), 6.55 (m, 1H), 6.45 (m, 1H), 5.9 (m, 1H), 4.5 (dd, 2H) 3.65 (m, 1H), 2.65 (m, 1H), 2.5 (m, 1H), 2.4 (s, 3H), 1.25 (m, 3H), 0.6–0.9 (m, 4H).

To a solution of Cis-N-(1-benzyl-2-methyl-1,2,3,4-tetrahydroquinolin-4-yl)-N-cyclopropyl-acetamide (3.8 g) in ethanol (150 ml), ammonium formate (7.2 g) and few milligrams of palladium on charcoal (10% Pd/C) were added. The mixture was heated under reflux for 2 hours. After cooling the mixture was filtered on celite and the solvent was removed under reduce pressure to give Cis-N-cyclopropyl-N-(2-methyl-1,2,3,4-tetrahydroquinolin-4-yl)-acetamide (2.56 g, 92.4% yield) which was not purified.

HPLC: r$_T$: 7.62, 99.06% purity

Nicotinoyl chloride hydrochloride (1.46 g) was added to a solution of Cis-N-cyclopropyl-N-(2-methyl-1,2,3,4-tetrahydroquinolin-4-yl)-acetamide (0.4 g) in pyridine (20 ml). The mixture was heated at 50° C. for 3 hours. After cooling, an aqueous solution of sodium carbonate was added and the mixture was extracted with ethyl acetate. The organic layer was dried over sodium sulfate, and then the solvent was removed under reduce pressure. The crude compound was crystallized in diethyl ether to give Cis-N-cyclopropyl-N-[2-methyl-1-(pyridine-3-carbonyl)-1,2,3,4-tetrahydroquinolin-4-yl]-acetamide (0.3 g, 52.6% yield).

$^1$H NMR [CDCl$_3$]: d 8.5 (s, 1H), 8.4 (3, 1H), 7.15–6.7 (m, 5H), 6.4 (d, 1H), 5.4 (m, 1H), 4.8 (m, 1H), 2.6 (m, 2H), 2.3 (s, 3H), 1.9 (m, 1H), 1.2 (m, 3H), 1.0–0.7 (m, 4H)

HPLC: r$_T$: 6.39, 98.3% purity

MS positive ESI: m/z (m+H)$^+$=350

Example 96 and 97

(+)-Cis-N-cyclopropyl-N-[2-methyl-1-(pyridine-3-carbonyl)-1,2,3,4-tetrahydroquinolin-4-yl]-acetamide (Example 57) and (–)-Cis-N-cyclopropyl-N-[2-methyl-1(pyridine-3-carbonyl)-1,2,3,4-tetrahydroquinolin-4-yl]-acetamide (Example 58)

The racemic Cis-N-cyclopropyl-N-[2-methyl-(pyridine-3-carbonyl)-1,2,3,4-tetrahydroquinolin-4-yl]-acetamide (0.05 g) was separated by preparative high performance liquid chromatography following the conditions:
Column: Chiralpak AS-H 20*250 mm, 5μ
Mobile phase: 70 Hexane (0.2% Diethyl amine)
30 EtOH (0.2% Diethyl amine)
Detection: 254 nm After separation, and concentration, the following products were obtained:

(+)-Cis-N-cyclopropyl-N-[2-methyl-1 (pyridine-3-carbonyl)-1,2,3,4-tetrahydroquinolin-4-yl]-acetamide (0.147 g)
HPLC r$_T$: 9.16 min, ee>99%, purity
[α]$_D^{20}$=+249°, (c=0.122, MeOH)

(–)-Cis-N-cyclopropyl-N-[2-methyl-1 (pyridine-3-carbonyl)-1,2,3,4-tetrahydroquinolin-4-yl]-acetamide (0.147 g)
HPLC r$_T$: 9.18 min, ee=94.26%, purity
[α]$_D^{20}$=–227°, (c=0.079, MeOH)

Example 98

Cis-N-Cyclopropyl-N-[2-methyl-1-(3-methyl-isoxazole-5-carbonyl)-1,2,3,4-tetrahydroquinolin-4-yl]-acetamide R$^1$: cyclopropyl, R$^2$: CH$_3$, R$^3$: 3-methyl-isoxazol-5-yl, R$^4$: CH$_3$, R$^5$: H, R$^6$: H, R$^7$: H, R$^8$: H.

The titled compound was prepared according to protocol C, using appropriate reactants.

1H NMR [CDCl3]: d 7.15–6.7 (m, 5H), 5.35 (m, 1H), 4.9 (m, 1H), 2.8 (m, 1H), 2.5 (m, 1H), 2.4–2.2 (m, 6H), 1.9 (m, 1H), 1.3 (m, 3H), 1.0–0.7 (m, 4H).

HPLC: r$_T$: 7.97, 98.6% purity

MS positive ESI: m/z (m+H)$^+$=354

Example 99

Cis-N-Phenyl-N-1-(thiophene-2-carbonyl)-1,2,3,4-tetrahydroquinolin-4-yl]-acetamide R$^1$: phenyl, R$^2$: CH$_3$, R$^3$: thien-2-yl, R$^4$: H, R$^5$: H, R$^6$: H, R$^7$: H, R$^8$H.

To a solution of N-phenyl-N-quinolin-4-ylacetamide (2 g) and Nickel dichloride (7.6 mmol) in methanol, cooled at 0° C., was added sodium borohydride (20 eq). The solution was then stirred overnight, at room temperature. The solvent was removed to give an amorphous materiel, which is crystallized in diethyl ether. After fitration, dichloromethane was added and the solution was washed with water. The organic layer was separated and dried over sodium sulfate. The solvent was removed to obtain an amorphous material. The product was purified by chromatography on silica gel using a mixture of cyclohexane and ethyl acetate (95:5) as eluent to give a N-phenyl-N-1,2,3,4-tetrahydroquinolin-4-ylacetamide (380 mg).

1H NMR [CDCl3]: d 7.45 (m, 2H), 7.2 (m, 2H), 7.0 (m, 1H), 6.9 (m, 1H), 6.8 (s, 1H), 6.6 (t, 1H), 6.3 (d, 1H), 6.1 (t, 1H), 3.55 (m, 1H), 3.15 (m, 1H), 2.75 (m, 1H), 2.05 (s, 3H), 1.95 (m, 1H), 1.75 (m, 1H).

To a solution of N-phenyl-N-1,2,3,4-tetrahydroquinolin-4-ylacetamide (100 mg) and N-ethyl-N,N-diisopropylamine (1.5 eq) in dioxane (2 ml), was added 2-thiophenecarbonyl chloride (1.5 eq). The mixture was stirred overnight at room temperature. After addition of dichloromethane, the organic layer was washed with water and a sodium hydroxide solution and then dried over sodium sulfate. The solvent was removed to give an amorphous material, which was crystallized in diethylether to give the title compound (80 mg).

1H NMR [CDCl3]: d 7.45 (d, 1H), 7.3–7.2 (m, 4H), 7.05 (t, 1H), 6.9 (m, 3H), 6.7 (m, 2H), 6.5 (d, 1H), 6.2 (t, 1H), 4.0 (m, 1H), 3.5 (m, 1H), 2.2 (m, 1H), 2.0 (m, 1H), 1.85 (s, 3H).

HPLC: $r_T$: 10.02, 97.8% purity

MS positive ESI: m/z (m+H)$^+$=377

Example 100

Cis-N-(1-Benzoyl-1,2,3,4-tetrahydroquinolin-4-yl)-N-phenyl-acetamide $R^1$: phenyl, $R^2$: $CH_3$, $R^3$: phenyl, $R^4$: H, $R^5$: H, $R^6$: H, $R^7$: H, $R^8$: H.

The titled compound was prepared according to protocol C, using appropriate reactants.

1H NMR [CDCl3]: d 7.45 (d, 1H), 7.3–7.2 (m, 4H), 7.1 (t, 2H), 7.0 (t, 1H), 6.9 (m, 4H), 6.8 (t, 1H), 6.4 (m, 1H), 6.3 (t, 1H), 4.1 (m, 1H), 3.4 (m, 1H), 2.2 (m, 1H), 2.0 (m, 1H), 1.85 (s, 3H).

HPLC: $r_T$: 10.12, 98.6% purity

MS positive ESI: m/z (m+H)$^+$=371

Example 101

Cis-N-[2-Ethyl-1-(pyridine-3-carbonyl)-1,2,3,4-tetrahydroquinolin-4-yl]-N-phenyl-acetamide $R^1$: phenyl, $R^2$: $CH_3$, $R^3$: pyridin-3-yl, $R^4$: ethyl, $R^5$: H, $R^6$: H, $R^7$: H, $R^8$: H.

The titled compound was prepared according to protocol C, using appropriate reactants.

$^1$H NMR [CDCl$_3$]: δ 8.5 (m, 2H), 7.4–7.1 (m, 8H), 7.0 (m, 1H), 6.9 (t, 1H), 6.4 (d, 1H), 5.5 (m, 1H), 4.6 (m, 1H), 2.3 (m, 1H), 2.0 (s, 3H), 1.6 (m, 1H), 1.3 (m, 2H), 0.7 (t, 3H).

HPLC: $r_T$: 8.63, 96.7% purity

MS positive ESI: m/z (m+H)$^+$=400

Example 102

Cis-N-Ethyl-N-[2-Methyl-1-(pyridine-3-carbonyl)-1,2,3,4-tetrahydroquinolin-4-yl]-acetamide $R^1$: $CH_2$—$CH_3$, $R^2$: $CH_3$, $R^3$: pyridin-3-yl, $R^4$: $CH_3$, $R^5$: H, $R^6$: H, $R^7$: H, $R^8$: H.

The titled compound was prepared according to protocol C, using appropriate reactants.

(0.046 g, 60% yield)

$^1$H NMR [CDCl$_3$]: δ 8.5 (m, 2H), 7.3 (m, 1H), 7.2 (m, 1H), 7.1 (m, 1H), 7.0 (m, 1H), 6.9 (m, 1H), 6.5 (m, 1H), 5.9 (m, 0.5H), 4.9 (m, 1.5H), 4.0 (m, 0.2H), 3.6 (m, 0.4H), 3.2 (m, 0.4H), 2.8 (m, 1H), 2.6 (m, 0.5H), 2.3 (m, 1.5H), 2.2 (m, 1.5H), 1.7 (m, 0.5H), 1.4 (m, 3H), 1.2 (m, 3H).

HPLC: $r_T$: 5.87, 100% purity

MS positive ESI: m/z (m+H)$^+$=338

BIOLOGICAL RESULTS

Binding Test

The binding of CRTH2 antagonists was measured using membranes prepared from CRTH2-expressing L1.2 cells. To make the membrane preparation, 10 grams of cell pellet were resuspended in 20 ml of cold 50 mM Tris HCl (pH 7.7), and homogenized three times (10 seconds each) on ice with a Polytron tissue homogenizer. The suspension was then diluted to 80 ml with the same buffer, and centrifuged at 40,000×g for 30 min. After discarding the supernatant, the pellet was washed once with cold 80 mM Tris HCl (pH 7.7) by repeating the resuspension, homogenization, and centrifugation described above. Finally, the pellet was resuspended in 20 ml of cold 50 mM Tris HCl (pH 7.7), aliquoted, and stored at −80° C. On the day of the assay, the membranes were thawed on ice, and 25 μl was placed into each well of a 96-well microtiter plate. 5 μl of 0.5 M MgCl$_2$ and 10 μl of PVT-WGA scintillation proximity assay (SPA) beads (Amersham) were then added to each well and mixed thoroughly. 5 μl of the compounds to be tested were then added, followed by 5 μl of 30 nM $^3$H-PGD$_2$ (200 Ci/mmol from NEN diluted 1:17) to initiate the binding reaction. The plate is then sealed and incubated at room temperature for at least 1 hour before being counted on a Wallac Microbeta Trilux scintillation counter. Non-specific binding is measured in wells containing 100 μM unlabeled PGD$_2$. Active compounds are able to compete with $^3$H-PGD$_2$ for binding to CRTH2 and are identified by a decrease in the number of cpm bound.

The compounds of the invention were tested in the above assay and were found to be active CRTH2 antagonists. The IC$_{50}$ values of compounds of examples 1 to 102 are below 5 μM.

Actin Polymerization Test

Actin polymerization was assayed using an actin-specific fluorescent label, phalloidin-fluorescein isocyanate conjugate, which binds polymerized actin fiber. This test can be performed using cells such as isolated human eosinophils or isolated human TH2-cells. The cells (preparations were resuspended at 1.1×10$^6$ cells/ml in RPMI 1640+ pen/strep+ 0.5% FCS. The cell suspension was aliquoted (450 μl/tube) into 5 ml tube. The cells were incubated 2 min at 37° C. with the cells and then the appropriate stimulus (PGD$_2$) was added followed exactly 25 seconds later by 500 μL of stopping solution, which contains lysophosphatidylcholine (0.5 mg/ml), PBS, 6 to 8% formaldehyde, and 0.2 μM NBD-phallacidin in MEOH. The tube was allowed to sit at 4° C. for an hour. The tube was then centrifuged at 1400 rpm for 5 minutes. The cell pellets were washed twice and then resuspended in 500 μl PBS. Each sample was then read on a FACS Caliber instrument. Cells were gated using the forward scatter/side scatter data in the lymphocyte area. Responses were measured by the change in median FL-1 fluorescence between vehicle treated cells and stimulus treated cells. Test compounds were assayed in the presence and absence of PGD$_2$, and compared to a sample containing PGD$_2$ alone. A compound that reduces PGD$_2$-induced actin polymerization of CRTH2 cells is identified as a candidated CRTH2 antagonist.

The invention claimed is:

1. A compound of formula (I):

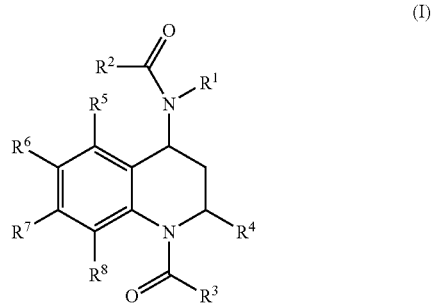

wherein
R¹ is H, $(C_1-C_4)$alkyl, $(C_2-C_4)$alkenyl, $(C_2-C_4)$alkynyl or $(CH_2)_m$—R¹, in which
R¹¹ is selected from aromatic heterocycle, phenyl and $(C_3-C_6)$cycloalkyl wherein the phenyl, the heterocycle and the cycloalkyl groups are unsubstituted or substituted by one to three groups independently selected from
Q¹, and
$(C_1-C_4)$alkyl optionally substituted with one to three groups which are the same or different and which are selected from Q¹,
wherein Q¹ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R_{10}$ are the same or different and are selected from H and $(C_1-C_4)$alkyl;
m is an integer selected from 0, 1 and 2;
R² is $(C_1-C_4)$alkyl, wherein the alkyl group is substituted with one to three substituents independently selected from halogen, $OR^9$, $NR^9R^{10}$, $COOR^9$, $C(=O)NR^9R^{10}$, $NHSO_2R^9$ and $C(=O)$ $(C_1-C_4)$alkyl;
R³ is $(C_3-C_6)$cycloalkyl or -A- R¹³, wherein
A is a bond, $(C_1-C_3)$alkylene or $(C_2-C_3)$alkenylene;
R¹³ is $(C_6-C_{12})$aryl or a 5- to 10-membered heterocycle, optionally aromatic, wherein the aryl and the heterocycle groups are unsubstituted or substituted by one to three substituents independently selected from $(C_6-C_{12})$aryl, 2,2,2-trifluoro-N-phenyl-N-[1,2,3,4-tetrahydro-1-(3-methoxybenzoyl)-2-methyl-4-quinolinyl]-acetamide,
N-(1-benzoyl-1,2,3,4-tetrahydro-2-methyl-4-quinolinyl)-N-(3-methoxyphenyl)-acetamide,
N-(1-benzoyl-1,2,3,4-tetrahydro-2-methyl-4-quinolinyl)-N-(4-methylphenyl)-acetamide,
N-[1-(4-chloro-3-nitrobenzoyl)-1,2,3,4-tetrahydro-2-methyl-4-quinotinyl]-Nphenyl-acetamide,
N-phenyl-N-[1,2,3,4-tetrahydro-2-methyl-1-(3-nitrobenzoyl)-4-quinolinyl]-acetamide,
N-phenyl-N-1,2,3,4-tetrahydro-1-3-(4-methoxyphenyl)-1-oxo-2-propenyl]-2-methyl-4-quinolinyl]-acetamide,
N-[1-(3-chlorobenzoyl)-1,2,3,4-tetrahydro-2-methyl-4-quinolinyl]-N-phenylacetamide,
N-[1-(3-fluorobenzoyl)-1,2,3,4-tetrahydro-2-methyl-4-quinolinyt]-N-phenylacetamide,
N-[1-[4-(1,1-dimethylethyl)benzoyl]-1,2,3,4-tetrahydro-2-methyl-4-quinolinyl]-N-phenyl-acetamide,
N-phenyl-N-[1,2,3,4-tetrahydro-2-methyl-1-(1-oxo-3-phenyl-2-propenyl)-4-quinolinyl]-acetamide,
N-phenyl-N-[1>2,3,4-tetrahydro-2-methyl-1-(2-thienylcarbonyl)-4-quinolinyl]-acetamide,
N-phenyl-N-[1,2,3,4-tetrahydro-1-(4-methoxybenzoyl)-2-methyl-4-quinolinyl]-acetamide,
N-[1-(3,5-dinitrobenzoyl)-1,2,3,4-tetrahydro-2-methyl-4-quinolinyl]-N-phenylacetamide,
N-phenyl-N-[1,2,3,4-tetrahydro-2-methyl-1 -(4-nitrobenzoyl)-4-quinolinyl]-acetamide,
N-phenyl-N-[1,2,3I4-tetrahydro-1-(2-iodobenzoyl)-2-methyl-4-quinolinyl]-acetamide,
N-phenyl-N-[1,2,3,4-tetrahydro-1-(3-methoxybenzoyl)-2-methyl-4-quinolinyl]-acetamide,
N-(1benzoyl-1,2,3,4-tetrahydro-2-methyl-4-quinolinyl)-N-phenyl-pentanamide,
N-(1-benzoyl-1,2,3,4-tetrahydro-2-methyl-4-quinolinyl)-N-phenyl-butan amide,
N-(1-benzoyl-1,2,3,4-tetrahydro-2-methyl-4-quinolinyl)-N-phenyl-propanarnide,
1-benzoyl-1,2,3,4-tetrahydro-4-(N-phenylacetamido)-quinaldine,
N-[(1-benzoyl-1,2,3,4-tetrahydro-2-methyl-4-quinolinyl]-2-methyl-N-phenyl propanamide;
N-[1-(4-bromobenzoyl)-1,2,3,4-tetrahydro-2,6-dimethyl-4-quinolinyl]-acetamide;
N-(1-benzoyl-1,2,3,4-tenahydro-2,6-dimethyl-4-quinoUnyl)-acetamide; and
N-(1-benzoyl-1,2,3,4-tetrahydro-2-methyl-4-quinolinyl)-acetamide.

2. A compound of formula (Ia) or formula (Ib), or a racemic mixture of formula (Ia) and (Ib):

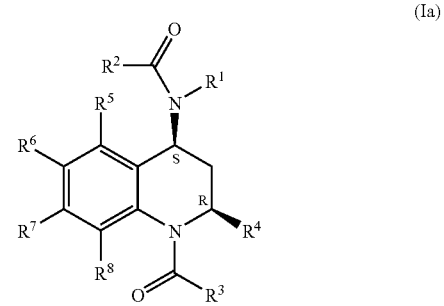

(Ia)

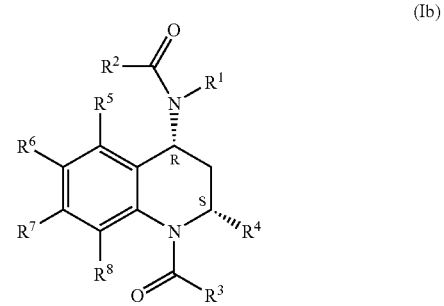

(Ib)

R¹ is H, $(C_1-C_4)$alkyl, $(C_2-C_4)$alkenyl, $(C_2-C_4)$alkynyl or $(CH_2)_m$-R¹, in which R¹ is elected from aromatic heterocycle, phenyl and $(C_3-C_6)$cycloalkyl wherein the phenyl, the heterocycle and the cycloalkyl groups are unsubstituted or substituted by one to three groups independently selected from Q¹, and $(C_1-C_4)$alkyl optionally substituted with one to three groups which are the same or different and which are selected from Q¹, wherein Q¹ is selected from halogen, $NO_2$, CN, $SO_2CH_3$, $SO_2$, $NR^9R^{10}$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl;

m is an integer selected from 0, 1 and 2;

R² is $(C_1-C_4)$alkyl, wherein the alkyl group is substituted with one to three substituents independently selected from halogen, $OR^9$, $NR^9R^{10}$, $COOR^9$, $C(=O)NR^9R^{10}$, $NHSO_2R^9$ and $C(=O)$ $(C_1-C_4)$alkyl;

R³ is $(C_3-C_6)$cycloalkyl or —A—R³, wherein

A is a bond, $(C_1-C_3)$alkylene or $(C_2-C_3)$alkenylene;

$R^3$ is $(C_6-C_{12})$aryl or a 5 to 10-membered heterocycle, optionally aromatic, wherein the aryl and the heterocycle groups are unsubstituted or substituted by one to three substituents independently selected from $(C_6-C_{12})$aryl, an aromatic heterocyle, $Q^2$, and $(C_1-C_4)$alkyl optionally substituted with one to three groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(=O)R^{10}$ and $C(=O)R^9$;

$R_4$ is 1 $(C_1-C_4)$-alkyl;

$R^5$, $R^6$, $R^7$ and $R^8$ are the same or different and are selected from

H, $Q^3$, and $R_4$ is 1$(C_1-C_4)$-alkyl;

$R^5$, $R^6$, $R^7$ and $R^8$ are the same or different and are selected from

H, $Q^3$, and $(C_1-C_4)$alkyl optionally substituted with one to three groups which are the same or different and which are selected from $Q^3$, wherein $Q^3$ is selected from halogen, $NO_2$, CN, $SO_2CH_3$, $SO_2NR^9R^{10}$, $OR^9$, $SR^9$, $COOR^9$, $C(=O))NR^9R^{10}$, $NR^9R^{10}$, $NR^9SO_2R^{10}$, $NR^9C(=O)R^{10}$ and $C(=O)R^9$;

an N-oxide thereof or a pharmaceutically acceptable salt of the compound or N-oxide; with the proviso that the following compounds are excluded:

N-[(2R,4S)-1-benzoyl-1,2,3,4-tetrahydro-2-methyl-4-quinolinyl]-2-methyl-Nphenyl propanamide;

N-[(2R,4S)-1-benzoyl-1,2,3yl-1,2,3)4-tetrahydro-2-methyl-4-quinolinyl]-2,2-dimethyl-Nphenyl-propanamide;

N-[(2R,4S)-1-benzoyl-1,2,3,4-tetrahydro-2-methyl-4-quinolinyl]-N-phenyl butanamide;

N-[(2R,4S)-1-benzoyl-1,2,3,4-tetrahydrp-2-methyl-4-quinolinyl]-N-phenyl acetamide;

N-[(2R,4S)-1-benzoyl-1,2,3,4-tetrahydro-2-methyl-4-quinolinyl]-N-phenylpentanamide; and N-[(2R,4S)-1-benzoyl-1,2,3,4-tetrahydro-2-methyl-4-quinolinyl]-acetamide.

3. A compound of formula (Ic) or formula (Id), or is a racemic mixture of formula (Ic) and (Id):

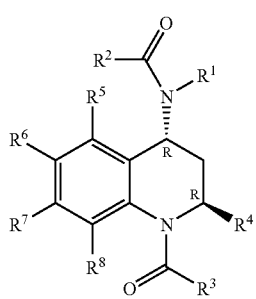

(Ic)

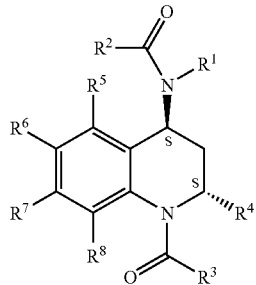

(Id)

$R^1$ is H, $(C_1-C_4)$alkyl, $(C_2-C_4)$alkenyl, $(C_2-C_4)$alkynyl or $(CH_2)_m-R^{11}$, in which $R^{11}$ is selected from aromatic heterocycle, phenyl and $(C_3-C_6)$cycloalkyl wherein the phenyl, the heterocycle and the cycloalkyl groups are unsubstituted or substituted by one to three groups independently selected from $Q^1$, and $(C_1-C_4)$alkyl optionally substituted with one to three groups which are the same or different and which are selected from $Q^1$ wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$ wherein $R^9$ and $R^{10}$ are the same or different and are selected from H and $(C_1-C_4)$alkyl;

m is an integer selected from 0, 1 and 2;

$R^2$ is $(C_1-C_4)$alkyl, wherein the alkyl group is substituted with one to three substituents independently selected from halogen, $OR^9$, $NR^9R^{10}$, $COOR^9$, $C(=O)NR^9R^{10}$, $NHSO_2R^9$ and $C(=O)(C_1-C_4)$alkyl;

$R^3$ is $(C_3-C_6)$cycloalkyl or $-A-R^{13}$, wherein

A is a bond, $(C_1-C_3)$alkylene or $(C_2-C_3)$alkenylene;

$R^{13}$ is $(C_6-C_{12})$aryl or a 5- to 10-membered heterocycle, optionally aromatic, wherein the aryl and the heterocycle groups are unsubstituted or substituted by one to three substituents independently selected from $(C_6-C_{12})$aryl, an aromatic heterocycle, $Q^2$, and $(C_1-C_4)$alkyl optionally substituted with one to three groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(=O)R^{10}$ and $C(=O)R^9$;

$R_4$ is 1$(_1-C_4)$-alkyl;

$R^5$, $R^6$, $R^7$ and $R^8$ are the same or different and are selected from

H, $Q^3$, and $(C_1-C_4)$alkyl optionally substituted with one to three groups which are the same or different and which are selected from $Q^3$, wherein $Q^3$ is selected from halogen, $NO_2$, CN, $SO_2CH_3$, $SO_2NR^9R^{10}$, $OR^9$, $SR^9$, $COOR^9$, $C(=O)NR^9R^{10}$, $NR^9R^{10}$, $NR^9SO_2R^{10}$, $NR^9C(=O)R^{10}$ and $C(=O)R^9$;

an N-oxide thereof or a pharmaceutically acceptable salt of the compound or N-oxide.

4. A compound according to claim 1 wherein $R^1$ is H, $(C_1-C_4)$alkyl, $(C_2-C_4)$alkenyl, $(C_2-C_4)$alkynyl or $(CH_2)_m-R^{r1}$, wherein
  $R^{r1}$ is selected from phenyl and $(C_3-C_6)$cycloalkyl wherein the phenyl and the cycloalkyl groups are unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

5. A compound according to claim 2 wherein $R^1$ is H, $(C_1-C_4)$alkyl, $(C_2-C_4)$alkenyl, $(C_2-C_4)$alkynyl or $(CH_2)_m-R^{r1}$, wherein
  $R^{r1}$ is selected from phenyl and $(C_3-C_6)$cycloalkyl wherein the phenyl and the cycloalkyl groups are unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

6. A compound according to claim 3 wherein $R^1$ is H, $(C_1-C_4)$alkyl, $(C_2-C_4)$alkenyl, $(C_2-C_4)$alkynyl or $(CH_2)_m-R^{r1}$, wherein
  $R^{r1}$ is selected from phenyl and $(C_3-C_6)$cycloalkyl wherein the phenyl and the cycloalkyl groups are unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

7. A compound according to claim 4 wherein $R^1$ is $(CH_2)_m-R^{r1}$, wherein
  $R^{r1}$ is selected from phenyl and $(C_3-C_6)$cycloalkyl wherein the phenyl and the cycloalkyl groups are unsubstituted or substituted by 1 to 3 groups selected from $OR^9$, $COOR^9$ and $(C_1-C_4)$alkyl optionally substituted with $COOR^9$, and
  m is an integer selected from 0 and 1.

8. A compound according to claim 5 wherein $R^1$ is $(CH_2)_m-R^{r1}$, wherein
  $R^{r1}$ is selected from phenyl and $(C_3-C_6)$cycloalkyl wherein the phenyl and the cycloalkyl groups are unsubstituted or substituted by 1 to 3 groups selected from $OR^9$, $COOR^9$ and $(C_1-C_4)$alkyl optionally substituted with $COOR^9$, and
  m is an integer selected from 0 and 1.

9. A compound according to claim 6 wherein $R^1$ is $(CH_2)_m-R^{r1}$, wherein
  $R^{r1}$ is selected from phenyl and $(C_3-C_6)$cycloalkyl wherein the phenyl and the cycloalkyl groups are unsubstituted or substituted by 1 to 3 groups selected from $OR^9$, $COOR^9$ and $(C_1-C_4)$alkyl optionally substituted with $COOR^9$, and
  m is an integer selected from 0 and 1.

10. A compound according to claim 1 wherein $R^1$ is $(C_1-C_4)$alkyl, $(C_2-C_4)$alkenyl, $(C_2-C_4)$alkynyl or $(CH_2)_m-R^{r1}$, in which
  $R^{r1}$ is selected from aromatic heterocycle and $(C_3-C_6)$cycloalkyl wherein the heterocycle and the cycloalkyl groups are unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

11. A compound according to claim 2 wherein $R^1$ is $(C_1-C_4)$alkyl, $(C_2-C_4)$alkenyl, $(C_2-C_4)$alkynyl or $(CH_2)_m-R^{r1}$, in which
  $R^{r1}$ is selected from aromatic heterocycle and $(C_3-C_6)$cycloalkyl wherein the heterocycle and the cycloalkyl groups are unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

12. A compound according to claim 3 wherein $R^1$ is $(C_1-C_4)$alkyl, $(C_2-C_4)$alkenyl, $(C_2-C_4)$alkynyl or $(CH_2)_m-R^{r1}$, in which
  $R^{r1}$ is selected from aromatic heterocycle and $(C_3-C_6)$cycloalkyl wherein the heterocycle and the cycloalkyl groups are unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

13. A compound according to claim 10 wherein $R^1$ is a $(C_3-C_6)$cycloalkyl wherein the cycloalkyl group is unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

14. A compound according to claim 11 wherein $R^1$ is a $(C_3-C_6)$cycloalkyl wherein the cycloalkyl group is unsubstituted or substituted by one to three groups selected from
  $Q^1$, and
  $(C_1-C_4)$alkyl optionally substituted with one to three groups which are the same or different and which are selected from $Q^1$,
wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

15. A compound according to claim 12 wherein $R^1$ is a $(C_3-C_6)$cycloalkyl wherein the cycloalkyl group is unsubstituted or substituted by one to three groups selected from
  $Q^1$, and ($C_1$–$C_4$)alkyl optionally substituted with one to three groups which are the same or different and which are selected from $Q^1$, wherein $Q^1$ is selected from halogen, $NO_2$, CN, $SO_2CH_3$, $SO_2NR^9R^{10}$, $OR^9$, $COOR^9$, $C(=O)NR^9R^{10}$, $NR^9R^{10}$, $NR^9SO_2R^{10}$, $NR^9C(=O)R^{10}$ and $C(=O)R^9$.

16. A compound according to claim 13 wherein $R^1$ is ($C_3$–$C_6$)cycloalkyl.

17. A compound according to claim 14 wherein $R^1$ is ($C_3$–$C_6$)cycloalkyl.

18. A compound according to claim 15 wherein $R^1$ is ($C_3$–$C_6$)cycloalkyl.

19. A compound according to claim 4 wherein $R^1$ is phenyl unsubstituted or substituted in the para position by a substituent selected from halogen, $OR^9$, $CH_2COOR^9$ and $CH_2COOR^9$.

20. A compound according to claim 5 wherein $R^1$ is phenyl unsubstituted or substituted in the para position by a substituent selected from halogen, $OR^9$, $CH_2COOR^9$ and $CH_2COOR^9$.

21. A compound according to claim 6 wherein $R^1$ is phenyl unsubstituted or substituted in the para position by a substituent selected from halogen, $OR^9$, $CH_2COOR^9$ and $CH_2COOR^9$.

22. A compound according to any one of claim 1 to 21 wherein $R^2$ is ($C_1$–$C_4$) alkyl.

23. A compound according to any one of claim 1 to 21 wherein $R^4$ is ($C_1$–$C_4$) alkyl.

24. A compound according to claim 22 wherein $R^3$ is selected from ($C_3$–$C_6$) cycloalkyl and -A-$R^{13}$, wherein A is a bond, ($C_1$–$C_3$)alkylene, straight or branched, or ($C_2$–$C_3$)alkenylene;

$R^{13}$ is a 5- to 10-membered heterocycle, optionally aromatic, unsubstituted or substituted by 1 to 3 substituents selected from ($C_6$–$C_{12}$)aryl, an heterocycle, $Q^2$, and ($C_1$–$C_4$)alkyl optionally substituted with 1 to 3 groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(O)R^{10}$ and $C(=O)R^9$, with the proviso that $R^3$ is not selected from unsubstituted thienyl or unsubstituted furanyl.

25. A compound according to claim 23 wherein $R^3$ is selected from ($C_3$–$C_6$) cycloalkyl and -A-$R^{13}$, wherein A is a bond, ($C_1$–$C_3$)alkylene, straight or branched, or ($C_2$–$C_3$)alkenylene;

$R^{13}$ is a 5- to 10-membered heterocycle, optionally aromatic, unsubstituted or substituted by 1 to 3 substituents selected from ($C_6$–$C_{12}$)aryl, an heterocycle, $Q^2$, and ($C_1$–$C_4$)alkyl optionally substituted with 1 to 3 groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(O)R^{10}$ and $C(=O)R^9$, with the proviso that $R^3$ is not selected from unsubstituted thienyl or unsubstituted furanyl.

26. A compound according to claim 22 wherein $R^3$ is selected from -A-$R^{13}$, wherein A is a bond, straight or branched ($C_1$–$C_3$)alkylene, or ($C_2$–$C_3$)alkenylene;

$R^{13}$ is a phenyl, unsubstituted or substituted by one to three substituents selected from ($C_6$–$C_{12}$)aryl, n heterocycle, $Q^2$, and ($C_1$–$C_4$)alkyl optionally substituted with one to three groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(O)R^{10}$ and $C(=O)R^9$.

27. A compound according to claim 23 wherein $R^3$ is selected from -A$R^{13}$, wherein A is a bond, straight or branched ($C_1$–$C_3$)alkylene, or ($C_2$–$C_3$)alkenylene;

$R^{13}$ is a phenyl, unsubstituted or substituted by one to three substituents selected from ($C_6$–$C_{12}$)aryl, n heterocycle, $Q^2$, and ($C_1$–$C_4$)alkyl optionally substituted with one to three groups which are the same or different and which are selected from $Q^2$, wherein $Q^2$ is selected from halogen, $NO_2$, CN, $SO_2CH_3$, $SO_2NR^9R^{10}$, $OR^9$, $SR^9$, $OCH_2CF_3$, $COOR^9$, $C(=O)NR^9R^{10}$, $NR^9R^{10}$, $NR^9SO_2R^{10}$, $NR^9C(O)R^{10}$ and $C(=O)R^9$.

28. A compound according to claim 24 wherein $R^5$, $R^6$, $R^7$ and $R^8$ are the same or different and are selected from H, halogen and $OR^9$.

29. A compound according to claim 25 wherein $R^5$, $R^6$, $R^7$ and $R^8$ are the same or different and are selected from H, halogen and $OR^9$.

30. A compound according to claim 26 wherein $R^5$, $R^6$, $R^7$ and $R^8$ are the same or different and are selected from H, halogen and $OR^9$.

31. A compound according to claim 27 wherein $R^5$, $R^6$, $R^7$ and $R^8$ are the same or different and are selected from H, halogen and $OR^9$.

32. A compound selected from the group consisting of
Cis-N-[2-Methyl-1-(pyridine-4-carbonyl)-1,2,3,4-tetrahydroquinolin-4-yl]-N-phenyl-acetamide;
Cis-N-[2-Methyl-1-(1-oxy-pyridine-4-carbonyl)-1,2,3,4-tetrahydroquinolin-4-yl]-N-phenyl-acetamide;
Cis-N-[1-(4-Hydroxy-benzoyl)-2-methyl-1,2,3,4-tetrahydroquinolin-4-yl]-N-phenyl-acetamide;
Cis-N-[2-Methyl-1-(4-trifluoromethyl-benzoyl)-1,2,3,4-tetrahydroquinolin-4-yl]-N-phenyl-acetamide;
Cis-N-[1-(4-Cyano-benzoyl)-2-methyl-1,2,3,4-tetrahydroquinolin-4-yl]-N-phenyl-acetamide;
Cis-N-[1-(4-Chloro-benzoyl)-2-methyl-1,2,3,4-tetrahydroquinolin-4-yl]-N-phenyl-acetamide;
4-[Cis-4-(Acetyl-phenyl-amino)-2-methyl-3,4-dihydro-2H-quinoline-1-carbonyl]-benzoic acid methyl ester;
4-[Cis-4-(Acetyl-phenyl-amino)-2-methyl-3,4-dihydro-2H-quinoline-1-carbonyl]-benzoic acid;
Cis-N-[2-Methyl-1-(3-phenyl-propionyl)-1,2,3,4-tetrahydroquinolin-4-yl]-N-phenyl-acetamide;
Cis-N-[2-Methyl-1-(5-methyl-thiophene-2-carbonyl)-1,2,3,4-tetrahydroquinolin-4-yl]-N-phenyl-acetamide;
Cis-N-[1-(Benzofurazan-5-carbonyl)-2-methyl-1,2,3,4-tetrahydroquinolin-4-yl]-N-phenyl-acetamide;
Cis-N-(2-Methyl-1-phenylacetyl-1,2,3,4-tetrahydro-quinolin-4-yl)-N-phenyl-acetamide;
Cis-N-[2-Methyl-1-(pyrazine-2-carbonyl)-1,2,3,4-tetrahydroquinolin-4-yl]-N-phenyl-acetamide;
Cis-N-[1-(6-Chloro-pyridine-3-carbonyl)-2-methyl-1,2,3,4-tetrahydroquinolin-4-yl]-N-phenyl-acetamide;

Cis-N-[2-Methyl-1-(6-trifluoromethyl-pyridine-3-carbonyl)-1,2,3,4-tetrahydroquinolin-4-yl]-N-phenyl-acetamide;
Cis-N-[1-(2,6-Dimethoxy-pyridine-3-carbonyl)-2-methyl-1,2,3,4-tetrahydroquinolin-4-yl]-N-phenyl-acetamide;
Cis-N-[1-(2-Methoxy-pyridine-3-carbonyl)-2-methyl-1,2,3,4-tetrahydroquinolin-4-yl]-N-phenyl-acetamide;
Cis-N-[2-Methyl-1-(2-methylsulfanyl-pyridine-3-carbonyl)-1,2,3,4-tetrahydroquinolin-4-yl]-N-phenyl-acetamide;
Cis-N-[1-(2-Chloro-pyridine-3-carbonyl)-2-methyl-1,2,3,4-tetrahydroquinolin-4-yl]-N-phenyl-acetamide;
Cis-N-[2-Methyl-1-(5-methyl-pyrazine-2-carbonyl)-1,2,3,4-tetrahydroquinolin-4-yl]-N-phenyl-acetamide;
Cis-N-[1-(2-Chloro-6-methyl-pyridine-3-carbonyl)-2-methyl-1,2,3,4-tetrahydroquinolin-4-yl]-N-phenyl-acetamide;
Cis-N-[1-(4-Chloro-1,3-dimethyl-1H-pyrazolo[3,4-b]pyridine-3-carbonyl)-2-methyl-1,2,3,4-tetrahydroquinolin-4-yl]-N-phenyl-acetamide;
Cis-N-[2-Methyl-1-(6-(2,2,2-trifluoro-ethoxy)-pyridine-3-carbonyl)-1,2,3,4-tetrahydroquinolin-4-yl]-N-phenyl-acetamide;
Cis-N-[2-Methyl-1-(2-propylsulfanyl-pyridine-3-carbonyl)-1,2,3,4-tetrahydroquinolin-4-yl]-N-phenyl-acetamide;
Cis-N-[1-(5,6-Dichloro-pyridine-3-carbonyl)-2-methyl-1,2,3,4-tetrahydroquinolin-4-yl]-N-phenyl-acetamide;
Cis-N-[1-(2,6-Dichloro-pyridine-3-carbonyl)-2-methyl-1,2,3,4-tetrahydroquinolin-4-yl]-N-phenyl-acetamide;
Cis-N-[2-Methyl-1-(4-methyl-[1,2,3]thiadiazole-5-carbonyl)-1,2,3,4-tetrahydroquinolin-4-yl]-N-phenyl-acetamide;
Cis-N-[2-Methyl-1-(5-methyl-isoxazole-3-carbonyl)-1,2,3,4-tetrahydroquinolin-4-yl]-N-phenyl-acetamide;
Cis-N-[1-(2,5-Dimethyl-2H-pyrazole-3-carbonyl)-2-methyl-1,2,3,4-tetrahydroquinolin-4-yl]-N-phenyl-acetamide;
Cis-N-[2-Methyl-1-(1-methyl-1H-pyrrole-2-carbonyl)-1,2,3,4-tetrahydroquinolin-4-yl]-N-phenyl-acetamide;
Cis-N-[1-(Isoxazole-5-carbonyl)-2-methyl-1,2,3,4-tetrahydroquinolin-4-yl]-N-phenyl-acetamide;
Cis-N-[2-Methyl-1-(5-methyl-isoxazole-4-carbonyl)-1,2,3,4-tetrahydroquinolin-4-yl]-N-phenyl-acetamide;
Cis-N-[1-(2,4-Dimethyl-thiazole-5-carbonyl)-2-methyl-1,2,3,4-tetrahydroquinolin-4-yl]-N-phenyl-acetamide;
Cis-N-[1-(5-Chloro-thiophene-2-carbonyl)-2-methyl-1,2,3,4-tetrahydroquinolin-4-yl]-N-phenyl-acetamide;
Cis-N-[1-(1,5-Dimethyl-1H-pyrazole-3-carbonyl)-2-methyl-1,2,3,4-tetrahydroquinolin-4-yl]-N-phenyl-acetamide;
Cis-N-[2-Methyl-1-(4-methyl-isothiazole-5-carbonyl)-1,2,3,4-tetrahydroquinolin-4-yl]-N-phenyl-acetamide;
Cis-5-[4-(Acetyl-phenyl-amino)-2-methyl-3,4-dihydro-2H-quinoline-1-carbonyl]-thiophene-2-carboxylic acid dimethylamide;
Cis-N-[1-(4-Hydroxy-quinoline-6-carbonyl)-2-methyl-1,2,3,4-tetrahydroquinolin-4-yl]-N-phenyl-acetamide;
Cis-N-[1-(4-tert-Butyl-thiazole-2-carbonyl)-2-methyl-1,2,3,4-tetrahydroquinolin-4-yl]-N-phenyl-acetamide;
Cis-N-[1-(2-Ethyl-pyridine-4-carbonyl)-2-methyl-1,2,3,4-tetrahydroquinolin-4-yl]-N-phenyl-acetamide;
Cis-N-[1-(3,6-Dichloro-pyridine-2-carbonyl)-2-methyl-1,2,3,4-tetrahydroquinolin-4-yl]-N-phenyl-acetamide;
Cis-N-[1-(4-Chloro-2H-pyrazole-3-carbonyl)-2-methyl-1,2,3,4-tetrahydroquinolin-4-yl]-N-phenyl-acetamide;
Cis-2-[4-(Acetyl-phenyl-amino)-2-methyl-3,4-dihydro-2H-quinoline-1-carbonyl]-isonicotinic acid methyl ester;
Cis-N-[2-Methyl-1-(4-[1,2,4]triazol-4-yl-benzoyl)-1,2,3,4-tetrahydroquinolin-4-yl]-N-phenyl-acetamide;
Cis-N-[1-(2,6-Dimethoxy-pyridine-4-carbonyl)-2-methyl 1,2,3,4-tetrahydroquinolin-4-yl]-N-phenyl-acetamide;
Cis-N-[1-(5-Ethyl-isoxazole-3-carbonyl)-2-methyl-1,2,3,4-tetrahydroquinolin-4-yl]-N-phenyl-acetamide;
Cis-N-[2-Methyl-1-(2-tetrazol-1-yl-pyridine-4-carbonyl)-1,2,3>4-tetrahydroquinolin-4-yl]-N-phenyl-acetamide;
Cis-N-[2-Methyl-1-(5-propyl-isoxazole-3-carbonyl)-1,2,3,4-tetrahydroquinolin-4-yl]-N-phenyl-acetamide;
Cis-N-[1-(5-Isobutyl-2-methyl-2H-pyrazole-3-carbonyl)-2-methyl-1,2,3,4-tetrahydroquinolin-4-yl]-N-phenyl-acetamide;
Cis-N-[1-(5-Bromo-furan-2-carbonyl)-2-methyl-1,2,3,4-tetrahydroquinolin-4-yl]-N-phenyl-acetamide;
Cis-N-[2-Methyl-1-(6-phenyl-pyridine-3-carbonyl)-1,2,3,4-tetrahydroquinolin-4-yl]-N-phenyl-acetamide;
Cis-N-[2-Methyl-1-(2-phenyl-pyridine-4-carbonyl)-1,2,3,4-tetrahydroquinolin-4-yl]-N-phenyl-acetamide;
Cis-N-[2-Methyl-1-(quinoline-6-carbonyl)-1,2,3,4-tetrahydroquinolin-4-yl]-N-phenyl-acetamide;
Cis-N-[1-(3,4-Dimethoxy-furan-2-carbonyl)-2-methyl-1,2,3,4-tetrahydroquinolin-4-yl]-N-phenyl-acetamide;
Cis-N-[2-Methyl-1-(3-methyl-furan-2-carbonyl)-1,2,3,4-tetrahydroquinolin-4-yl]-N-phenyl-acetamide;
Cis-N-[1-(2,5-Dimethyl-furan-3-carbonyl)-2-methyl-1,2,3,4-tetrahydroquinolin-4-yl]-N-phenyl-acetamide;
Cis-N-[1-(2,4-Dimethyl-oxazole-5-carbonyl)-2-methyl-1,2,3,4-tetrahydroquinolin-4-yl]-N-phenyl-acetamide;
Cis-N-[1-(5-Methoxymethyl-furan-2-carbonyl)-2-methyl-1,2,3,4-tetrahydroquinolin-4-yl]-N-phenyl-acetamide;
Cis-N-[1-(5-Fluoro-pyridine-3-carbonyl)-2-methyl-1,2,3,4-tetrahydroquinolin-4-yl]-N-phenyl-acetamide;
Cis-N-[2-Methyl-1-(quinoline-2-carbonyl)-1,2,3,4-tetrahydroquinolin-4-yl]-N-phenyl-acetamide;
Cis-N-[2-Methyl-1-(6-methyl-pyridine-3-carbonyl)-1,2,3,4-tetrahydroquinolin-4-yl]-N-phenyl-acetamide;
Cis-N-[2-Methyl-1-(quinoline-3-carbonyl)-1,2,3,4-tetrahydroquinolin-4-yl]-N-phenyl-acetamide;
Cis-N-[2-Methyl-1-(1H-pyrazole-3-carbonyl)-1,2,3,4-tetrahydroquinolin-4-yl]-N-phenyl-acetamide;
Cis-N-[2-Methyl-1-(2H-pyrazole-3-carbonyl)-1,2,3,4-tetrahydroquinolin-4-yl]-N-phenyl-acetamide;
Cis-N-[1-(5-Isobutyl-isoxazole-3-carbonyl)-2-methyl-1,2,3,4-tetrahydroquinolin-4-yl]-N-phenyl-acetamide;
Cis-N-[2-Methyl-1-(quinoline-4-carbonyl)-1,2,3,4-tetrahydroquinolin-4-yl]-N-phenyl-acetamide;
Cis-N-[2-Methyl-1-(6-methyl-pyridine-2-carbonyl)-1,2,3,4-tetrahydroquinolin-4-yl]-N-phenyl-acetamide;
Cis-N-[2-Methyl-1-(quinoxaline-5-carbonyl)-1,2,3,4-tetrahydroquinolin-4-yl]-N-phenyl-acetamide;
Cis-N-[1-(3-Methoxy-thiophene-2-carbonyl)-2-methyl-1,2,3,4-tetrahydroquinolin-4-yl]-N-phenyl-acetamide;
Cis-N-[1-(5-tert-Butyl-2-methyl-furan-3-carbonyl)-2-methyl-1,2,3,4-tetrahydroquinolin-4-yl]-N-phenyl-acetamide;
Cis-N-[1-(5-Ethyl-2-methyl-2H-pyrazole-3-carbonyl)-2-methyl-1,2,3,4-tetrahydroquinolin-4-yl]-N-phenyl-acetamide;
Cis-N-[2-Methyl-1-([1,2,5]thiadiazole-3-carbonyl)-1,2,3,4-tetrahydroquinolin-4-yl]-N-phenyl-acetamide;

Cis-N-[2-Methyl-1-(2-methyl-5-propyl-2H-pyrazole-3-carbonyl)-1,2,3,4-tetrahydroquinolin-4-yl]-N-phenyl-acetamide;
Cis-N-(1-Benzoyl-2-methyl-1,2,3,4-tetrahydroquinolin-4-yl]-N-Benzyl-acetamide;
Cis-N-Benzyl-N-[2-methyl-1-(thiophene-2-carbonyl)-1,2,3,4-tetrahydroquinolin-4-yl]-acetamide;
Trans-N-Benzyl-N-[2-methyl-1-(thiophene-2-carbonyl)-1,2,3,4-tetrahydroquinolin-4-yl]-acetamide;
Cis-N-Cyclohexyl-N-[2-methyl-1-(thiophene-2-carbonyl)-1,2,3,4-tetrahydroquinolin-4-yl]-acetamide;
Cis-N-(1-Benzoyl-6-methoxy-2-methyl-1,2,3,4-tetrahydroquinolin-4-yl)-N-phenyl-acetamide;
Cis-N-(1-Benzoyl-6-hydroxy-2-methyl-1,2,3,4-tetrahydroquinolin-4-yl)-N-phenyl-acetamide;
Cis-N-(1-Benzoyl-6-chloro-2-methyl-1,2,3,4-tetrahydroquinolin-4-yl)-N-phenyl-acetamide;
N-(1-Benzoyl-2-methyl-1,2,3,4-tetrahydroquinolin-4-yl)-N-prop-2-ynyl-acetamide;
Cis-N-(1-Benzoyl-2-methyl-1,2,3,4-tetrahydroquinolin-4-yl)-N-(4-methoxy-phenyl)-acetamide;
Cis-N-(1-Benzoyl-2-methyl-1,2,3,4-tetrahydroquinolin-4-yl)-N-(4-hydroxy-phenyl)-acetamide;
Cis-{4-[Acetyl-(1-benzoyl-2-methyl-1,2,3,4-tetrahydroquinolin-4-yl)-amino]-phenyl}-acetic acid ethyl ester;
Cis-N-(1-Benzoyl-2-methyl-1,2,3,4-tetrahydroquinolin-4^yl)-N-phenyl-malonamic acid methyl ester;
Cis-N-(1-Benzoyl-2-methyl-1,2,3,4-tetrahydroquinolin-4-yl)-N-phenyl-malonamic acid;
Cis-N-[2-Methyl-1-(pyridine-3-carbonyl)-1,2)3,4-tetrahydroquinolin-4-yl]-N-phenyl-acetamide;
Cis-N-(1-Benzoyl-2-methyl-1,2,3,4-tetrahydroquinolin-4-yl)-N-Cyclopropyl-acetamide;
Cis-N-Cyclopropyl-N-[2-methyl-1-(pyridine-3-carbonyl)-1,2,3)4-tetrahydroquinolin-4-yl]-acetamide;
(-f)-Cis-N-cyclopropyl-N-[2-methyl-1-(pyridine-3-carbonyl)-1,2,3,4-tetrahydroquinolin-4-yl]-acetamide;
(−)-Cis-N-cyclopropyl-N-[2-methyl-1 (pyridine-3-carbonyl)-1,2,3,4-tetrahydroquinolin-4-yl]-acetamide;
Cis-N-Cyclopropyl-N-[2-methyl-1-(3-methyl-isoxazole-5-carbonyl)-1,2,3,4-tetrahydroquinolin-4-yl]-acetamide;
Cis-N-Phenyl-N-[1-(thiophene-2-carbonyl)-1,2,3,4-tetrahydroquinolin-4-yl]-acetamide;
Cis-N-(1-Benzoyl-1,2,3,4-tetrahydroquinolin-4-yl)-N-phenyl-acetamide;
Cis-N-[2-Ethyl-1-(pyridine-3-carbonyl)-1,2,3,4-tetrahydroquinolin-4-yl]-N-phenyl-acetamide; and
Cis-N-Ethyl-N-[2-Methyl-1-(pyridine-3-carbonyl)-1,2,3,4-tetrahydroquinolin-yl]-acetamide.

33. A pharmaceutical composition comprising a compound of formula (I):

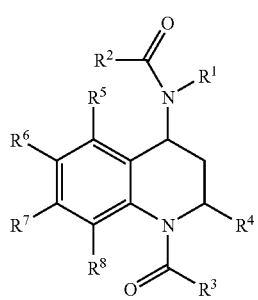

(I)

wherein
R$^1$ is H, (C$_1$–C$_4$)alkyl, (C$_2$–C$_4$)alkenyl, (C$_2$–C$_4$)alkynyl or (CH$_2$)$_m$—R$^{11}$, in which
R$^{11}$ is selected from aromatic heterocycle, phenyl and (C$_3$–C$_6$)cycloalkyl wherein the phenyl, the heterocycle and the cycloalkyl groups are unsubstituted or substituted by one to three groups independently selected from
Q$^1$, and
(C$_1$–C$_4$)alkyl optionally substituted with one to three groups which are the same or different and which are selected from Q$^1$,
wherein Q$^1$ is selected from halogen, NO$_2$, CN, SO$_2$CH$_3$, SO$_2$NR$^9$R$^{10}$, OR$^9$, COOR$^9$, C(=O)NR$^9$R$^{10}$, NR$^9$R$^{10}$, NR$^9$SO$_2$R$^{10}$, NR$^9$C(=O)R$^{10}$ and C(=O)R$^9$ wherein R$^9$, R$^{10}$, are the same or different and are selected from H and (C$_1$–C$_4$)alkyl;
m is an integer selected from 0, 1 and 2;
R$^2$ is (C$_1$–C$_4$)alkyl, wherein the alkyl group is substituted with one to three substituents independently selected from halogen, OR$^9$, NR$^9$R$^{10}$, COOR$^9$, C(=O)NR$^9$R$^{10}$, NHSO$_2$R$^9$ and C(=O)(C$_1$–C$_4$)alkyl;
R$^3$ is (C$_3$–C$_6$)cycloalkyl or -A-R$^{13}$, wherein
A is a bond, (C$_1$–C$_3$)alkylene or (C$_2$–C$_3$)alkenylene;
R$^{13}$ is (C$_6$–C$_{12}$)aryl or a 5- to 10-membered heterocycle, optionally aromatic, wherein the aryl and the heterocycle groups are unsubstituted or substituted by one to three substituents independently selected from
(C$_6$–C$_{12}$)aryl,
an aromatic heterocycle,
Q$^2$, and
(C$_1$–C$_4$)alkyl optionally substituted with one to three groups which are the same or different and which are selected from Q$^2$,
wherein Q$^2$ is selected from halogen, NO$_2$, CN, SO$_2$CH$_3$, SO$_2$NR$^9$R$^{10}$, OR$^9$, SR$^9$, OCH$_2$CF$_3$, COOR$^9$, C(=O)NR$^9$R$^{10}$, NR$^9$R$^{10}$, NR$^9$SO$_2$R$^{10}$, NR$^9$C(=O)R$^{10}$ and C(=O)R$^9$;
R$^4$ is H or (C$_1$–C$_4$)-alkyl;
R$^5$, R$^6$, R$^7$ and R$^8$ are the same or different and are selected from
H, Q$^3$, and
(C$_1$–C$_4$)alkyl optionally substituted with one to three groups which are the same or different and which are selected from Q$^3$,
wherein Q$^3$ is selected from halogen, NO$_2$, CN, SO$_2$CH$_3$, SO$_2$NR$^9$R$^{10}$, OR$^9$, SR$^9$, OCH$_2$CF$_3$ COOR$^9$, C(=O)NR$^9$R$^{10}$, NR$^9$R$^{10}$, NR$^9$SO$_2$R$^{10}$, NR$^9$C(=O)R$^{10}$ and C(=O)R$^9$;
an optical isomer thereof, an N-oxide thereof or a pharmaceutically acceptable salt of the compound, optical isomer or N-oxide together with a pharmaceutically acceptable carrier, excipient, diluent or delivery system.

* * * * *